US009220483B2

(12) United States Patent
Frankhouser et al.

(10) Patent No.: US 9,220,483 B2
(45) Date of Patent: Dec. 29, 2015

(54) MEDICAL TOOL WITH ELECTROMECHANICAL CONTROL AND FEEDBACK

(75) Inventors: Paul L. Frankhouser, Miami Beach, FL (US); Maureen L. Mulvihill, Bellefonte, PA (US); Roger B. Bagwell, Bellefonte, PA (US); Ryan S. Clement, State College, PA (US); Gabriela Hernandez Mesa, State College, PA (US); Ryan M. Sheehan, Altoona, PA (US); Brian M. Park, Bellefonte, PA (US)

(73) Assignee: Actuated Medical, Inc., Bellefonte, PA (US)

( * ) Notice: Subject to any disclaimer, the term of this patent is extended or adjusted under 35 U.S.C. 154(b) by 0 days.

(21) Appl. No.: 13/371,310

(22) Filed: Feb. 10, 2012

(65) Prior Publication Data

US 2012/0209303 A1    Aug. 16, 2012

Related U.S. Application Data

(63) Continuation-in-part of application No. 12/559,383, filed on Sep. 14, 2009, now Pat. No. 8,328,738, which (Continued)

(51) Int. Cl.
*A61B 10/00* (2006.01)
*A61B 10/02* (2006.01)
(Continued)

(52) U.S. Cl.
CPC ........... *A61B 10/025* (2013.01); *A61B 17/3401* (2013.01); *A61B 17/3415* (2013.01);
(Continued)

(58) Field of Classification Search
USPC ................................. 600/564, 567
See application file for complete search history.

(56) References Cited

U.S. PATENT DOCUMENTS 5,628,743 A    5/1997 Cimino
5,728,089 A    3/1998 Lal et al.
(Continued)

FOREIGN PATENT DOCUMENTS

CN       101431940 A    5/2009

OTHER PUBLICATIONS

International Searching Authority; International Search Report and Written Opinion of the International Searching Authority; International Application No. PCT/US2012/024762; Patent Cooperation Treaty; pp. 1-14; publisher United States Patent Office; Published Alexandria, Virginia, USA; copyright and mailing date Jun. 22, 2012; (14 pages).

(Continued)

*Primary Examiner* — Sean Dougherty
*Assistant Examiner* — Daniel Cerioni
(74) *Attorney, Agent, or Firm* — Metz Lewis Brodman Must O'Keefe LLC

(57) ABSTRACT

A medical device for reducing the force necessary to penetrate living being tissue using a variety of reciprocating motion actuators. The reciprocating actuator drives a penetrating member, such as a needle, through the tissue at a reduced force while the device detects the passage of the penetrating member through the tissue. Upon passage of the penetrating member through the tissue, a feedback system monitors electromechanical properties of a control signal of the device and automatically modifies control based thereon, e.g., electrical power to the reciprocating actuator is automatically terminated.

20 Claims, 55 Drawing Sheets

Related U.S. Application Data is a continuation-in-part of application No. 12/163,071, filed on Jun. 27, 2008, now Pat. No. 8,043,229.

(60) Provisional application No. 60/937,749, filed on Jun. 29, 2007, provisional application No. 61/441,500, filed on Feb. 10, 2011, provisional application No. 61/441,677, filed on Feb. 11, 2011.

(51) Int. Cl.
| | | |
|---|---|---|
| *A61B 17/34* | (2006.01) | |
| *A61B 17/32* | (2006.01) | |
| *A61B 17/00* | (2006.01) | |
| *A61B 19/00* | (2006.01) | |

(52) U.S. Cl.
CPC ..... *A61B17/320068* (2013.01); *A61B 17/3476* (2013.01); *A61B 2017/00115* (2013.01); *A61B 2017/00123* (2013.01); *A61B 2019/464* (2013.01)

(56) References Cited

U.S. PATENT DOCUMENTS

| | | |
|---|---|---|
| 6,402,769 B1 | 6/2002 | Boukhny |
| 6,423,014 B1 | 7/2002 | Churchill et al. |
| 2002/0026127 A1 | 2/2002 | Balbierz et al. |
| 2003/0109871 A1 | 6/2003 | Johnson et al. |
| 2004/0106894 A1 | 6/2004 | Hunter et al. |
| 2010/0004558 A1 | 1/2010 | Frankhouser et al. |

OTHER PUBLICATIONS

United States Patent and Trademark Office; Office Action; Office Action from U.S. Appl. No. 13/222,363;copyright and mailing date Dec. 11, 2014; pp. 1-9; publisher United States Patent and Trademark Office; Published Alexandria, Virginia, USA; copyright and mailing date Dec. 11, 2014; (9 pages).

The State Intellectual Property Office of the People's Republic of China; First Office Action; Office Action from Chinese Patent Application No. 201280017598.4; copyright and mailing date Apr. 9, 2015; pp. 18; publisher The State Intellectual Property Office of the People's Republic of China; Published Beijing City, People's Republic of China; copyright and mailing date Apr. 9, 2015; (18 pages).

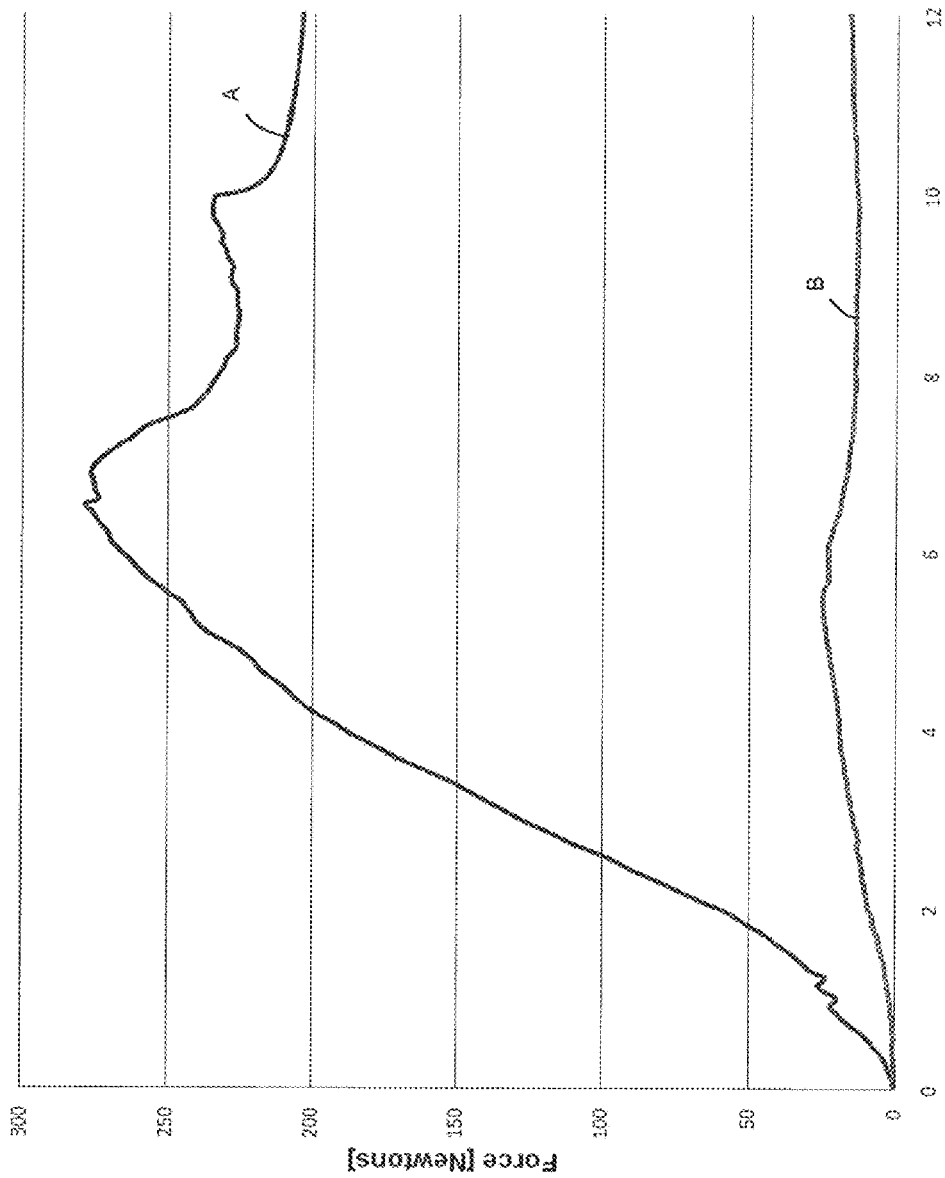

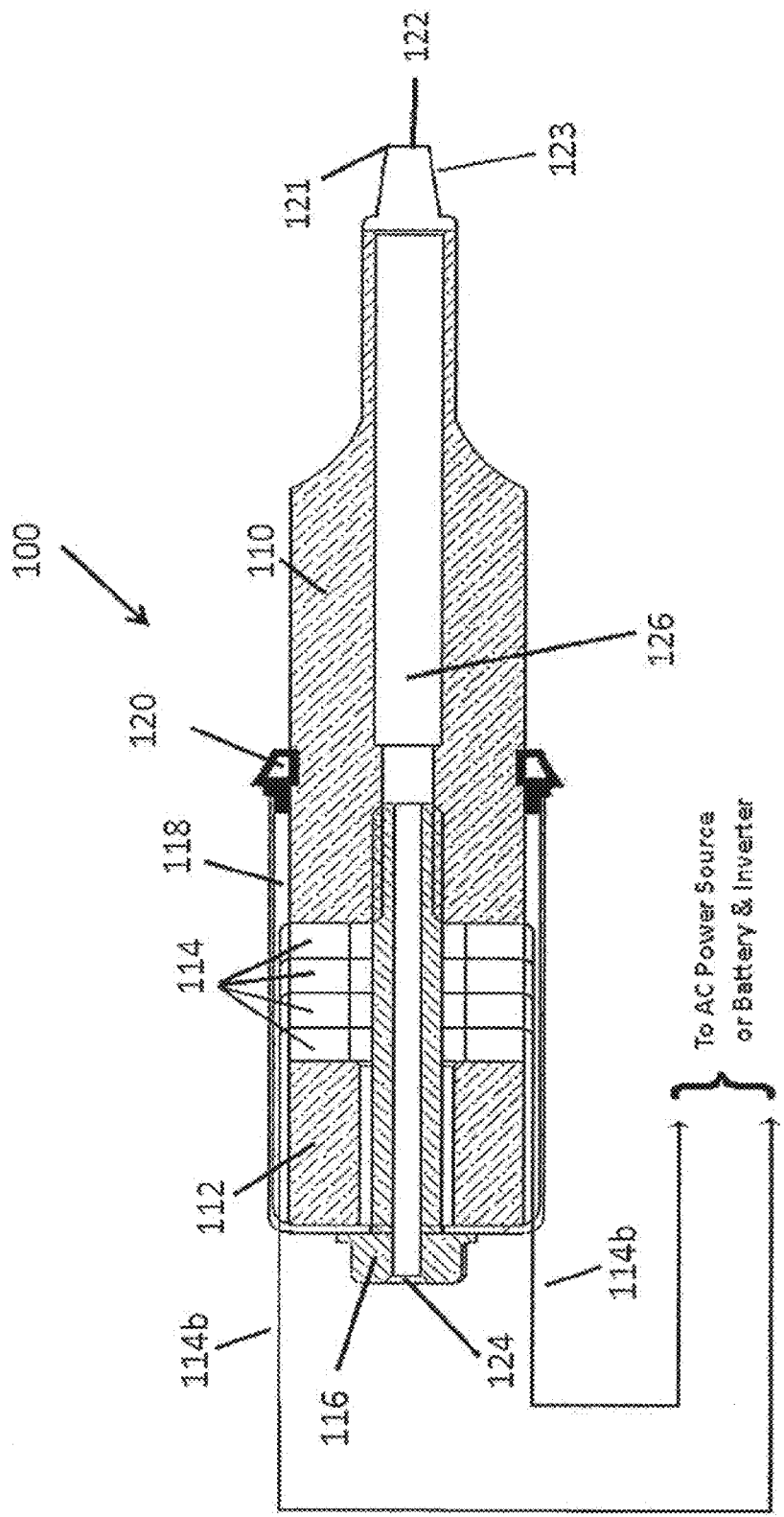

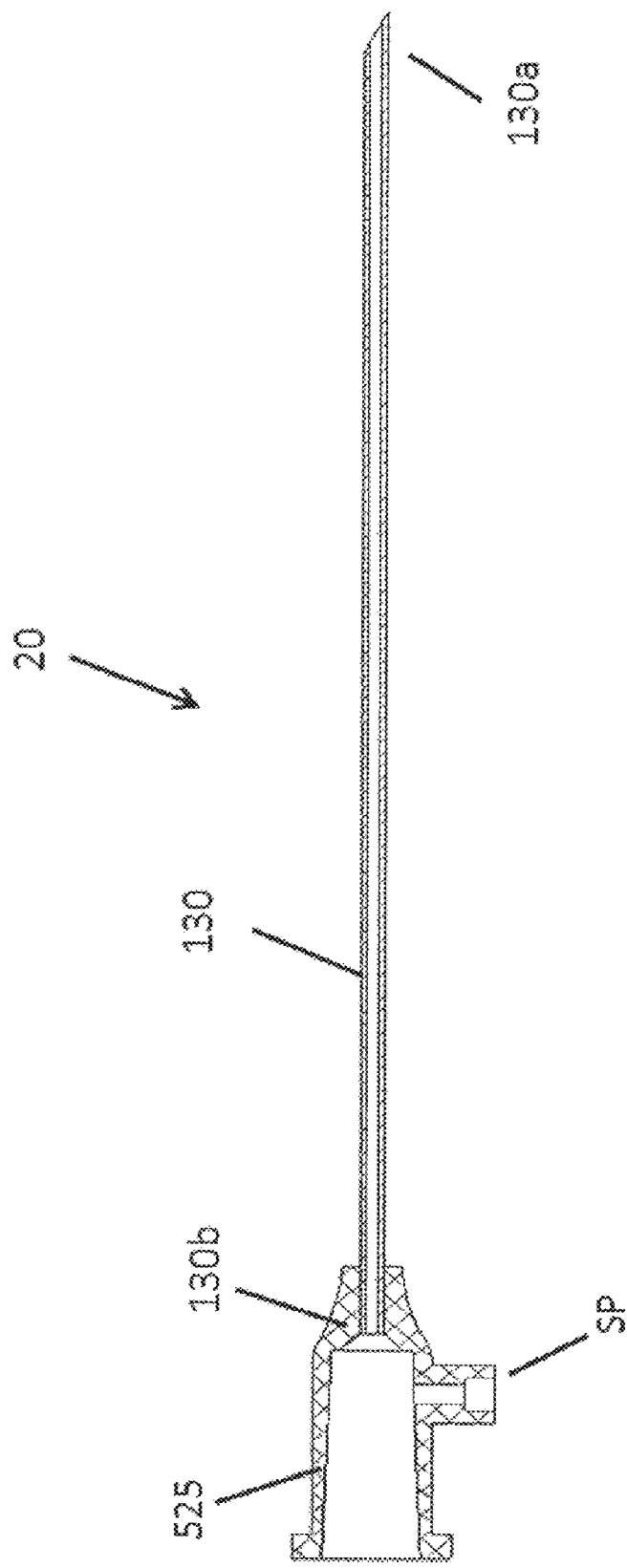

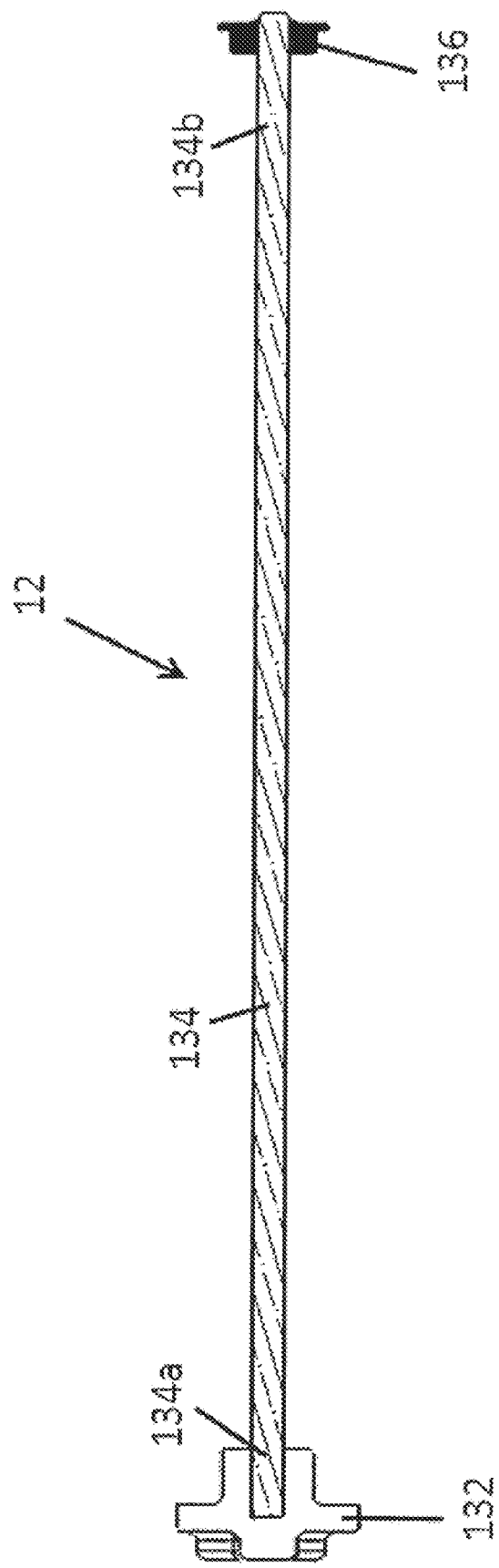

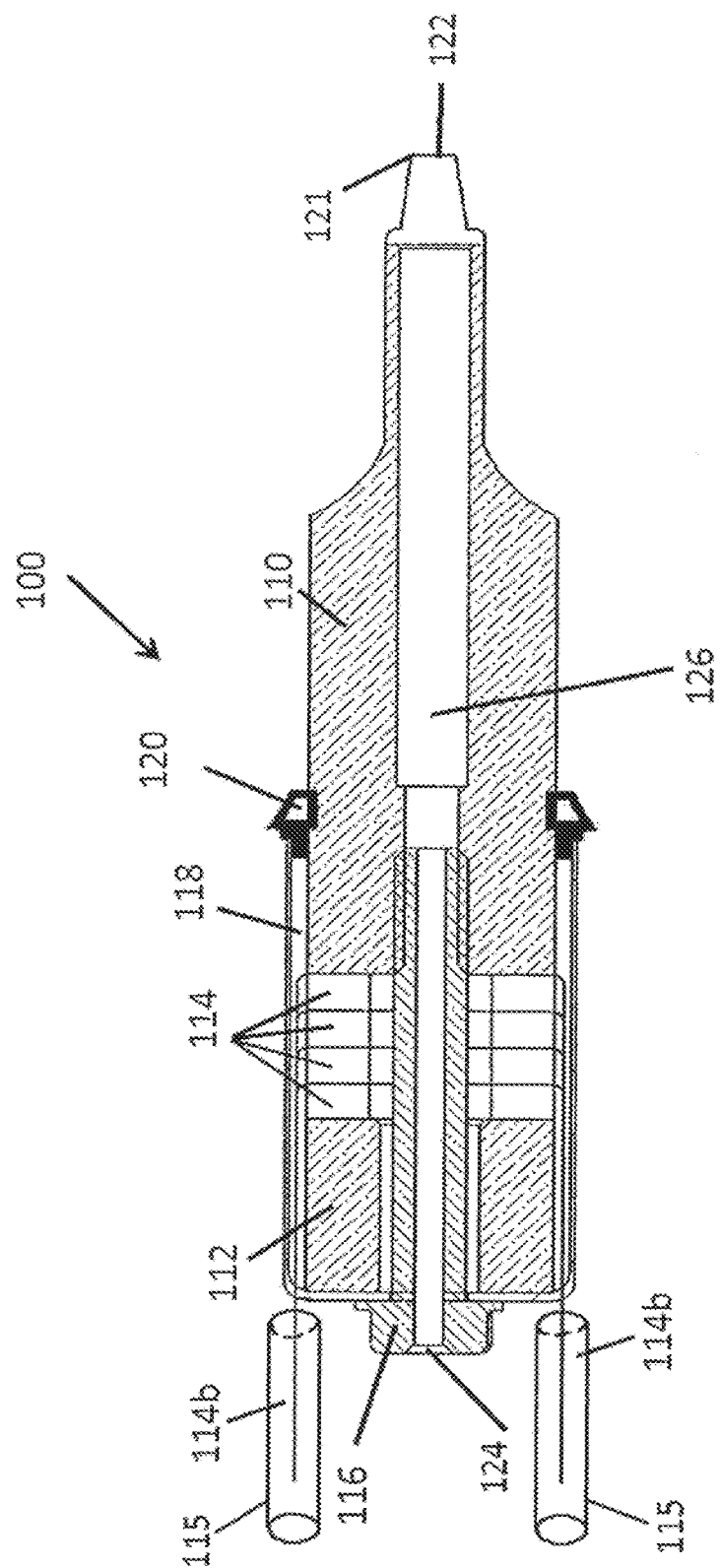

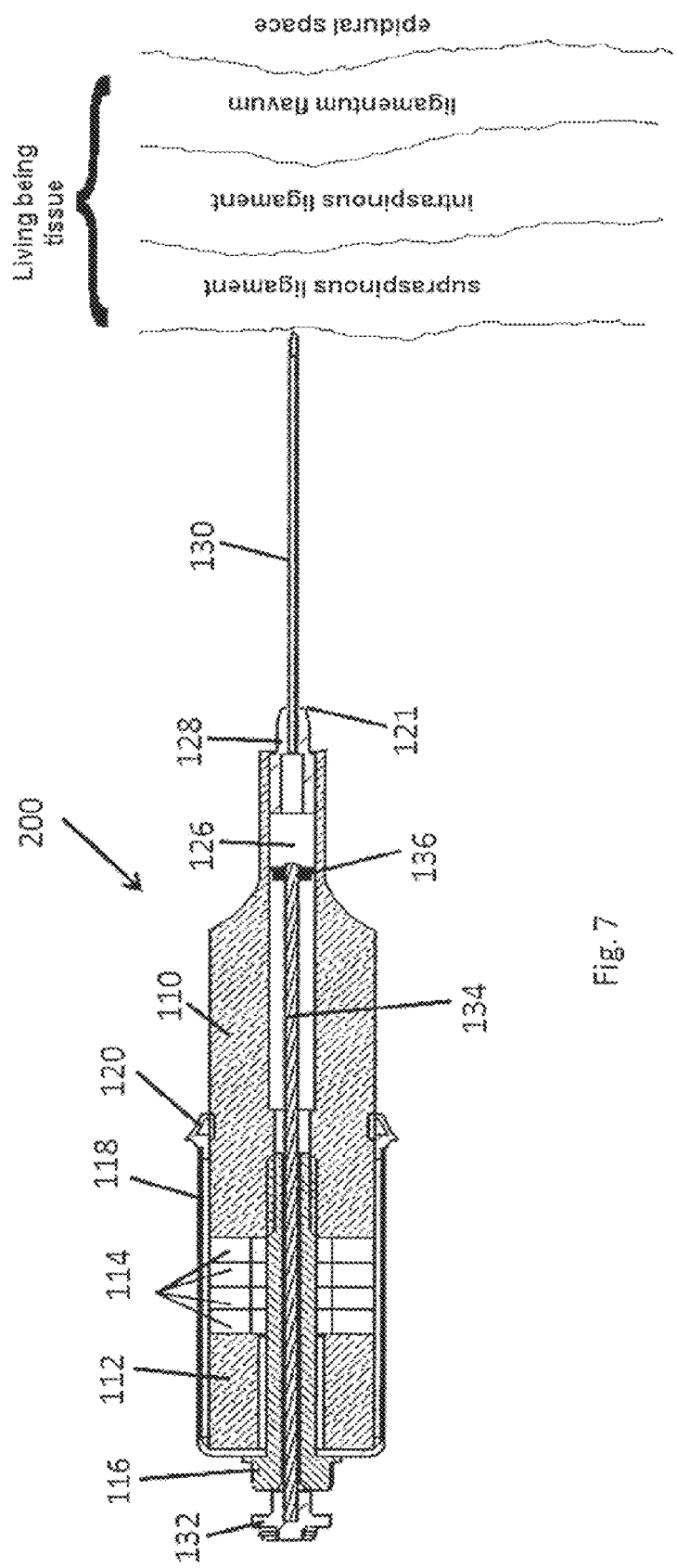

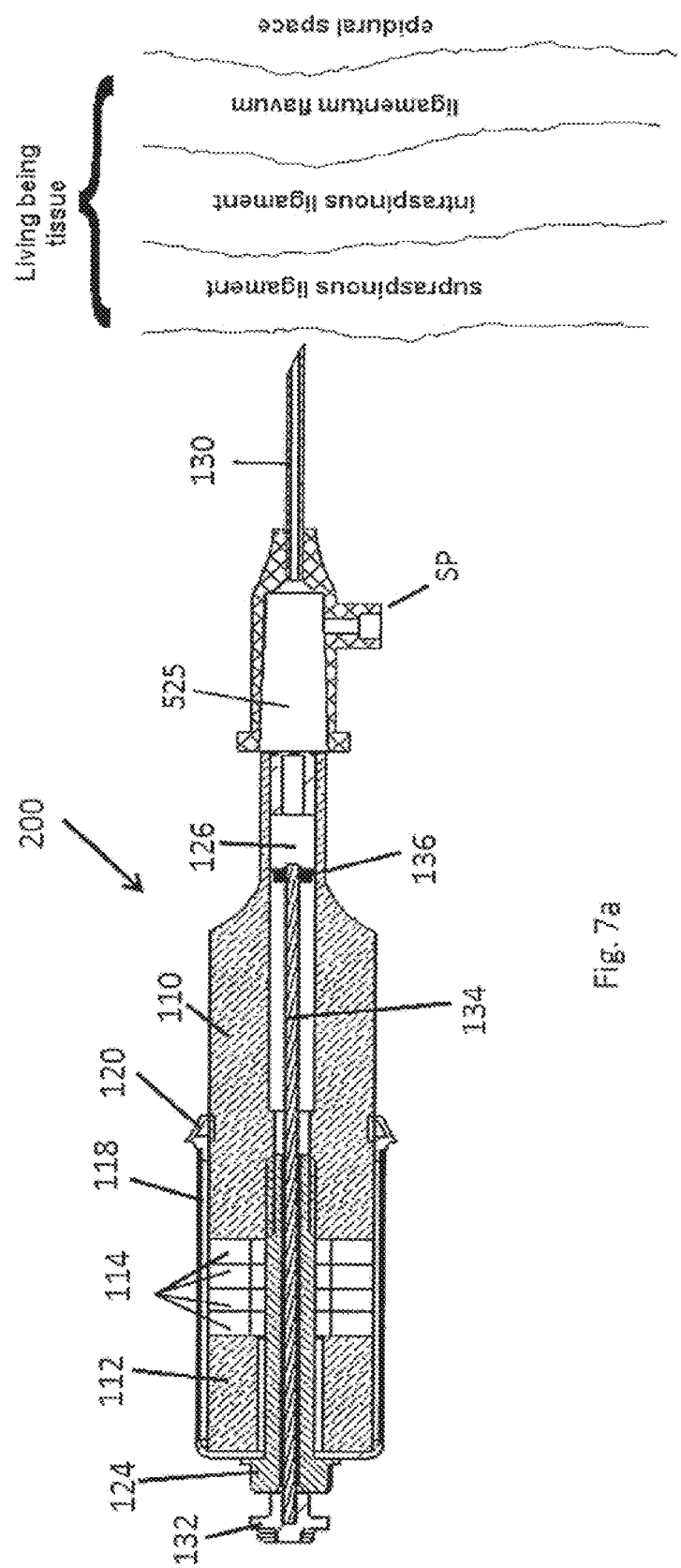

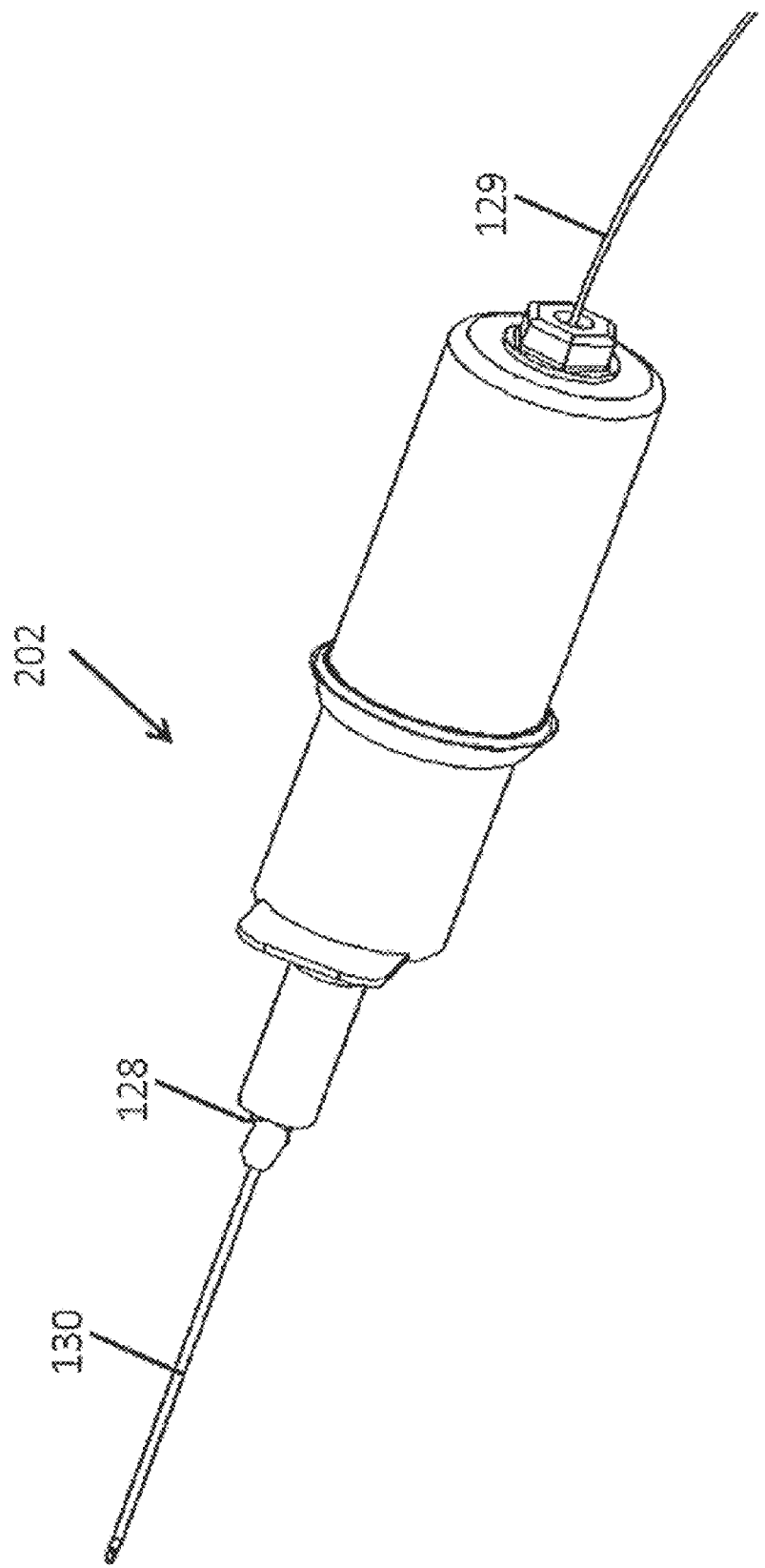

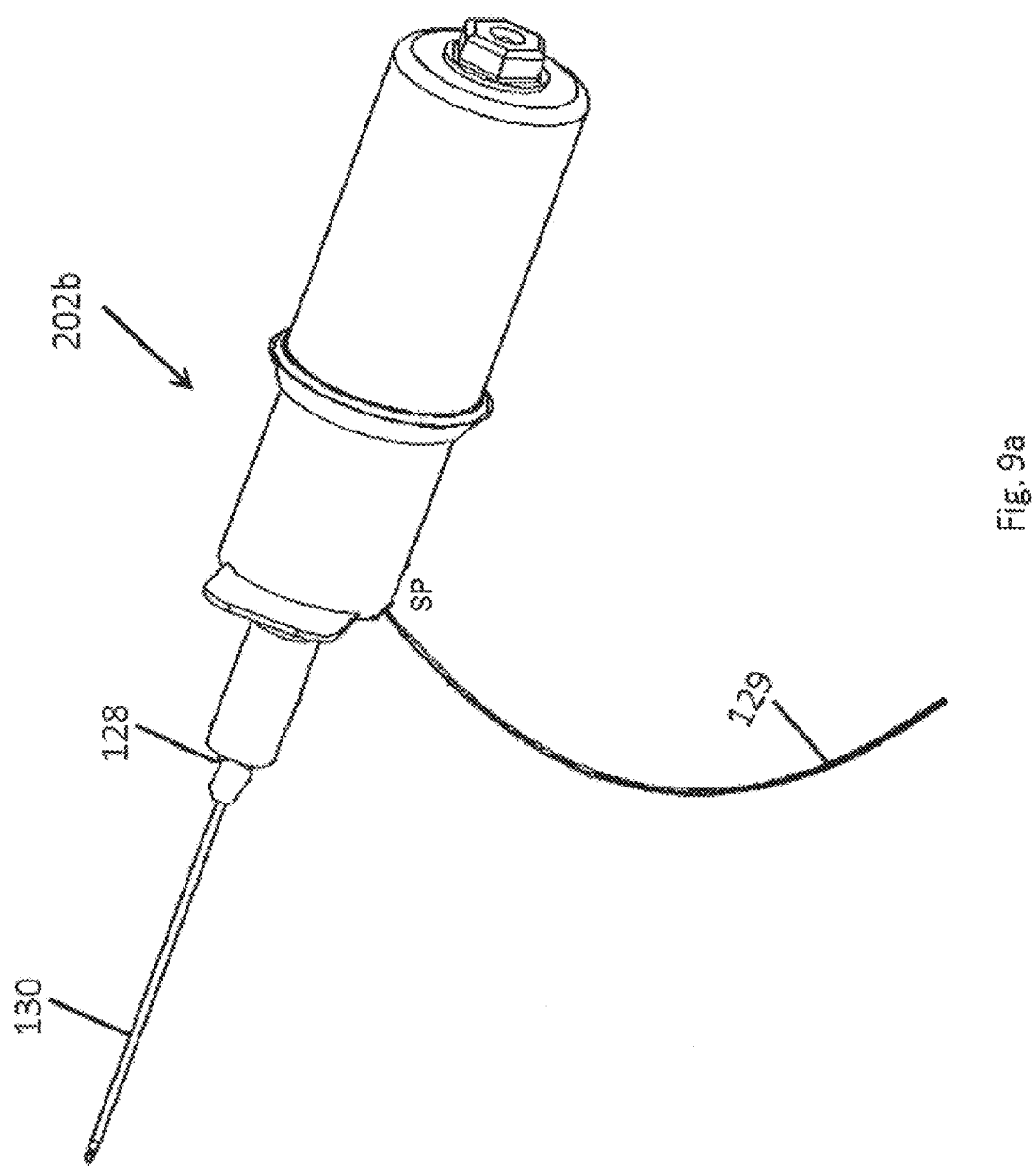

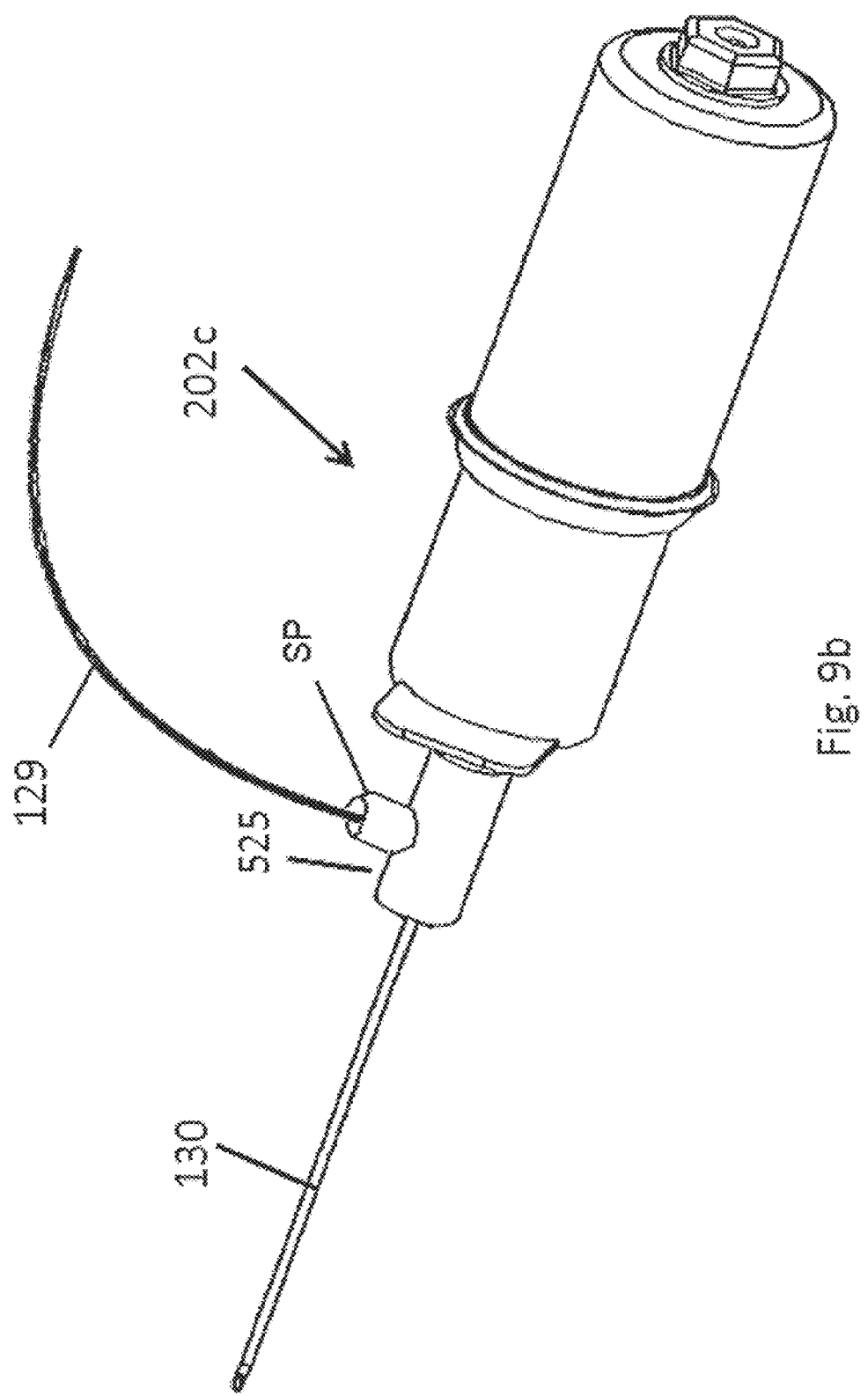

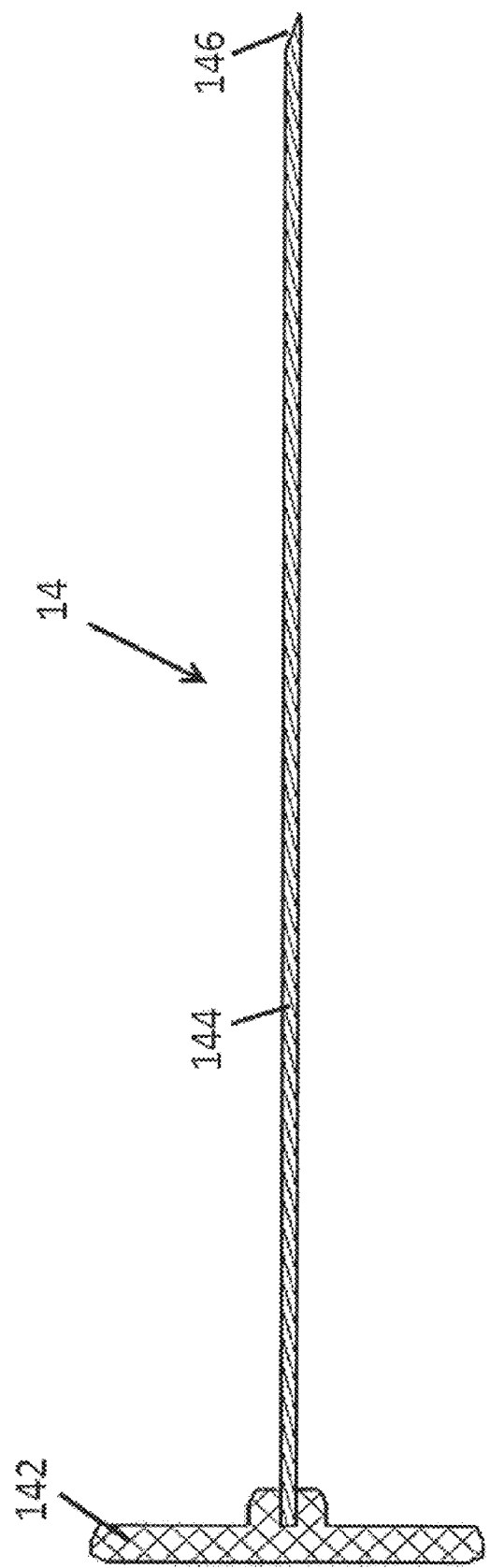

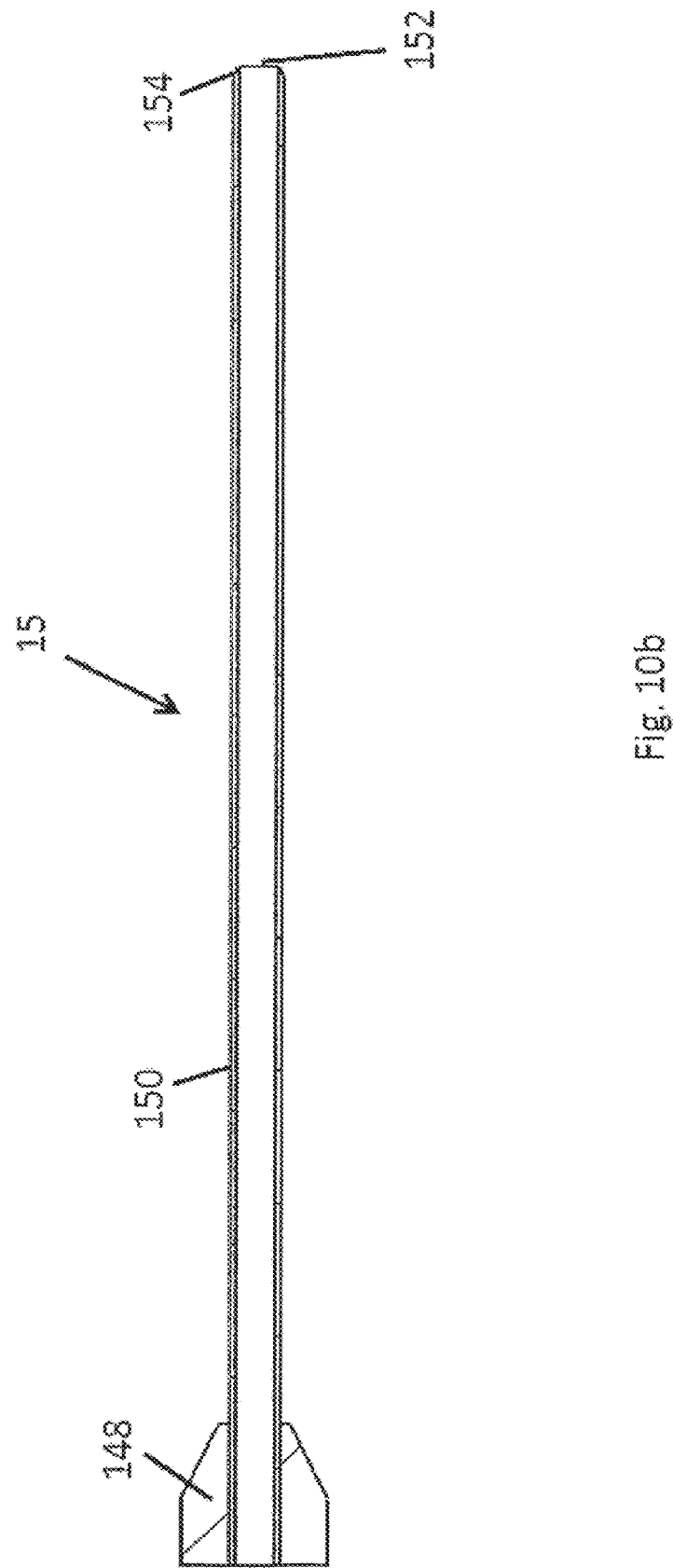

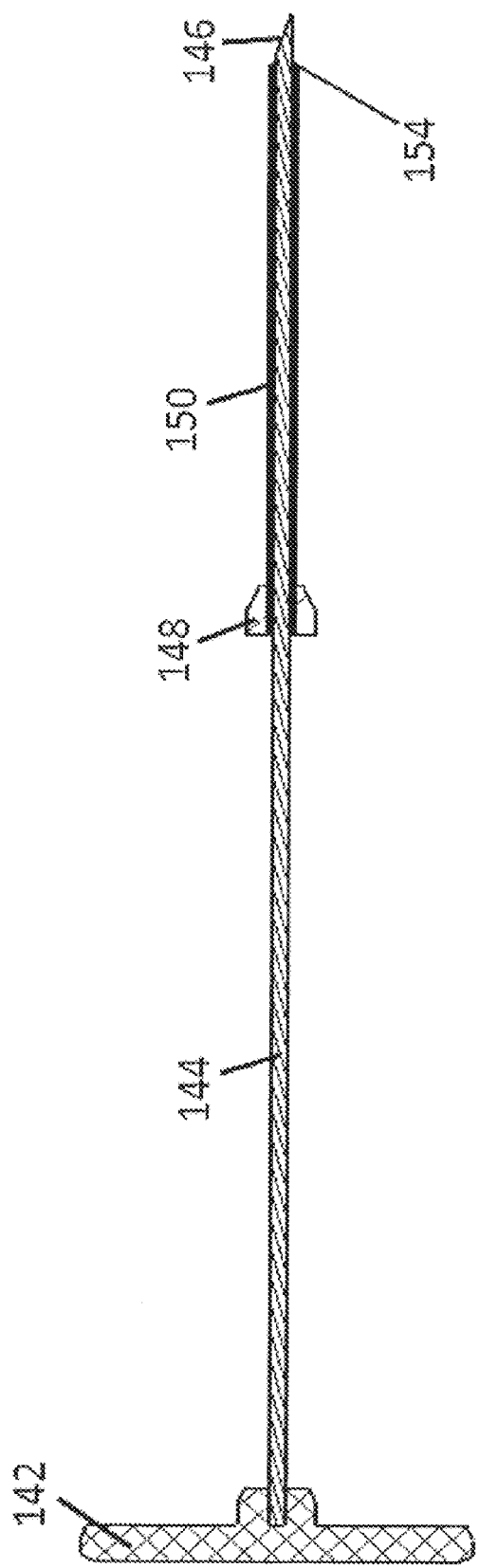

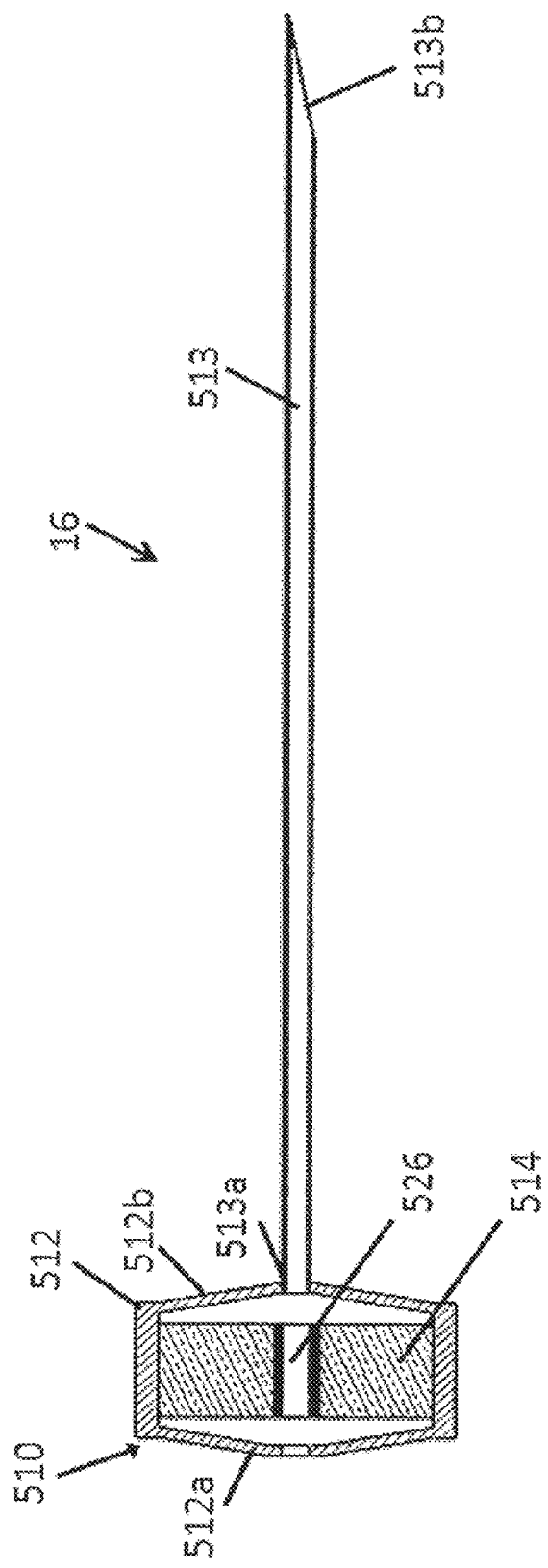

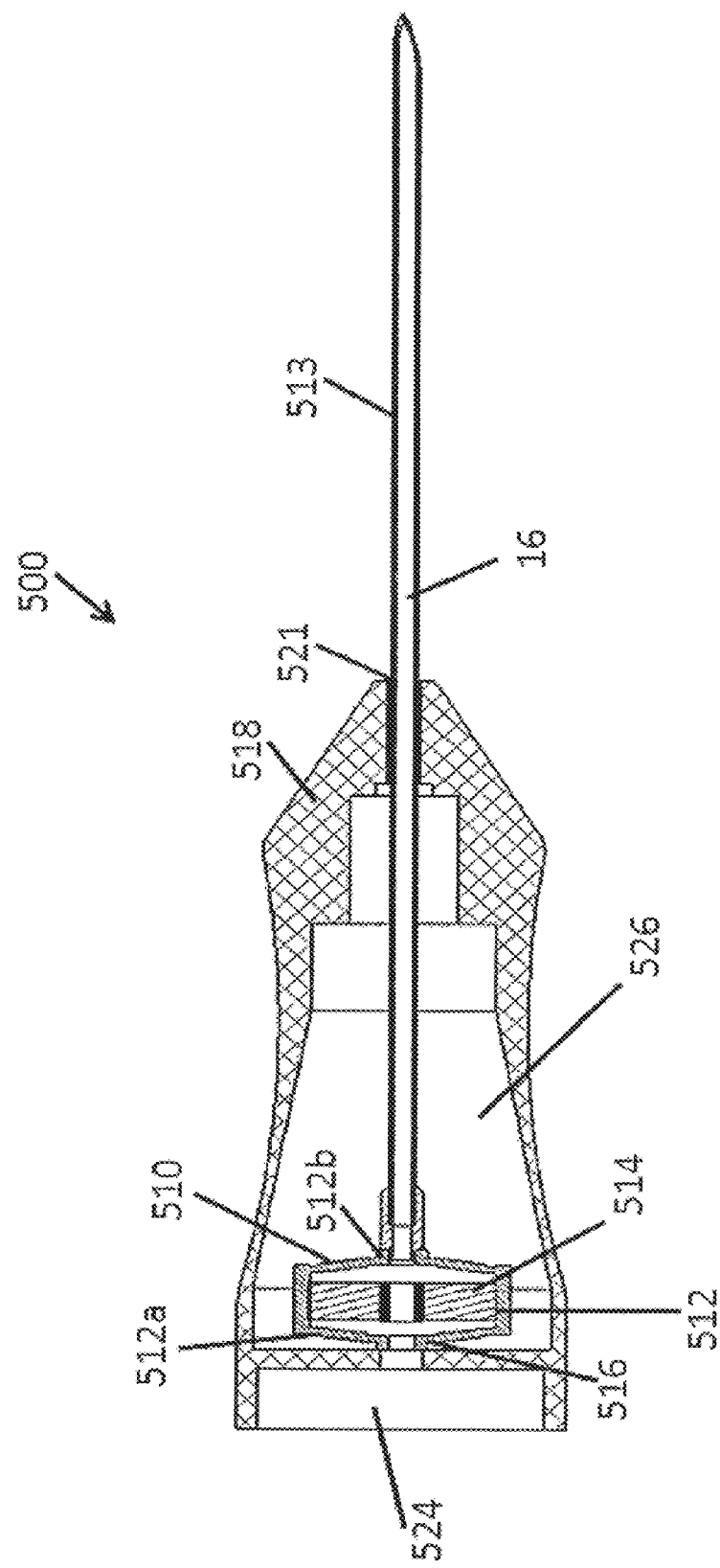

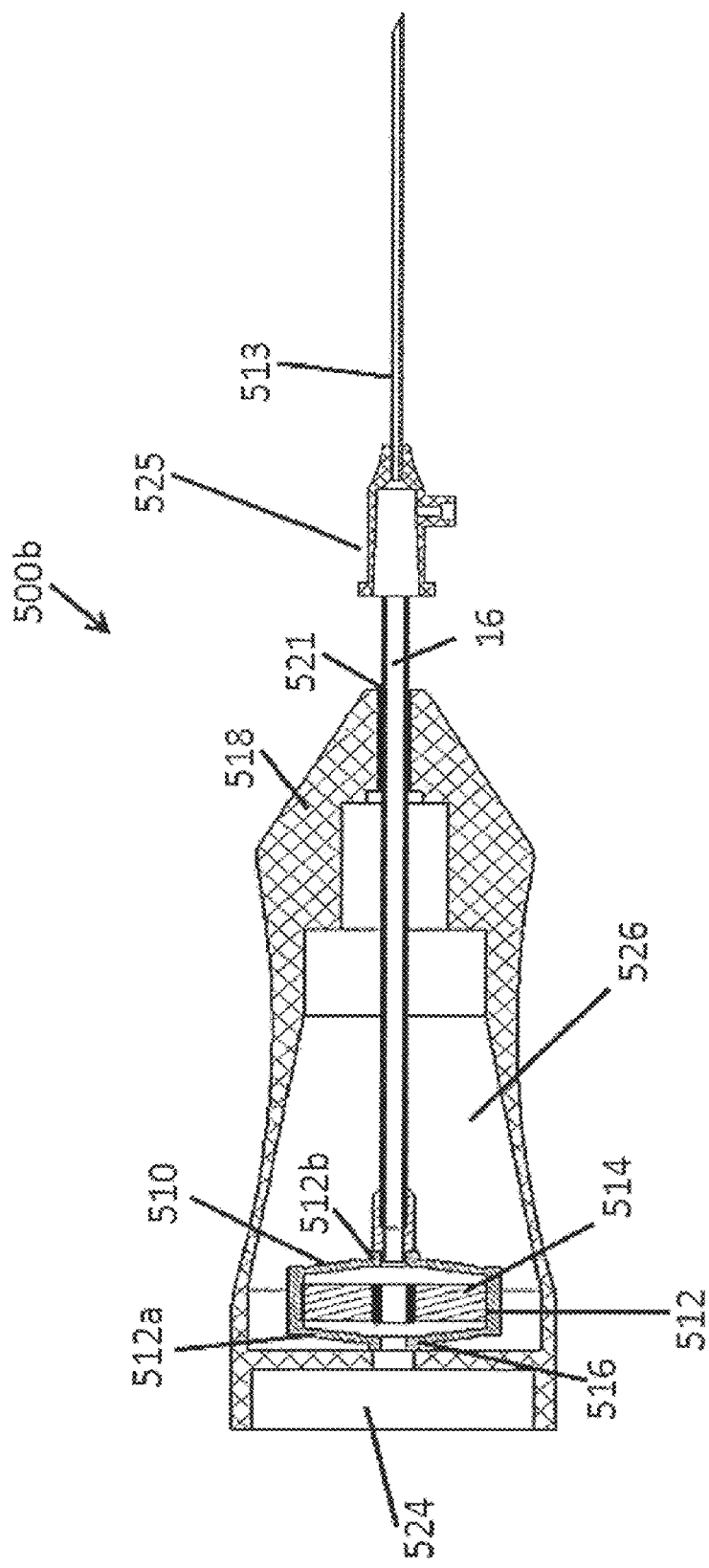

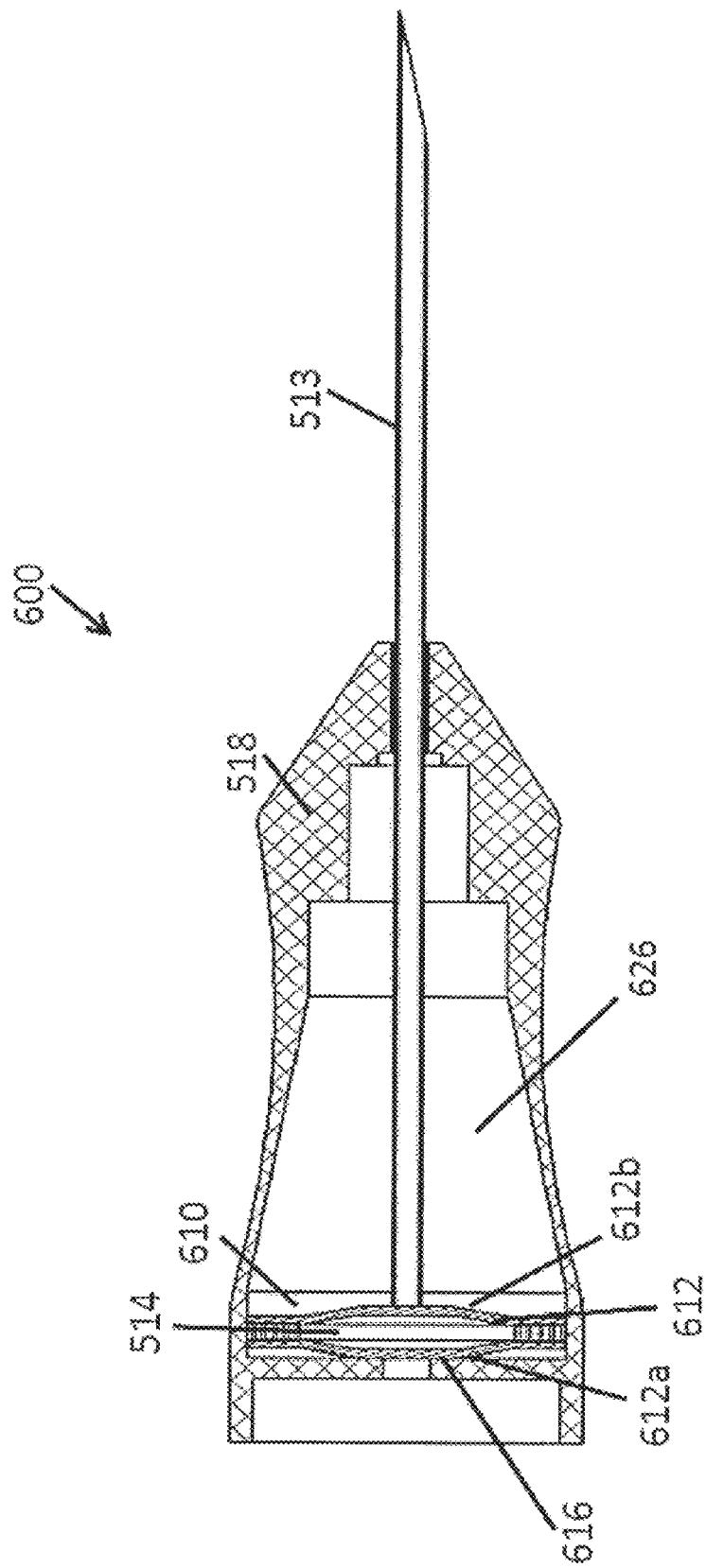

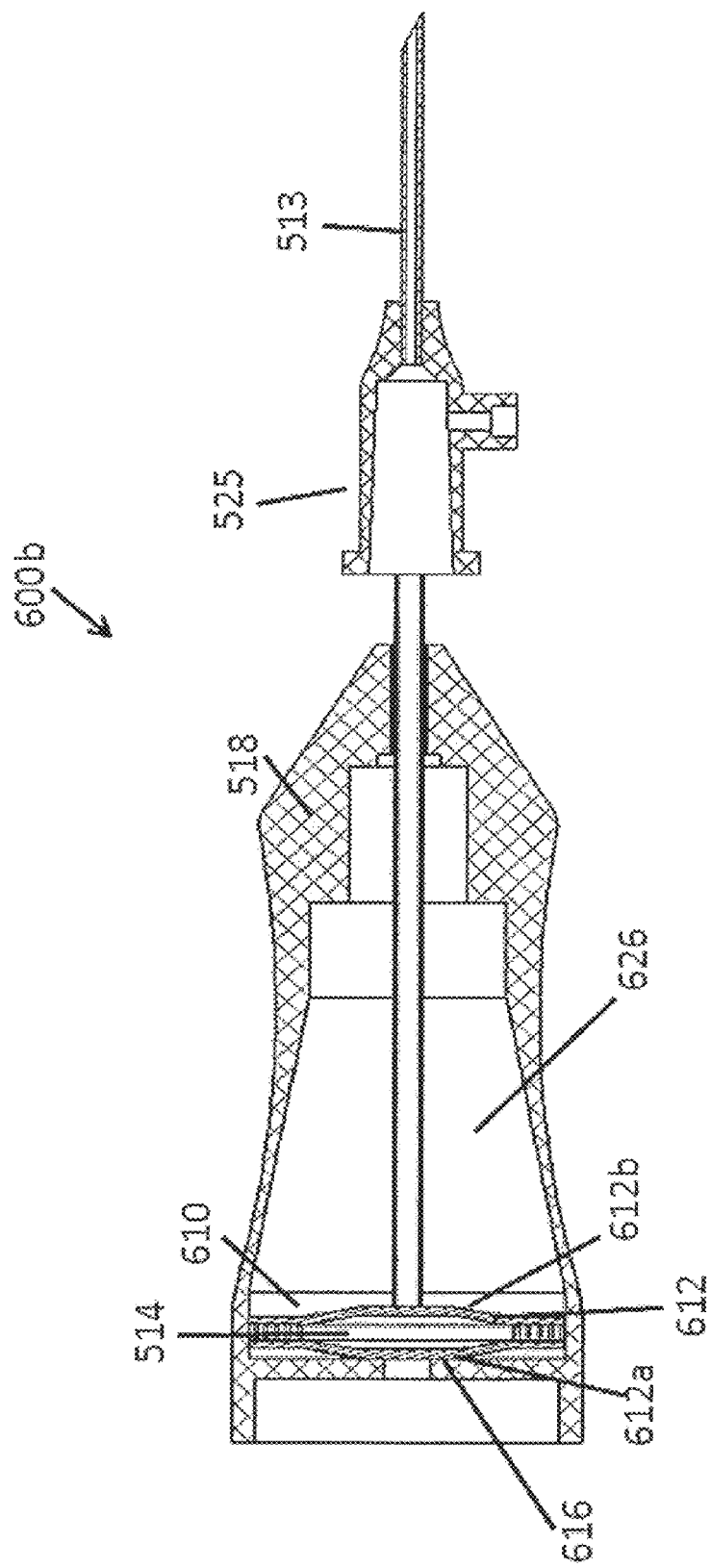

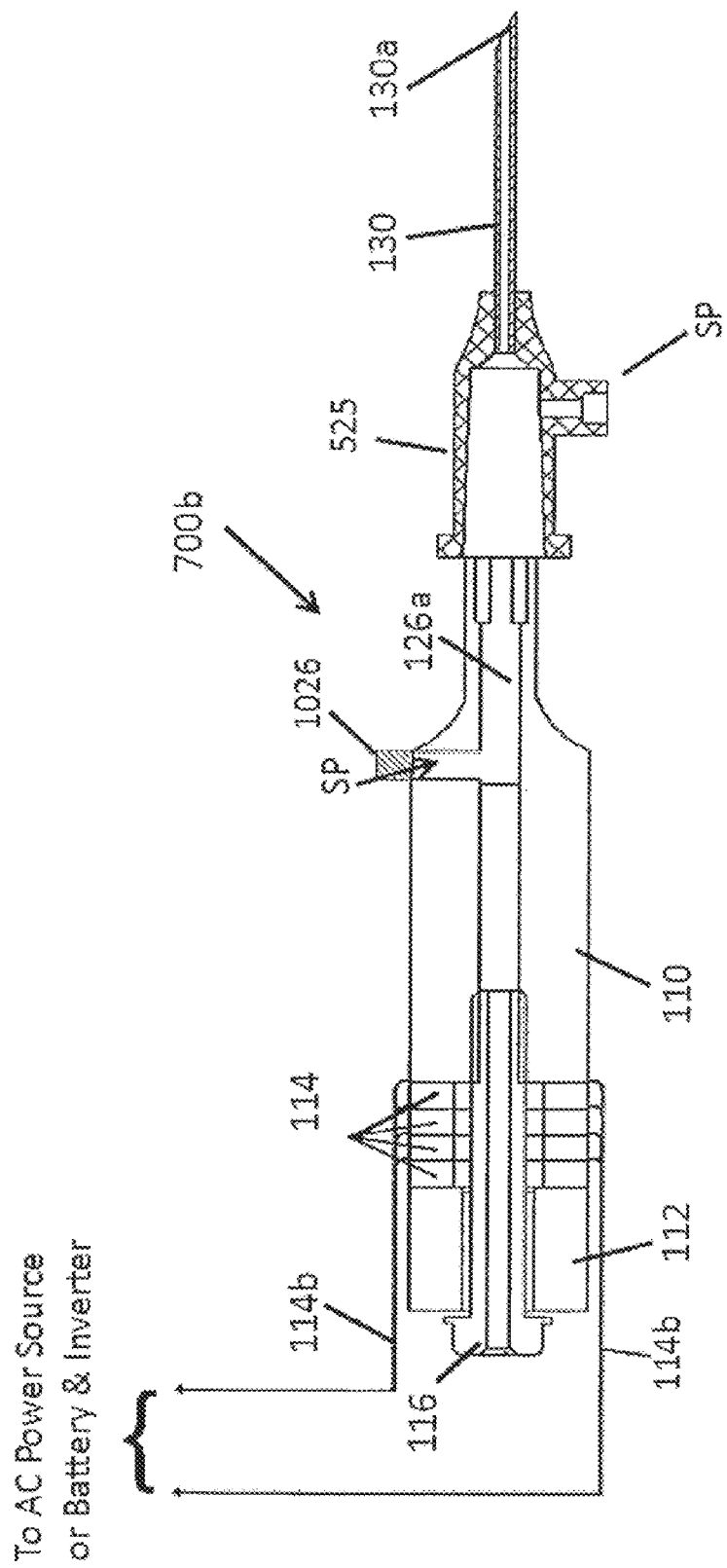

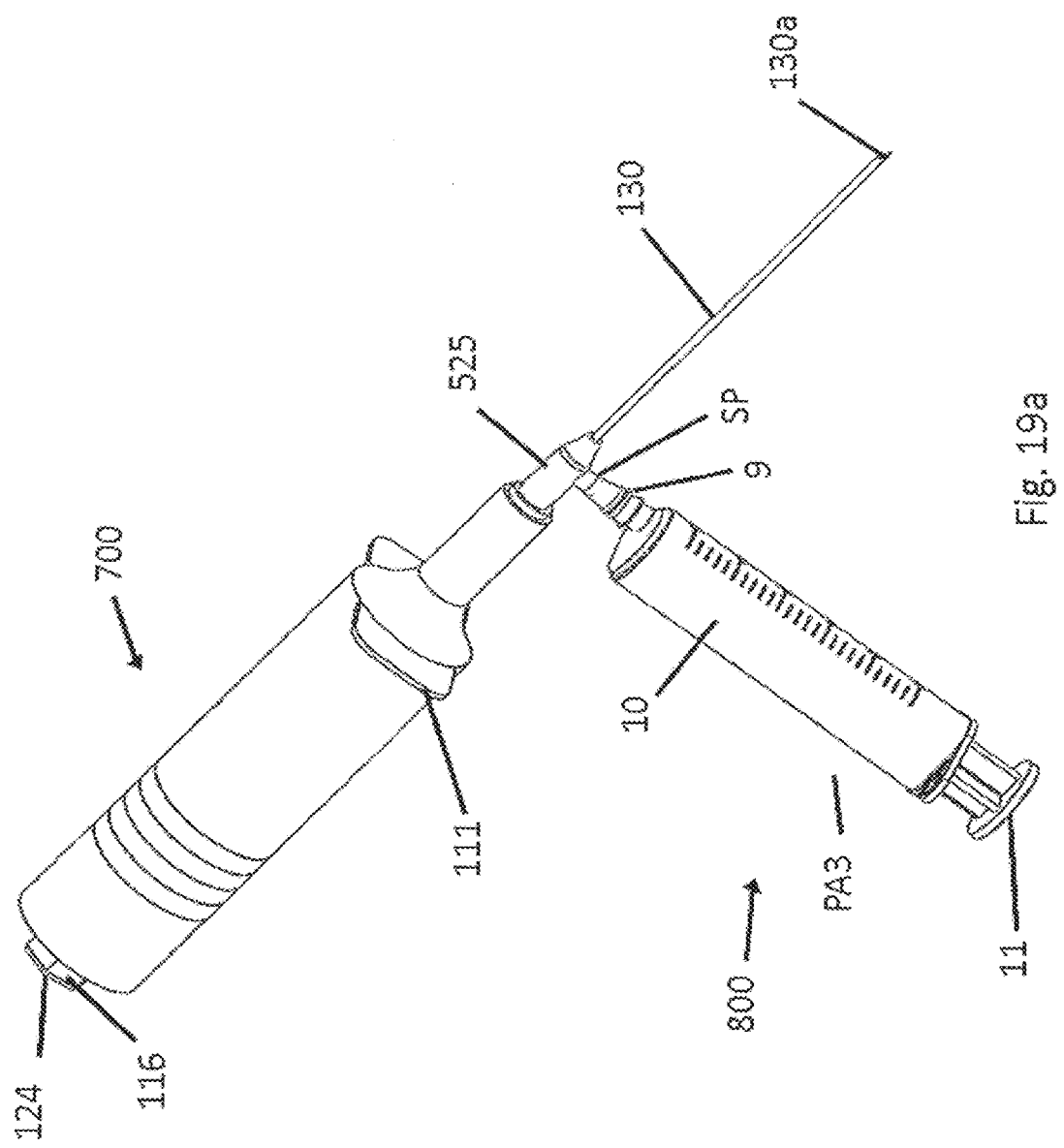

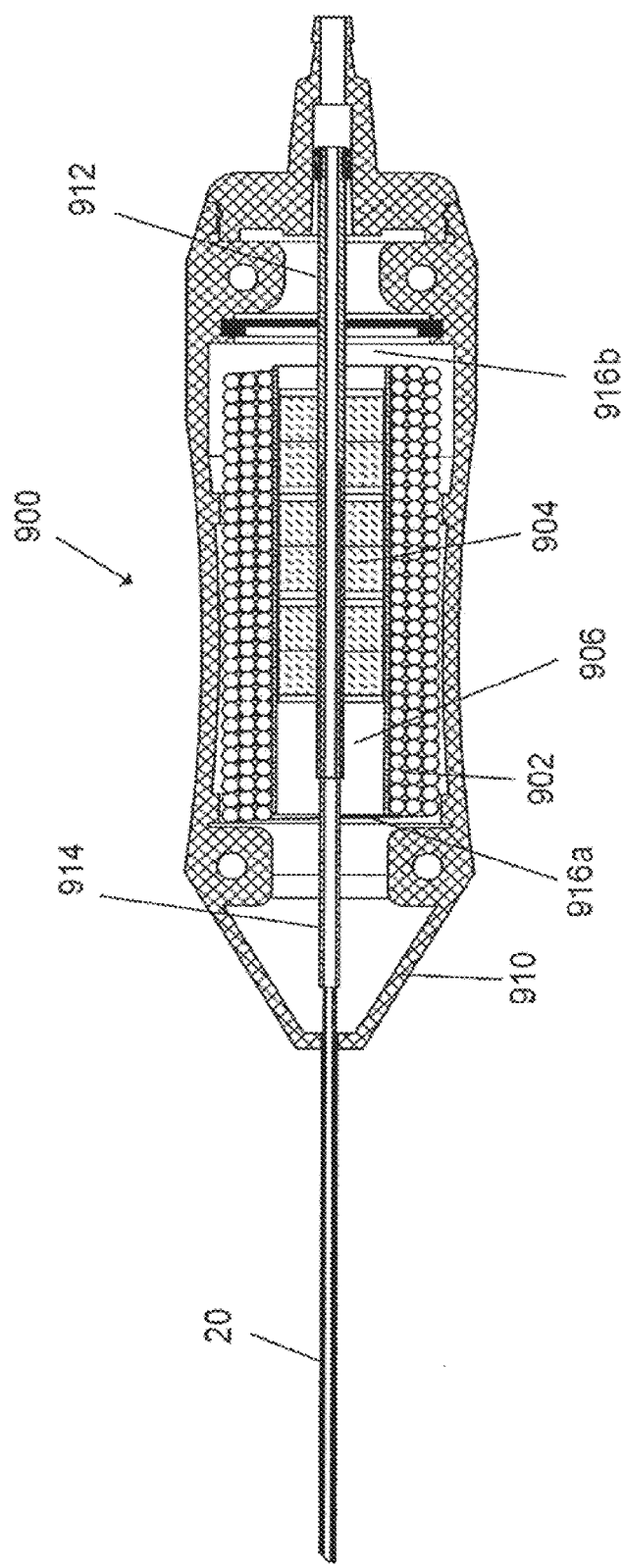

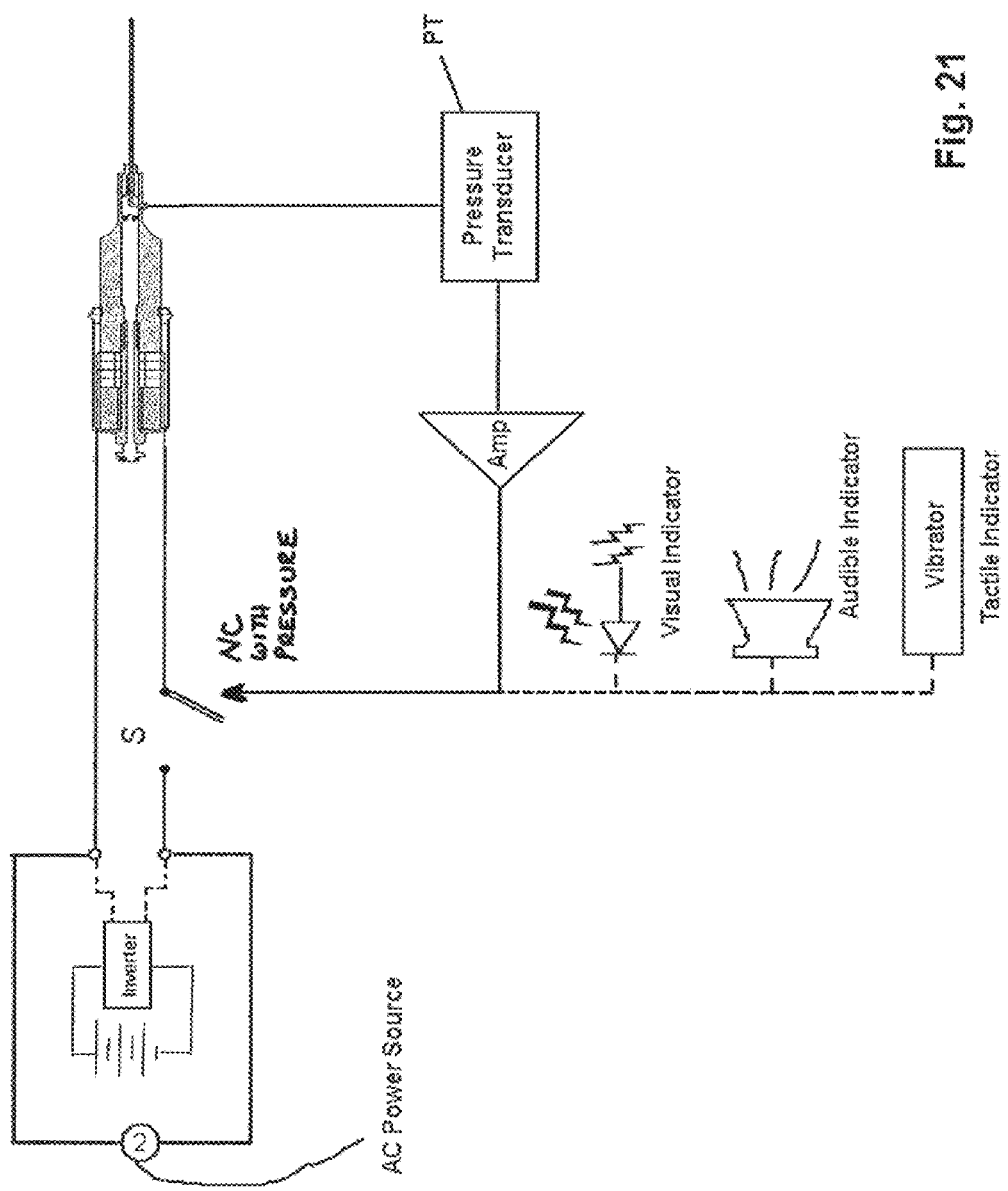

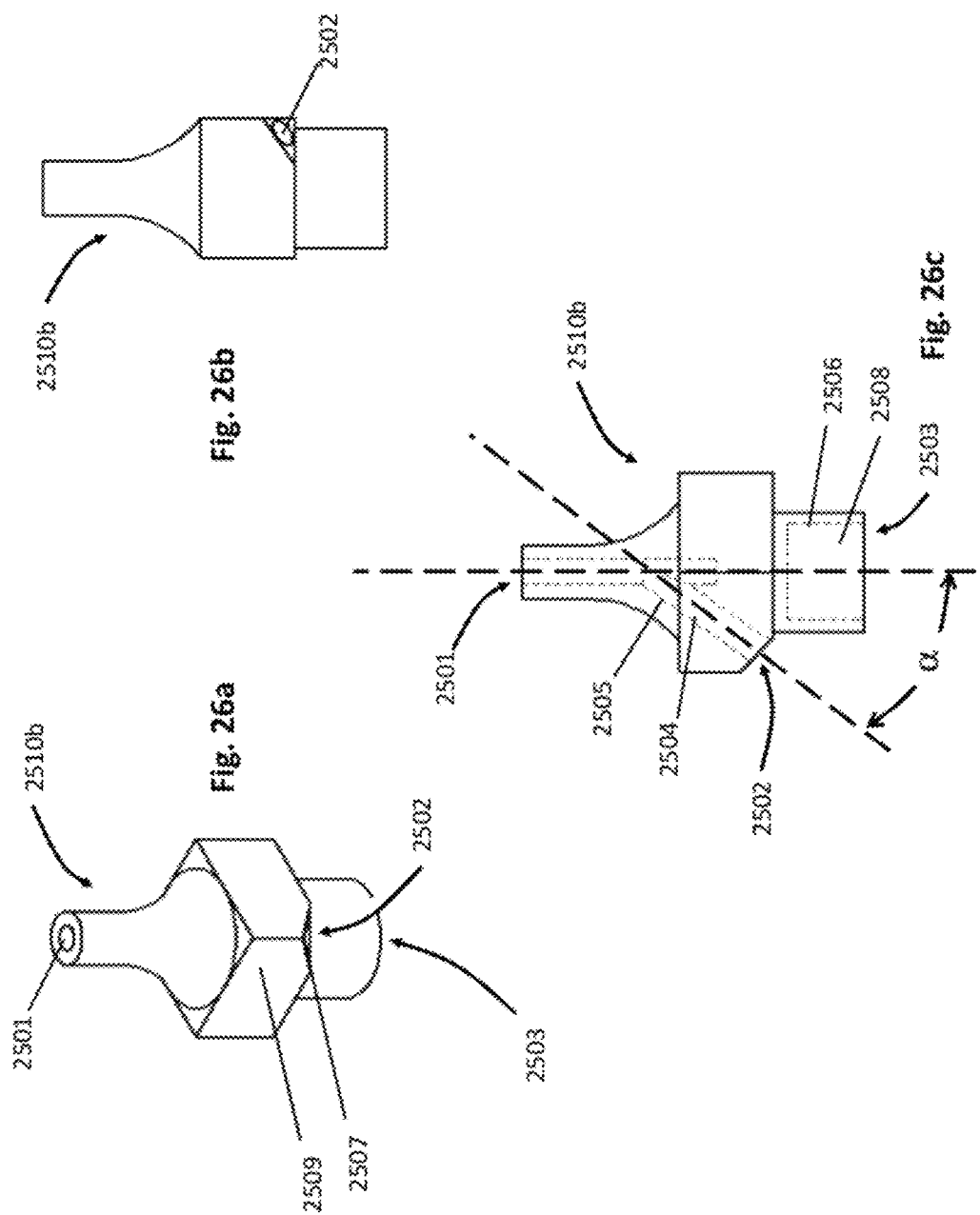

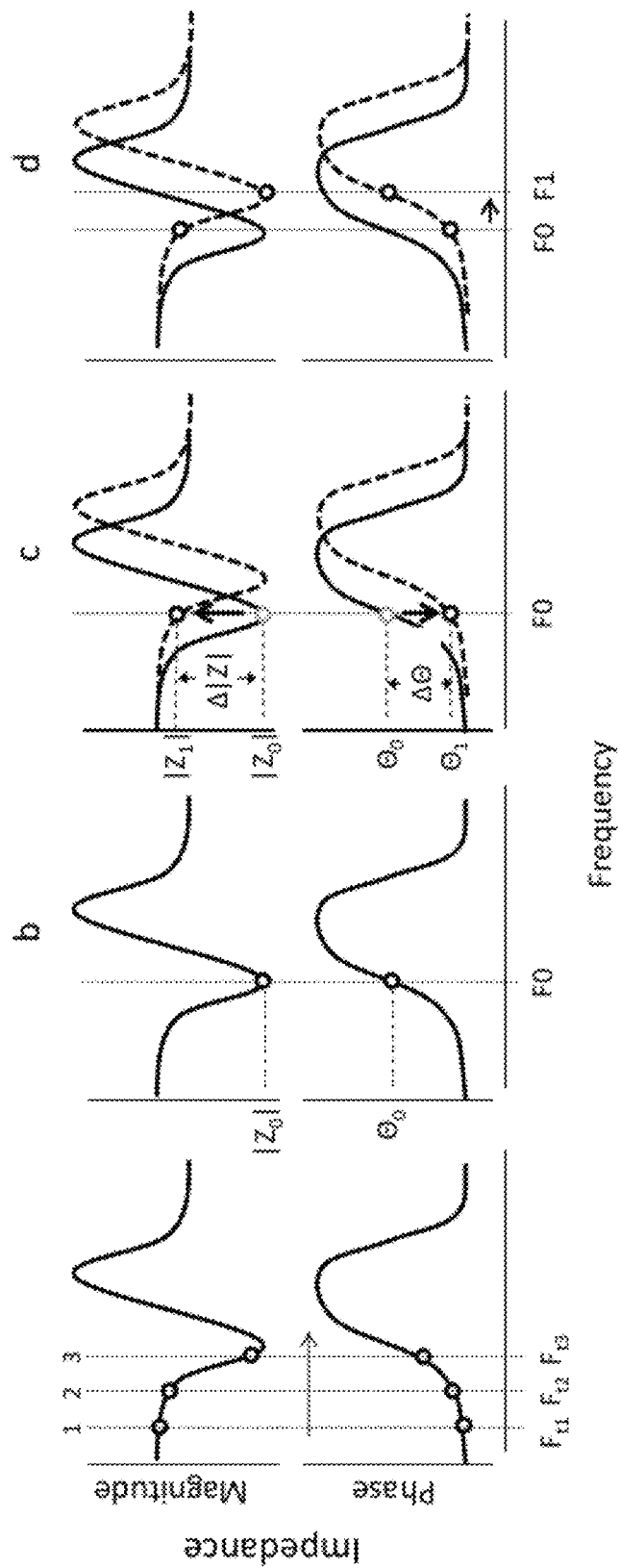

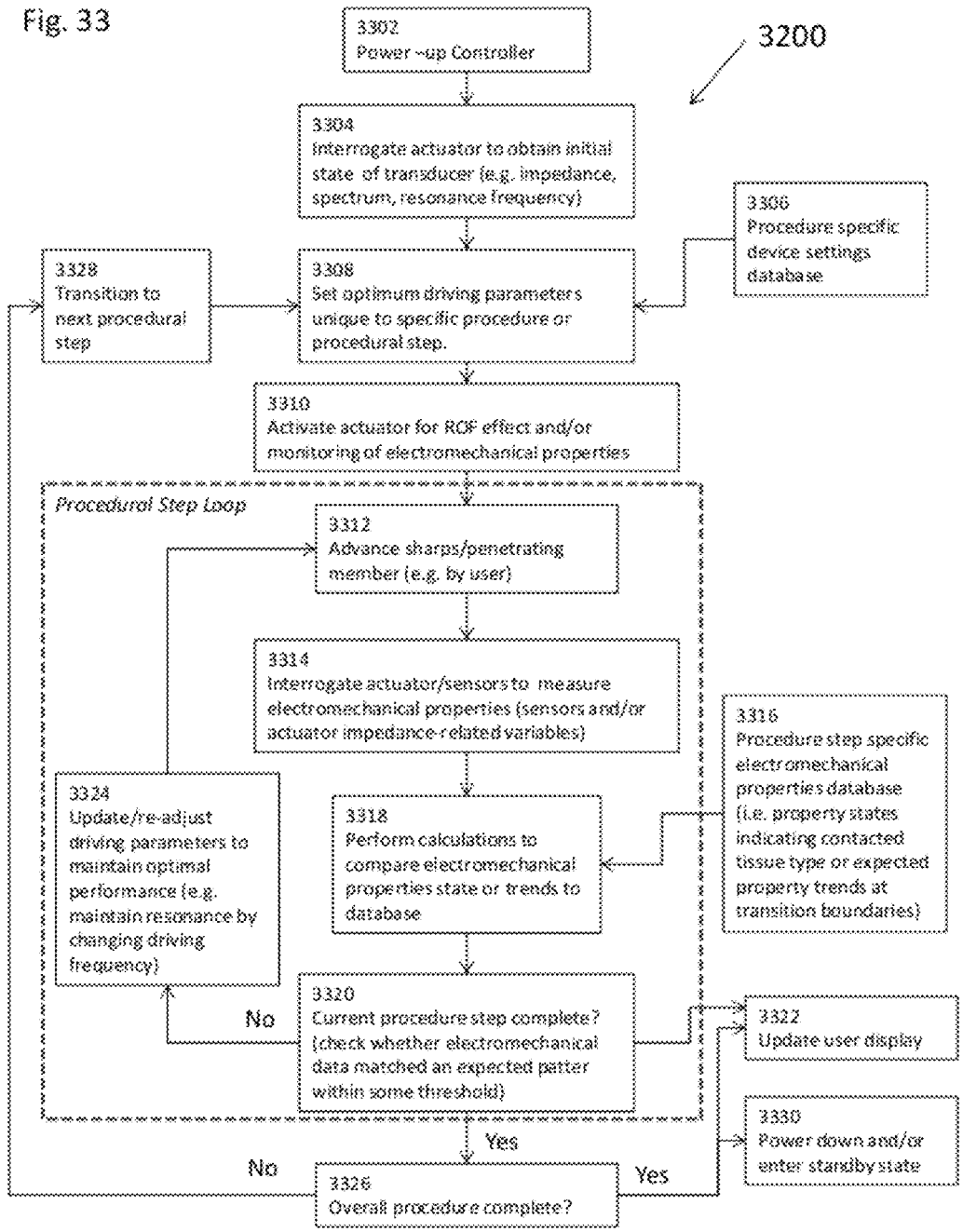

MEDICAL TOOL WITH ELECTROMECHANICAL CONTROL AND FEEDBACK

CROSS-REFERENCE TO RELATED APPLICATIONS

This non-provisional Application claims the benefit under 35 U.S.C. §119(e) of Provisional Application Ser. No. 61/441,500 filed on Feb. 10, 2011 entitled TRANSDUCER, NEEDLE, FEEDBACK AND CONTROL DESIGN FOR REDUCED PENETRATION FORCE, and of Provisional Application Ser. No. 61/441,677 filed on Feb. 11, 2011 entitled MEDICAL TOOL FOR REDUCED PENETRATION FORCE WITH FEEDBACK MEANS USING ELECTROMECHANICAL PROPERTIES and also is a Continuation-in-Part application and claims the benefit under 35 U.S.C. §120 of application Ser. No. 12/559,383 filed on Sep. 14, 2009 entitled MEDICAL TOOL FOR REDUCED PENETRATION FORCE WITH FEEDBACK MEANS which in turn claims the benefit under 35 U.S.C. §120 of application Ser. No. 12/163,071 filed on Jun. 27, 2008 entitled MEDICAL TOOL FOR REDUCED PENETRATION FORCE which in turn claims the benefit under 35 U.S.C. §119(e) of Provisional Application Ser. No. 60/937,749 filed on Jun. 29, 2007 entitled RESONANCE DRIVEN VASCULAR ENTRY NEEDLE and all of whose entire disclosures are incorporated by reference herein.

GOVERNMENT SUPPORT STATEMENT

This invention was made with government support under contracts GM085844, RR024943, CA139774 and AG037214 awarded by the National Institutes of Health. The government has certain rights in the invention.

BACKGROUND OF THE INVENTION

1. Field of the Invention

The present invention generally pertains to handheld medical devices, and more specifically to electrically driven lancets; epidural catheter inserters; biopsy medical instruments, such as bone biopsy medical devices; vascular entry penetrating members, spinal access needles and other catheterization needles. The invention is applicable to the delivery and removal of blood, tissues, medicine, bone marrow, nutrients or other materials within the body.

2. Description of Related Art

Epidural anesthesia is a form of regional anesthesia involving injection of drugs directly into the epidural space. To begin the procedure, a needle is inserted from the outer layer of skin, through several layers of tissue and finally placed within the epidural space, through which a catheter is optionally passed. Local anesthetics are injected into the epidural space causing temporary loss of sensation and pain by blocking the transmission of pain signals through nerves in or near the spinal cord. The procedure can be unpleasant to the patient because of the high force levels required for the relatively dull epidural needle to penetrate the supraspinous ligament, interspinous ligament and ligamentum flavum. One complication is that a clinician will accidently overshoot and puncture the dura because of this high force of penetration and an almost-instantaneous change in resistance upon passing the needle into the epidural space (i.e., high forward momentum followed by instantaneous minimization of force). Upon puncturing the dura, the cerebrospinal fluid can leak into the epidural space causing the patient to experience severe post dural puncture headache, lasting from days to possibly years. Significant leakage can cause enough intracranial hypotension as to tear veins, cause subdural hematoma, and traction injuries to the cranial nerves resulting in tinnitus, hearing loss, dizziness, facial droop, or double vision.

A bone marrow biopsy is used for diagnosing tumors and a variety of bone diseases. The most commonly used site for the bone biopsy is the anterior iliac crest. A major disadvantage is the force required to penetrate the bone tissue, and the twisting motion often used to force the needle inward, which results in patient discomfort as well as possible healing complications from damaged tissues. The penetration force can also be tiring for clinicians and lead to multiple sampling attempts. Complications are rare but can include bleeding, pain, and infection. Pain is minimized with proper local anesthesia, though the patient still experiences a pressure sensation during insertion and retraction during some procedures. Another problem is crushing the sample or being unable to retrieve part of all of it, limiting the ability to diagnose. As shown in FIG. 1, a biopsy tool PA1 typically comprises a handle (not shown) and hollow cannula 1 with cannula distal end 1' surrounding a stylet 2 attached to the handle. To penetrate through cortical bone, a clinician pushes the cannula and stylet through the bone to the marrow. The distal tip 3 of the inner stylet or trocar is sharpened and has an angled chisel-like face 4 which reduces the surface area to reduce the exertion force.

Currently, to minimize the possibility of a dura puncture, the epidural catheter insertion process is typically performed very slowly and with a 16-18 gauge, specially designed, relatively dull needle PA2, such as the one shown in FIG. 2 called a Tuohy needle 5. An epidural needle, such as the Tuohy needle 5 or Hustead needle, has a directional curved tip 6, which decreases the "sharpness" at the needle and, therefore, makes accidental dura puncture more difficult. The curved tip also facilitates directing an indwelling catheter into the epidural space and a tip opening 7 facilitates catheter or fluid introduction or removal. Unfortunately, this dull curved-tip design actually increases the force a clinician must use and makes it more difficult for a clinician to stop the forward momentum upon penetration of the dural space. Additionally, the Tuohy design increases the likelihood that a clinician relies on tactile feedback during penetration. In other words, during the insertion procedure a clinician will rely on feeling a "popping" sensation—indicative of passing the needle past the ligamentum flavum—to locate the tip of the needle within the epidural space and quickly stop the forward momentum being applied. Still, because penetration into other tissues, such as muscle, calcified ligament, or regular ligament may produce a similar popping, a clinician may not fully perceive the correct location of the needle tip where the tip of the needle is occluded until passing through these tissues.

Several alternate technologies have been developed that attempt to minimize the dura puncture risk, while also giving the clinician indication of successful epidural placement. For example, the detection method and apparatus disclosed in U.S. Patent Application Publication No. 2007/0142766 (Sundar, et al.), the contents of which are incorporated by reference, relies on a spring-loaded plunger pushing a fluid into the epidural space upon successful entry. Accordingly, the clinician is given a visual indicator (i.e., the movement of the plunger as the fluid experiences a loss of resistance at the needle opening), and would cease applying forward force. Similarly, U.S. Pat. No. 5,681,283 (Brownfield) also relies on a visual indicator to communicate successful entry of a needle into a cavity to the clinician. Unfortunately, while a visual indicator is a positive advancement, the actual cause of the accidental dural wall puncture—that is, the high force applied by the clinician against the needle to pass through the various tissue layers and then stop—is not taught or suggested.

Therefore, there exists a need for a tool that reduces the puncture force of a needle, such as a Tuohy needle, and enables a clinician to perform a more controlled entry into the epidural space, thereby reducing the possibility of an accidental dura puncture.

While accidental dura puncture is a concern, simply locating the epidural space may pose a challenge even to the most skilled physicians. Therefore, when a needle such as a Tuohy needle is passed through the ligamentum flavum and into the epidural space, it is helpful for a clinician to receive immediate feedback indicating successful penetration and the location of the tip of the needle. A basic conventional feedback device such as the one in FIG. 2a comprises a needle (not shown) attached to a syringe PA3 at a front portion 9, and wherein the syringe PA3 is formed of a tubular body 10 and houses a biasing element 11 comprising a stem acting as a biasing element. To provide feedback indicating successful epidural penetration the device relies on a biasing force acting against the biasing element 11 which then acts upon a fluid, such as saline or air within the syringe. Essentially, in this hydraulic feedback method, as the biasing force acts upon the fluid, the fluid translates this pressure to an opening of the needle tip. An opposing force, acting on the needle tip as it is held against a tissue such as the ligamentum flavum, acts to prevent the fluid from being released from the syringe. Typically, a clinician's thumbs act as the biasing force source which in turn acts upon the plunger stem. The clinician's thumbs serve to "feel" the hydraulic resistance exerted on the fluid by the opposing tissue force. Upon entering the epidural space, however, the opposing pressure of tissue acting against the tip is removed, and a pressure drop allows the biasing force to move solution out of the syringe through the needle tip. The clinician becomes aware of successful penetration of the epidural space due to his/her thumbs "feeling" the sudden pressure drop or loss of resistance at the plunger stem. Also, the clinician may receive visual indication of successful penetration by witnessing the plunger advancing through the syringe externally as the fluid is released into the epidural space in the patient. One problem with this conventional device and method is that it is difficult for a clinician to both apply a biasing force on the plunger while also applying an advancing force against the syringe body in order to advance the needle through the ligamentum flavum. Moreover, to prevent accidental dura puncture, clinicians tend to hold the conventional syringe in such a way as to hold the patient steady, while applying a forward momentum against the syringe, and while applying a biasing force against the plunger stem. This is both awkward and uncomfortable to the clinician and patient.

Some advancements have also attempted to provide an automatic biasing element to act against the plunger of an epidural syringe while also providing visual indication or feedback, rather than tactile response, of successful puncture of various internal target areas in the human body. For example, in U.S. Patent Publication No. 2007/0142766 (Sundar et al.), a spring is utilized to act with a biasing force against the syringe plunger. When the epidural needle attached to the syringe passes through into the dural space, the pressure drop allows the spring to bias the plunger. As the plunger moves, the stem provides at least some visual indication as it moves with the plunger. Similarly, U.S. Pat. No. 5,024,662 (Menes et al.), which is hereby incorporated by reference, provides visual indication by utilizing an elastomer band to provide the biasing force against the plunger stem. In U.S. Pat. No. 4,623,335 (Jackson) which is hereby incorporated by reference, an alternative device assists in visually indicating a pressure to identify the location of the needle tip. In addition, U.S. Pat. No. 7,297,131 (Call) which is hereby incorporated by reference, uses a pressure transducer to translate a pressure change into an electronic signal. The electronic signal is then converted to a visual display indicator, for example by activating a light emitting diode to emit.

Therefore, a need exists to overcome the challenges not addressed by conventionally available technologies that reduces the force necessary for penetration of a sharp medical element of a medical device through tissue and also has the ability to deliver (e.g., deliver saline solution, or drugs, etc.) or retrieve materials subcutaneously (e.g., bone biopsy, etc.).

A need also exists to provide visual, tactile, electrical or additional indication to a clinician that the penetrating member has successfully penetrated the specific body space such as the epidural space, especially when the force to enter such a space has been substantially reduced. And this same force reduction must be either controlled or shut off immediately upon entry into the epidural space to avoid (easier) penetration of the dura.

Specifically, a need exists in the medical device art for an improved medical device having a penetrating element that is vibrated at a frequency that thereby reduces the force required to penetrate tissue, reduces the amount of resulting tissue damage and scarring, improving body space or vessel access success rate, minimizes introduction wound site trauma and, most importantly, improves patient comfort while minimizing potential complications.

A need exists for a clinician to be able to use less force to penetrate hard tissue such as the cortical bone during bone biopsy, which would reduce clinician fatigue, patient discomfort, and tissue damage while improving the sampling success rate and quality. There is a need to sense proper location, stop forward motion and collect the sample. There is a further need to turn device on after collection and to reduce force and patient discomfort as the penetrating member is being retracted from the body.

There is also a need for spinal access procedures where a clinician would want a reduction of force as well as to know the location of the needle tip but applied to a relatively-sharp penetrating member, such as a pencil point tip, as the clinician does not want to core tissue.

There is also a need for performing nerve block procedures where a clinician would want a reduction of force as well as to know the location of the needle tip. And this same force reduction must be either controlled or shut off immediately upon entry into the desired location.

All references cited herein are incorporated herein by reference in their entireties.

SUMMARY OF THE INVENTION

The basis of the invention is a handheld medical device, (e.g., epidural needle, bone biopsy device, spinal needle, regional block needle, catheter introducer needle, etc.) having a penetrating member (e.g., an introducer needle, Tuohy needle, pencil point tipped needle, trocar needle (e.g., JAMSHIDI® biopsy needle), etc.), at a distal end, for use in procedures, (e.g., vascular entry and catheterization, single shot or continuous epidurals, spinal access, regional blocks, or bone biopsy, etc.), wherein the medical device comprises at least one driving actuator, (e.g., a piezoelectric, voice coil, solenoid, pneumatic, fluidic or any oscillatory or translational actuator etc.) attached to the penetrating member (e.g., at a proximal end of the penetrating member), and wherein the driving actuator translates the penetrating member, causing it to reciprocate at small displacements, thereby reducing the force required to penetrate through tissues.

Additionally, the invention comprises a means for providing feedback, either visually, audibly, or by tactile response, using a variety of detection mechanisms (such as, but not limited to, electrical, magnetic, pressure, capacitive, inductive, etc. means), to indicate successful penetration of various tissues, or of voids within the body such as the epidural space so that the clinician knows when to stop as well as to limit power to the driving mechanism.

Actuator technologies that rely on conventional, single or stacked piezoelectric material assemblies for actuation are hindered by the maximum strain limit of the piezoelectric materials themselves. Because the maximum strain limit of conventional piezoelectric materials is about 0.1% for polycrystalline piezoelectric materials, such as lead zirconate titanate (PZT) polycrystalline (also referred to as ceramic) materials and 0.5% for single crystal piezoelectric materials, it would require a large stack of cells to approach useful displacement or actuation of, for example, a handheld medical device usable for processes penetrating through tissues. However, using a large stack of cells to actuate components of a handpiece would also require that the tool size be increased beyond usable biometric design for handheld instruments.

Flextensional actuator assembly designs have been developed which provide amplification in piezoelectric material stack strain displacement. The flextensional designs comprise a piezoelectric material driving cell disposed within a frame, platen, endcaps or housing. The geometry of the frame, platten, endcaps or housing provides amplification of the axial or longitudinal motions of the driver cell to obtain a larger displacement of the flextensional assembly in a particular direction. Essentially, the flextensional actuator assembly more efficiently converts strain in one direction into movement (or force) in a second direction. Flextensional piezoelectric actuators may be considered mid-frequency actuators, e.g., 25-35 kHz. Flextensional actuators may take on several embodiments. For example, in one embodiment, flextensional actuators are of the Cymbal type, as described in U.S. Pat. No. 5,729,077 (Newnham), which is hereby incorporated by reference. In another embodiment, flextensional actuators are of the amplified piezoelectric actuator ("APA") type as described in U.S. Pat. No. 6,465,936 (Knowles), which is hereby incorporated by reference. In yet another embodiment, the actuator is a Langevin or bolted dumbbell-type actuator, similar to, but not limited to that which is disclosed in U.S. Patent Application Publication No. 2007/0063618 A1 (Bromfield), which is hereby incorporated by reference.

In a preferred embodiment, the present invention comprises a handheld device including a body, a flextensional actuator disposed within said body and a penetrating or "sharps" member attached to one face of the flextensional actuator. In the broadest scope of the invention, the penetrating member may be hollow or solid. The actuator may have an internal bore running from a distal end to a proximal end or may have a side port located on the penetrating member attachment fitting. Therefore for single use penetrating members there is no need to sterilize the penetrating member after use. Where the penetrating member is hollow, it forms a hollow tubular structure having a sharpened distal end. The hollow central portion of the penetrating member is concentric to the internal bore of the actuator, together forming a continuous hollow cavity from a distal end of the actuator body to a proximal end of the penetrating member. For example, the flextensional actuator assembly may utilize flextensional Cymbal actuator technology or amplified piezoelectric actuator (APA) technology. The flextensional actuator assembly provides for improved amplification and improved performance, which are above that of a conventional handheld device. For example, the amplification may be improved by up to about 50-fold. Additionally, the flextensional actuator assembly enables handpiece configurations to have a more simplified design and a smaller format.

One embodiment of the present invention is a resonance driven vascular entry needle to reduce insertion force of the penetrating member and to reduce rolling or collapsing of vasculature.

An alternative embodiment of the present invention is a reduction of force epidural needle that provides the clinician a more controlled entry into the epidural space, minimizing the accidental puncturing of the dural sheath. In this embodiment, an actuator, for example, a Langevin actuator (more commonly referred to as a Langevin transducer), has a hollow penetrating member, for example a hollow needle, attached to a distal portion of the actuator. The Langevin actuator in this embodiment may be open at opposite ends. The openings include a hollow portion extending continuously from the distal end of the actuator to a proximal end of the actuator. The distal opening coincides with the hollow penetrating member. A plunger, having a handle, a shaft and a seal is also attached to the actuator at an opposite end of the sharps member. The plunger's shaft is slidably disposed within the continuous, hollowed inner portion of the actuator. The seal is attached to a distal portion of the plunger's shaft and separates a distal volume of the hollowed inner portion of the actuator from a proximal volume of the hollowed inner portion. Because the plunger's shaft is slidably disposed, the plunger is also slidably disposed and, in response to a motion of the shaft in a distal direction, reduces the distal volume of the hollowed inner portion and increases the proximal volume. Conversely, in response to a motion of the shaft in a proximal direction, the seal also moves in a proximal direction, thereby reducing the proximal volume of the hollowed portion and increasing the distal volume. The motion of the plunger's shaft, and, effectively, the plunger's seal, is actuated by an external force acting on the plunger's handle. When electrically activated, the actuator transfers compression and expansion of the piezoelectric material portion to a hollow and penetrating tip of the hollow needle. Langevin actuators may be considered high frequency actuators, e.g., >50 kHz.

Another embodiment of the invention provides a bone marrow biopsy device having an outer casing, an actuator, for example, a Langevin actuator (e.g., see, for example, U.S. Pat. No. 6,491,708 (Madan, et al.), whose entire disclosure is incorporated by reference herein), including a first body portion and a second body portion of the actuator, with piezoelectric material formed between the first and second body portions, wherein the actuator is disposed at least partially within the casing. The invention further includes a handle, an outer cannula, such as a needle, having an open distal end and an open proximal end with the cannula positioned at a distal portion of the actuator. In one aspect of the present embodiment, the invention further comprises a stylet having a penetrating distal tip attached to the handle at a portion opposite the distal tip, wherein the stylet is slidably disposed through a center cavity of the body and cannula. The actuator is formed with a distal opening formed at a distal end of the actuator, and a proximal opening formed at a proximal end of the actuator with a centralized hollow bore extending from the distal opening to the proximal opening, thereby defining a hollow channel.

More precisely, the outer cannula is a hollow tube fixedly attached at the distal end of the actuator such that the open proximal end of the cannula coincides with the distal opening of the actuator distal end. The stylet is slidably and centrally disposed within the actuator from the proximal end through the hollow channel and through the distal end. The stylet is also of predetermined length such that it is slidably and centrally located through the outer cannula, with the distal tip of the stylet protruding past the open distal end of the cannula.

The various actuators of the present invention must be connected electrically to an external electrical signal source. Upon excitation by the electrical signal, the actuators convert the signal into mechanical energy that results in vibratory motion of an end-effector, such as an attached needle or stylet. In the case of a Langevin actuator, the vibratory motion produced by the piezoelectric materials generates a standing wave through the whole assembly such as that in graph in FIG. 17. Because at a given frequency, a standing wave is comprised of locations of zero-displacement (node, or zero node) and maximum displacement (anti-node—not shown) in a continuous manner, the displacement that results at any point along the actuator depends on the location where the displacement is to be measured. Therefore, the horn is typically designed with such a length so as to provide the distal end of the horn at an anti-node when the device is operated. In this way, the distal end of the horn experiences a large vibratory displacement in a longitudinal direction with respect to the long axis of the actuator. Conversely, the zero node points are locations best suited for adding port openings or slots so as to make it possible to attach external devices to the actuator. As indicated by line ZN, the port opening SP coincides with the zero node location and the smaller displacement at zero node points are less abrasive to an attached device.

Accordingly, an alternative embodiment, the actuator may be formed with a distal opening formed at the distal end of the actuator, a port opening on at least a portion of the actuator, and a hollow bore extending from the distal opening to and in communication with the port opening. Preferably, the port opening may be a side port on a horn side of the actuator. More preferably, the port opening is generally located (preferably centered) at a zero node location of the actuator, and most preferably centered at a zero node location on a horn side of the actuator. Additionally, a means for providing feedback, for example any of those conventional feedback devices disclosed above used for indication of successful body location such as the epidural space penetration is in communication with the present embodiment by attachment at the port opening location, or preferably at the side port. Alternatively, any means capable of delivering fluid, such as a catheter tube or conventional syringe can be attached at the port opening location, or preferably at the side port.

The present invention relates generally to oscillatory or translational actuated handheld device for penetration through various tissues within a body for the delivery or removal of bodily fluids, tissues, nutrients, medicines, therapies, placement or removal of catheters, etc. For example for piezoelectric devices, the present invention is a handpiece including a body, at least one piezoelectric element disposed within the body, and a sharps member for tissue penetration, such as a syringe, epidural needle or biopsy needle located at a distal portion of the handheld device, having a feedback means capable of indicating successful penetration of the body space, such as epidural space by providing visual, audible or tactile indications using any well-known detection mechanisms such as but not limited to electrical, magnetic, pressure, capacitive, inductive, etc. means.

Additionally, with the use of proper circuitry the handheld medical device comprising an actuator is provided with a means for shutting off external power to the driving actuator (e.g., one or more of piezoelectric elements, voice coil, solenoid, other oscillatory or translational actuator, etc.) upon penetration of a particular tissue or internal portion of a body such as the epidural space. The means for shutting off external power to the driving actuator may be implemented as part of the aforementioned means for providing visual, audible or tactile indications or may be a separate means altogether. Preferably the means for shutting off external power to the driving actuator upon penetration of a particular tissue or internal portion of for example, the epidural space, may be accomplished by incorporating proper circuit configurations to aforementioned electrical means to trigger a switching means in order to cut off power to the driving actuator. Such a means is described in U.S. Pat. No. 5,575,789 (Bell et al.) whose entire disclosure is incorporated by reference herein. By providing such electrical cut-off means, upon successfully penetrating the epidural space for example, a clinician receives one or more of a visual, audible, and tactile indications as well as a loss of power to the device as a secondary indication that a particular internal portion of a body has been penetrated. Furthermore, with a loss of power to the device by cutting off electrical power to the driving actuator, the force or forward momentum necessary for further penetration of tissue will cease and in turn, will decrease the potential for unwanted body area puncture such as accidental dural puncture.

Additionally the invention with specific control electronics will provide reduction of force as the penetrating member is retracted from the body.

In one embodiment, the penetrating or sharp tubular member is a part of a vascular entry needle.

In another embodiment, the penetrating sharp tubular member is a Tuohy needle.

In yet another embodiment, the penetrating or sharp tubular member is a trocar and stylet assembly, such as a JAMSHIDI® biopsy needle.

In yet another embodiment, the penetrating or sharp tubular member is a pencil point tipped needle.

In yet another embodiment, the penetrating or sharp tubular member is part of a trocar access port.

In an embodiment, a medical device for penetrating living being tissue is provided. The device can include a driving actuator for converting electrical energy into reciprocating motion when energized. The driving actuator can include a distal end and a first channel extending to the distal end, and a penetrating member can be coupled to the distal end of the driving actuator. The medical device can include a feedback subsystem that detects any change of electromechanical properties related to the operation of the penetrating member for: (i) indicating to an apparatus operator a different type of tissue has been contacted by said penetrating member; and/or (ii) automatically controlling force being applied to said penetrating member.

In an embodiment, a method for reducing the force needed to penetrate living being tissue based on the tissue being encountered during the insertion of a sharps member is provided. The method can include the step of establishing characteristic electromechanical property changes of a vibrating reference member having a sharps member that passes through various tissues that correlates said changes with particular tissues. The method can include reciprocating the sharps member against the living being tissue using a reciprocating actuator that converts electrical energy to reciprocating motion. The method can include detecting a change in said characteristic electromechanical property. The method can include the step of comparing said detected change against said correlation and indicating to an operator of said cutting member the type of tissue that is being currently encountered based on the change in said characteristic electromechanical property. The method can include the step of comparing said detected change against said correlation and for automatically controlling the force being applied to said sharps member In an embodiment, a device is provided. The device can include an actuator. The actuator can include a displaceable member formed of a first portion detachably connected to a second portion, a rear mass, and a piezoelectric stack formed between the displaceable member and rear mass. The device can include a sharps member coupled to a distal end of the second portion. The device can include an electrical power feedback subsystem for automatically controlling the power to the actuator based on a sensed condition.

In an embodiment, a method is provided. The method can include the step of providing power from a power source to an actuator of a medical device, the actuator configured to convert the provided power into reciprocating motion at a first frequency that is transferred to a sharps member coupled to the actuator. The method can include the step of detecting a reference resonance frequency of the medical device. The method can include automatically adjusting the power provided to the actuator to cause a actuator to vibrate at the reference resonance frequency.

These and other features of this invention are described in, or are apparent from, the following detailed description of various exemplary embodiments of this invention.

BRIEF DESCRIPTION OF THE DRAWINGS

Exemplary embodiments of this invention will be described with reference to the accompanying figures.

FIG. 3 is a graph illustrating the penetration force of a penetrating member;

FIG. 4 is a cross section of a Langevin actuator, more commonly referred to as a Langevin transducer, for use as an actuator in a first embodiment of the present invention;

FIG. 4a is needle design with the side port located in the penetrating member hub providing external access such as for pressure sensor connection or catheter entry location.

FIG. 6 is a cross section of a plunger used in a first embodiment of the invention;

FIG. 6a depicts the present invention including a sterilization sleeve for wires and housing;

FIG. 7 is a cross section of a first embodiment of the invention;

FIG. 7a is a cross-section of an alternate design of the first embodiment of the invention that incorporates the side port on the penetrating member hub.

FIG. 9 is an isometric view of a second embodiment of the present invention;

FIG. 9a is an isometric view of an alternate design of the second embodiment using a side port on the actuator for attachment location of the pressure sensor or entry of a catheter;

FIG. 9b is an isometric view of more preferred alternate design of the second embodiment using a side port on the penetrating member hub for attachment location of the pressure sensor or entry of a catheter;

FIG. 10a is a cross section of an inner stylet for use in a third embodiment of the present invention;

FIG. 10b is a cross section of an outer penetrating member, such as a trocar, for use in a third embodiment of the present invention;

FIG. 10c is a cross section showing the relative positioning of the inner stylet of FIG. 10a within the outer penetrating member of FIG. 10b for use in a third embodiment of the present invention;

FIG. 13 is a cross section of a penetrating member attached to an amplified piezoelectric actuator for use in a fifth embodiment of the present invention;

FIG. 14 is a cross section of a fifth embodiment of the present invention;

FIG. 14a is a cross section of the fifth embodiment of the present invention using a penetrating member with side port of FIG. 13a;

FIG. 15 is a cross section of a sixth embodiment of the present invention comprising a Cymbal actuator;

FIG. 16 is a cross section of the sixth embodiment of the present invention using the penetrating member with side port of FIG. 13a;

FIG. 18c is a sketch of a eighth embodiment of the present invention comprising two side ports in communication with needle attachment one connected to the front portion of the Langevin actuator and the other connected to the penetrating member without the actuator handle shown;

FIG. 18d is a sketch of a eighth embodiment of the present invention comprising the side port connected to the short bore and communication with needle attachment that is also connected to the front portion of the Langevin actuator and without the handle shown of the actuator of FIG. 18a;

FIG. 19a is a drawing of a ninth embodiment of the present invention comprising a conventional syringe of FIG. 2a attached at the side port location of the penetrating member hub shown in FIG. 18c with the actuator also connected into the hub and without the actuator handle shown;

FIG. 20a is a cross-sectional view of a tenth embodiment of the present invention using a voice coil for the driving actuator;

FIG. 20b is a cross-sectional view of the tenth embodiment of the present invention using a voice coil for the driving actuator wherein the position of the magnetic member and the coil are reversed from that of FIG. 20a;

FIG. 21 is an exemplary schematic of an electrical power cut off for use in the various embodiments of the present invention.

FIGS. 26a-26c show perspective, side and cross sectional views of a second portion of a horn of the invention.

FIGS. 32a-d show how a frequency sweep is performed to calculate impedance minimum in an overall calculation of resonant frequency, and how the value of impedance magnitude and phase angle shift θ change.

FIG. 33 is a flow diagram showing steps of a method utilized by a feedback method of an embodiment.

BRIEF DESCRIPTION OF THE INVENTION

Figure 1:
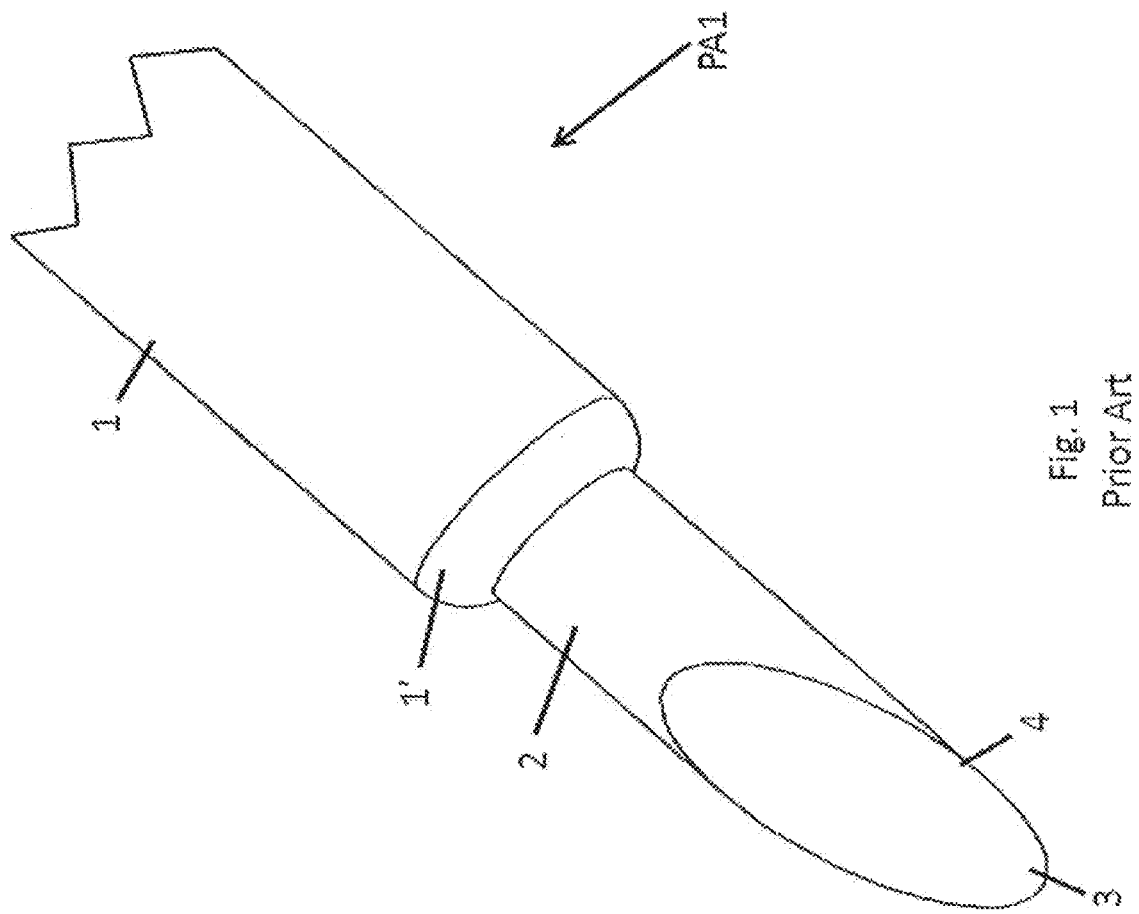
FIG. 1 is a partial isometric view of a distal end of a prior art biopsy needle.
Figure 2:
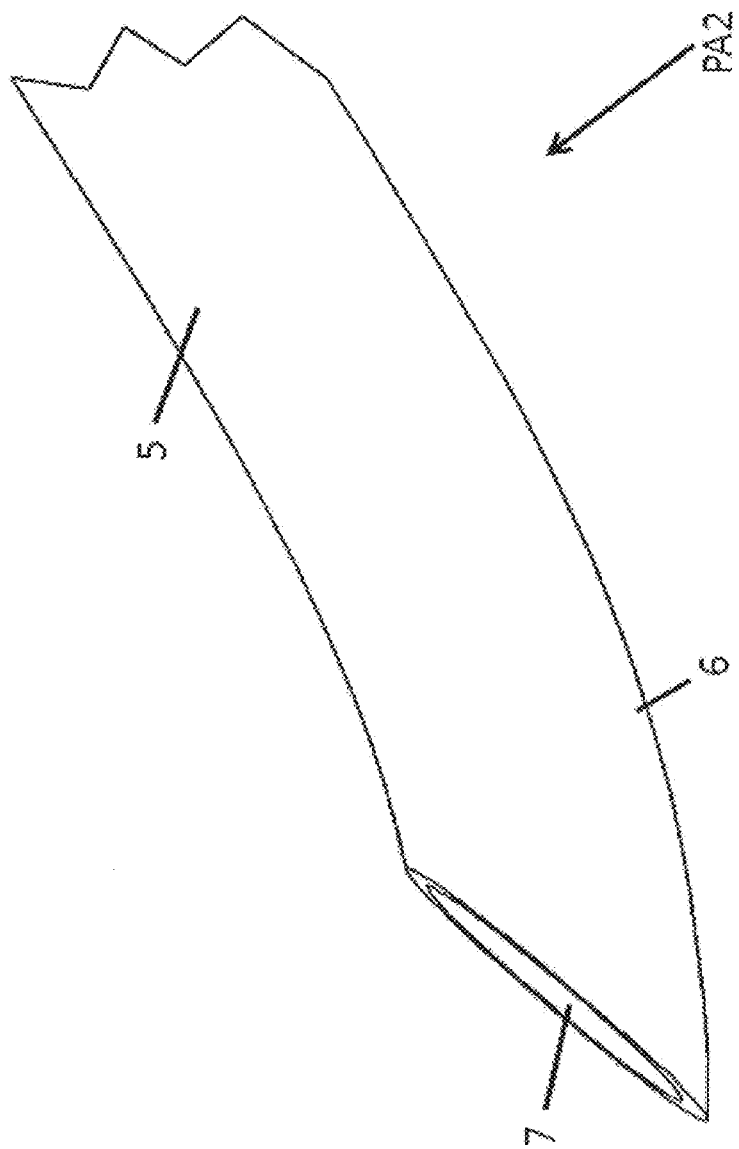
FIG. 2 is a partial side view of a distal end of a prior art epidural needle.
Figure 2A:
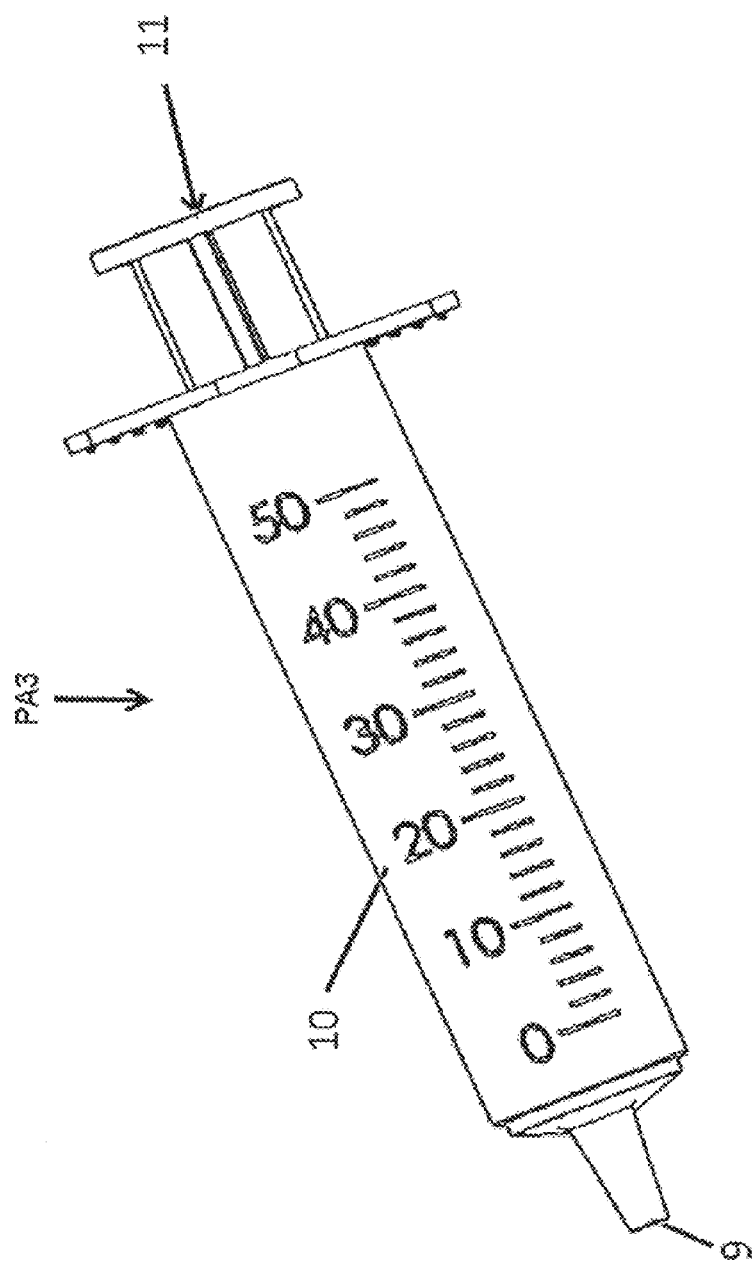
FIG. 2a is a plan view of a conventional prior art loss of resistance syringe.

The preferred embodiments of the present invention are illustrated in FIGS. 3-21 with the numerals referring to like and corresponding parts. For purposes of describing relative configuration of various elements of the invention, the terms "distal", "distally", "proximal" or "proximally" are not defined so narrowly as to mean a particular rigid direction, but, rather, are used as placeholders to define relative locations which shall be defined in context with the attached drawings and reference numerals. A listing of the various reference labels are provided at the end of this Specification. In addition, U.S. application Ser. No. 12/163,071 entitled "Medical Tool for Reduced Tool Penetration Force," filed on Jun. 27, 2008 is incorporated by reference in its entirety.

The effectiveness of the invention as described, for example, in the aforementioned preferred embodiments, utilizes reduction of force to optimize penetrating through tissue or materials found within the body. Essentially, when tissue is penetrated by the high speed operation of a penetrating member portion of the device, such as a needle, the force required for entry is reduced. In other words, a reduction of force effect is observed when a penetrating member (also referred to as a "tubular member"), for example a needle, is vibrated axially (e.g., reciprocated) during the insertion process and enough mechanical energy is present to break adhesive bonds between tissue and the penetrating member. The threshold limits of energy can be reached in the sonic to ultrasonic frequency ranges if the necessary amount of needle displacement is present.

To exploit the reduction of force effect, the medical device of the present invention is designed such that the penetrating distal tip portion attains a short travel distance or displacement, and vibrates sinusoidally with a high penetrating frequency. Utilizing the various device configurations as described in the aforementioned embodiments, it has been determined that the sinusoidal motion of the sharp distal tip must include a displacement for piezoelectric tools of between 35-100 μm, more preferably between 50-100 μm, at a frequency of between 20-50 kHz, but most preferably at 20-25 kHz. This motion is caused by the penetrating member 20 being attached to an actuating piezoelectric actuator operated at 50-150 Vpp/mm, but most preferably at 90 Vpp/mm where Vpp is known as the peak-to-peak voltage.

For example, FIG. 3 shows a graphical representation of the resisting force versus depth of a bone biopsy needle penetrating into hard tissue. In FIG. 3, the curve labeled A represents data for a needle in an "off" or non-vibrating condition and the curve labeled B represents data for a medical device having a needle that is vibrated by a piezoelectric actuator at 38 kHz and a displacement of 100 μm. As apparent from FIG. 3, curve A shows that without being vibrated, the force necessary to penetrate into a material is much higher than that for a needle being oscillated, such as that represented by curve B.

By way of example only, referring to FIG. 4, a Langevin actuator, generally indicated as 100, comprises a piezoelectric actuator which includes a body having a central hollow channel and includes a displaceable member (also referred to as a "horn") 110, an anchor (also referred to as a "rear mass") 112 and at least one piezoelectric element 114, but preferably comprises more than one. In particular, each piezoelectric element 114 may be formed into a piezoelectric ring that forms a hollow portion and wherein the piezoelectric elements 114 are secured within the body and attached between horn 110 and rear mass 112. A hollow or solid threaded bolt 116 is disposed within a center portion of rear mass 112, extending through a center portion of the at least one of piezoelectric elements 114 and ending within a central portion of horn 110. The bolt compresses the rear mass 112, the at least one of piezoelectric elements 114 and horn 110. The horn 110 and rear mass 112 are made of a metal such as titanium, stainless steel, ceramic (which include polycrystalline and single crystal inorganic materials), plastic, composite or, preferably, aluminum. The bolt 116 is of the same material as the horn 110 and rear mass 112. To protect patient and clinician from electric shock, at least a portion of the Langevin actuator 100, preferably at least the whole of the rear body 112, all of the at least one piezoelectric elements 114, and at least a portion of the horn 110, are disposed within a handle 118. Electrical connection is made at metallic tabs (not shown) formed between opposing faces of the at least one of piezoelectric elements 114. These tabs can be coupled via electrical conductors 114b connected to an AC power source or battery (e.g., positioned within a battery compartment of the present invention). The handle 118 comprises a shell portion which may be a plastic or a metal and a seal 120 which may be an elastomer. Seal 120 prevents moisture from entering or exiting from the central portions of the rear mass 112, piezoelectric elements 114 and horn 110. The central portion of the rear mass 112, piezoelectric elements 114 and horn 110 coincide with the hollow portion of the bolt 116 forming a continuous bore 126 within the Langevin actuator 100, the bore 126 having a distal opening 122 at a distal face 121 and a proximal opening 124 at a face opposite to the distal face 121. A Luer taper nose 123 is added to the actuator for clarity of connection.

It should be understood that the number of piezoelectric elements 114 does not form a limitation on the present invention and that it is within the broadest scope of the present invention to include one or more piezoelectric elements 114.

According to an alternative embodiment, a side port (not shown) may be formed at the horn 110 side of the actuator and the continuous bore 126 extends from a distal opening 122 at distal face 121 and in communication with this side port. The functional performance of the medical device is driven by the piezoelectric elements section. Piezoelectric elements 114, such as each of one or more piezoelectric material rings are capable of precise, controlled displacement and can generate energy at a specific frequency. The piezoelectric materials expand when exposed to an electrical input, due to the asymmetry of the crystal structure, in a process known as the converse piezoelectric effect. Contraction is also possible with negative voltage. Piezoelectric strain is quantified through the piezoelectric coefficients $d_{33}$, $d_{31}$, and $d_{15}$, multiplied by the electric field, E, to determine the strain, x, induced in the material. Ferroelectric polycrystalline materials, such as barium titanate (BT) and lead zirconate titanate (PZT), exhibit piezoelectricity when electrically poled. Simple devices composed of a disk or a multilayer type directly use the strain induced in a material by the applied electric field. Acoustic and ultrasonic vibrations can be generated by an alternating field tuned at the mechanical resonance frequency of a piezoelectric device. Piezoelectric components can be fabricated in a wide range of shapes and sizes. In one embodiment, piezoelectric component may be 2-5 mm in diameter and 3-5 mm long, possibly composed of several stacked rings, disks or plates. The exact dimensions of the piezoelectric component are performance dependent. The piezoelectric single or polycrystalline materials may be comprised of at least one of lead zirconate titanate (PZT), multilayer PZT, lead magnesium niobate-lead titanate (PMN-PT), multilayer PMN-PT, lead zinc niobate-lead titanate (PZN-PT), polyvinylidene difluoride (PVDF), multilayer PVDF, and other ferroelectric polymers. These materials also can be doped which changes properties and enhances the performance of the medical device. This list is not intended to be all inclusive of all possible piezoelectric materials. For example there is significant research into non-lead (Pb) containing materials that once developed will operate in this invention.

In the embodiment shown in FIG. 4a the side port SP is located on the penetrating member hub 525 of the hollow needle 130. In this alternate embodiment the hollow needle 130 penetrating member hub 525 is preferably metal or a combination of metal insert molded in a plastic. The side port SP would contain a female Luer taper opening to attach a loss of resistance conventional syringe PA3.

Figure 5:
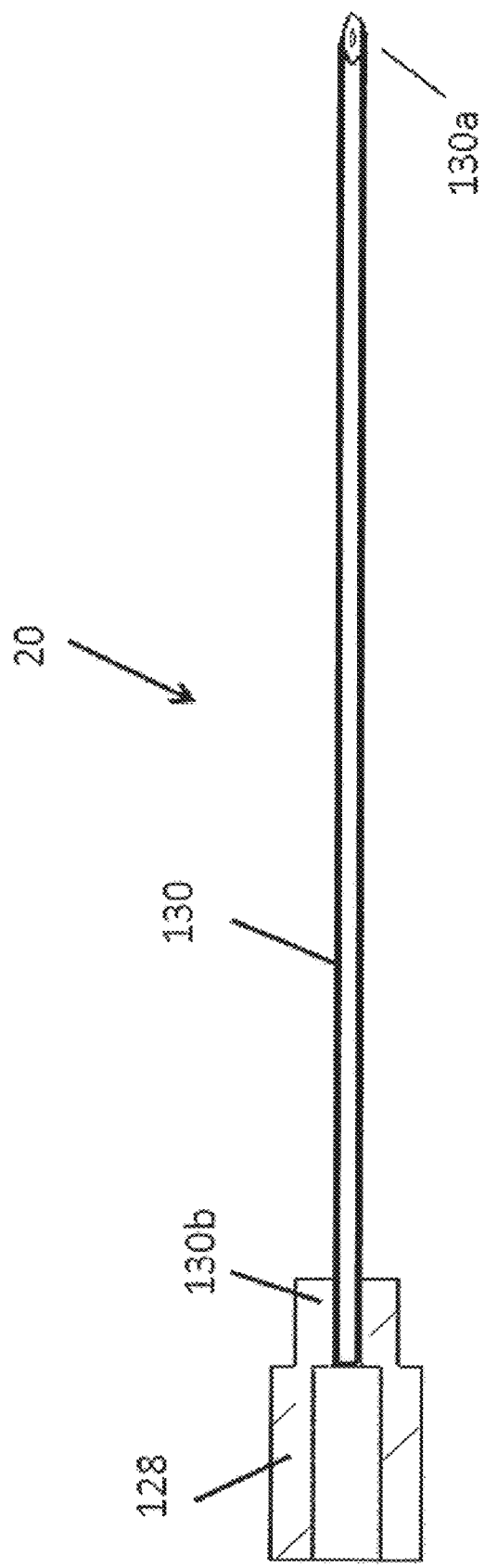
FIG. 5 is a cross section of a vascular entry needle used in a first embodiment of the invention.

Referring now to FIG. 5, a penetrating member, generally indicated as 20, for use in a first embodiment of the present invention comprises an attachment fitting 128 connected to proximal end 130b and the distal end 130a of a hollow needle 130 penetrates tissue. By way of example only, the attachment fitting 128 may comprise a Luer taper, plastic or metal fitting.

Referring now to FIG. 6, a plunger 12 for use in a first embodiment of the present invention comprises a plunger handle 132 attached to a proximal end 134a of a plunger shaft 134, and a plunger seal 136 attached to a distal end 134b of the plunger shaft 134. The plunger seal is used to seal the handle 118 so that contaminates such as water or bodily fluids do not reach the actuator elements or electrical connections. In another embodiment, the plunge will create a vacuum in the hollow penetrating member to aspirate bodily fluids and/or tissue for sampling such as in a soft tissue biopsy procedure.

Figure 6B:
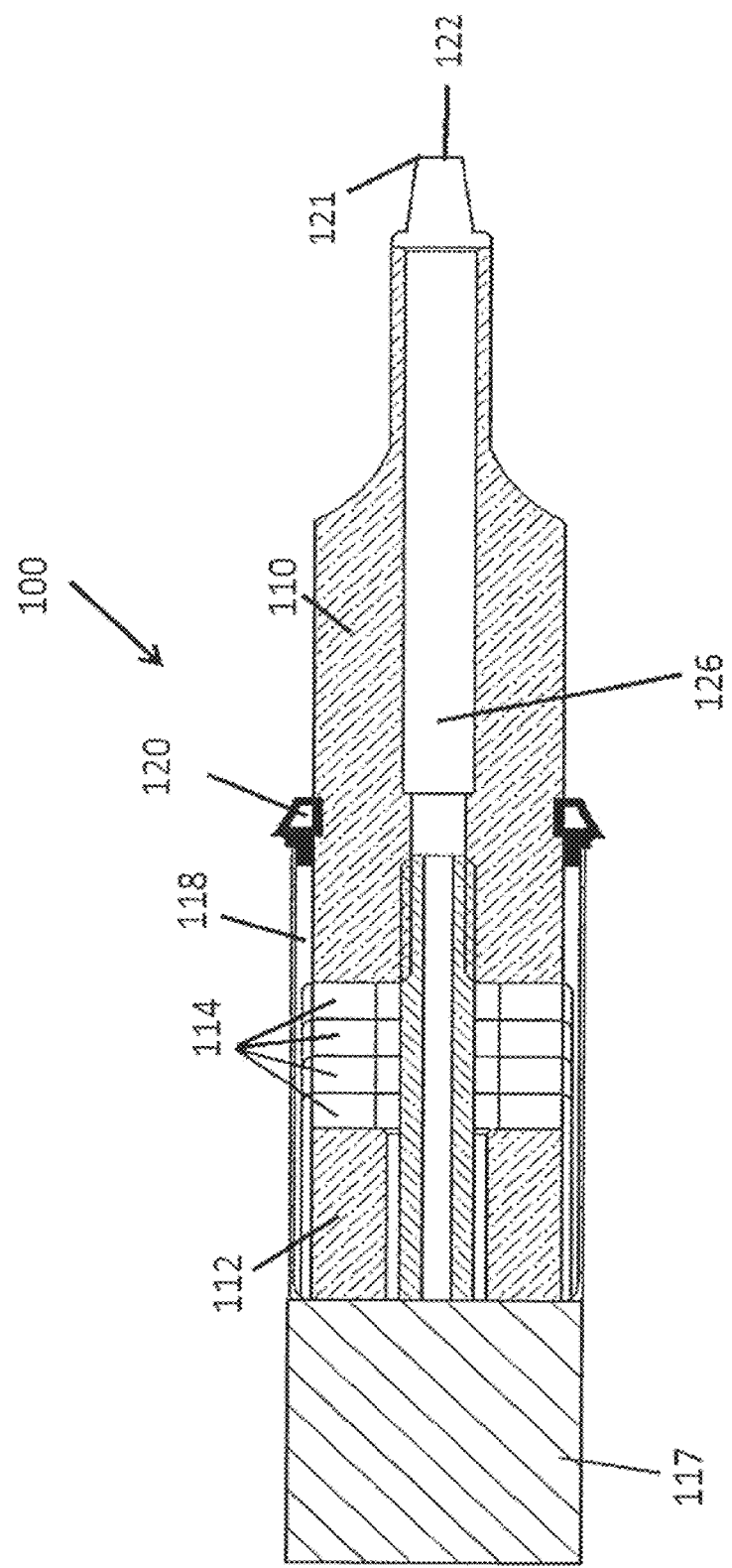
FIG. 6b depicts the present invention including a battery and inverter compartment attached at the end of the actuator.

In the most preferred embodiment, the side port is located on the penetrating member hub 525 at the end attachment point Referring now to FIG. 7, a first embodiment of the present invention, for example a penetrating introducer, generally indicated as 200, comprises an actuator, such as the Langevin actuator 100 described in FIG. 4, with the penetrating member 20 of FIG. 5 being attached at a distal face 121 of the actuator. The needle attachment fitting 128 is a threaded fitting, Luer taper, compression fitting or the like, and couples hollow needle 130 to a portion of distal face 121 such that it communicates with a distal volume of continuous bore 126. Plunger handle 132 may be a threaded, clamped, compressed or the like to bolt 116 so as to immobilize plunger 12 of FIG. 6. The present invention is sterilizable using such methods as steam sterilization, a sleeve, gamma, ethylene oxide (ETO). For example, FIG. 6a depicts a sterilization sleeve 115 for wires and housing used with the present invention. The preferred material for the needle attachment 128 is a metal or a metal insert in a molded plastic. FIG. 6b shows the Langevin actuator 100 with a possible configuration of the battery & inverter compartment 117 attached to the end of the actuator.

Returning to FIGS. 4 and 7, upon application of an external AC current at a predetermined frequency to the at least one of piezoelectric elements 114, the Langevin actuator 100 reactively changes shape in a sinusoidal fashion such that the relative position of distal face 121 with respect to say, a fixed position of plunger handle 132 attached to and held in place by bolt 116, changes by a predetermined displacement. Because the AC current is a sinusoidal signal, the result of activating the piezoelectric elements 114 is a sinusoidal, back and forth motion of the distal face 121 of horn 110, and, subsequently, a back and forth motion of needle 130, thereby reducing the force necessary for penetration through tissue. As mentioned previously, the AC energization can be provided directly from an AC source or from a DC source (e.g., onboard batteries) coupled to an inverter (e.g., oscillator/amplifier, etc.) which in turn is coupled to the piezoelectric elements 114. The DC source is the more preferred embodiment as wires and connections will need additional sterilization features.

FIG. 7a depicts a similar invention as shown in FIG. 7 but includes a penetrating member hub 525 with a side port SP connected to the hollow needle 130. This configuration enables pressure sensor to be mounted in the side port SP which once removed provides for a catheter to be inserted or fluids removed. This is likely the preferred embodiment when compared to FIG. 7 as the entire active device will not be at risk for contamination since the catheter or fluids do not traverse the actuator only the hollow needle 130 which could be manufactured for single use.

Figure 8:
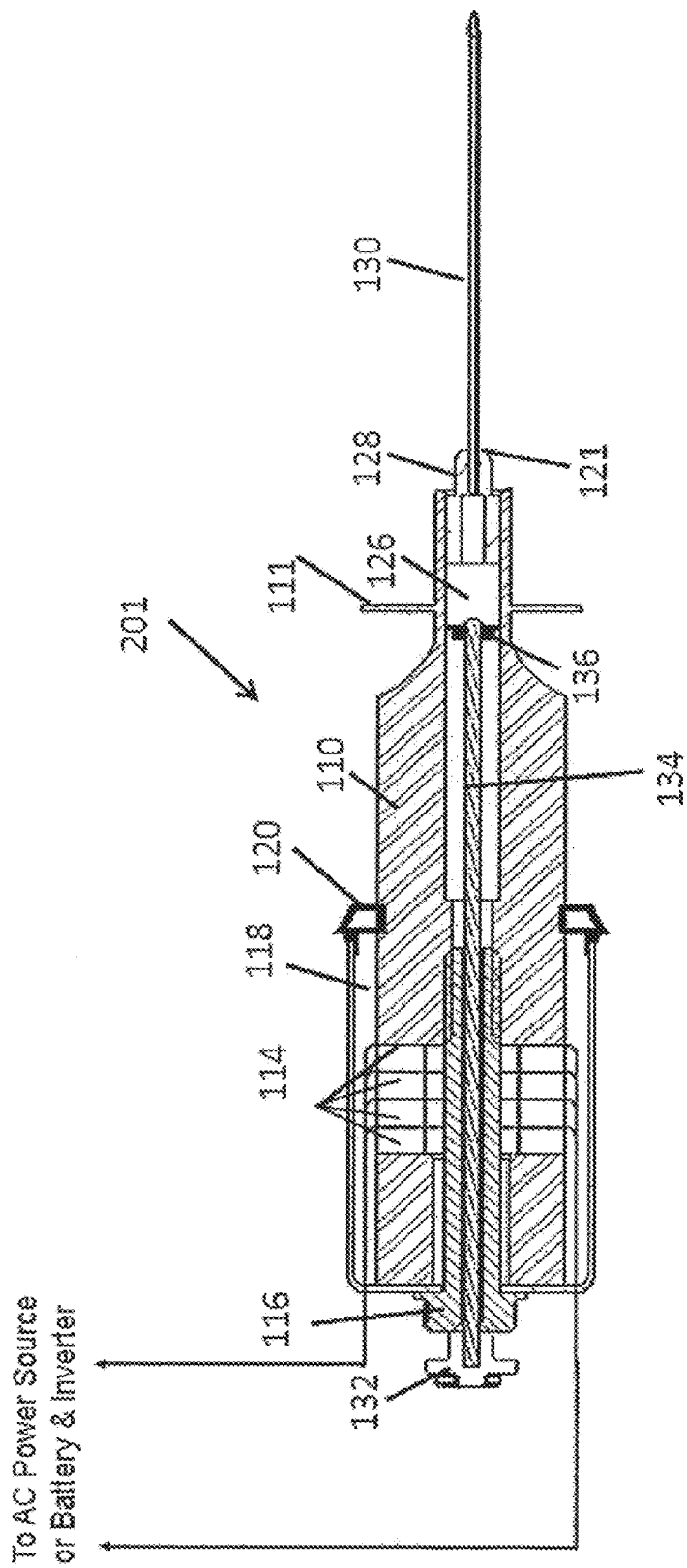
FIG. 8 is a cross section of another alternate design of the first embodiment of the invention of FIG. 7.
Figure 17:
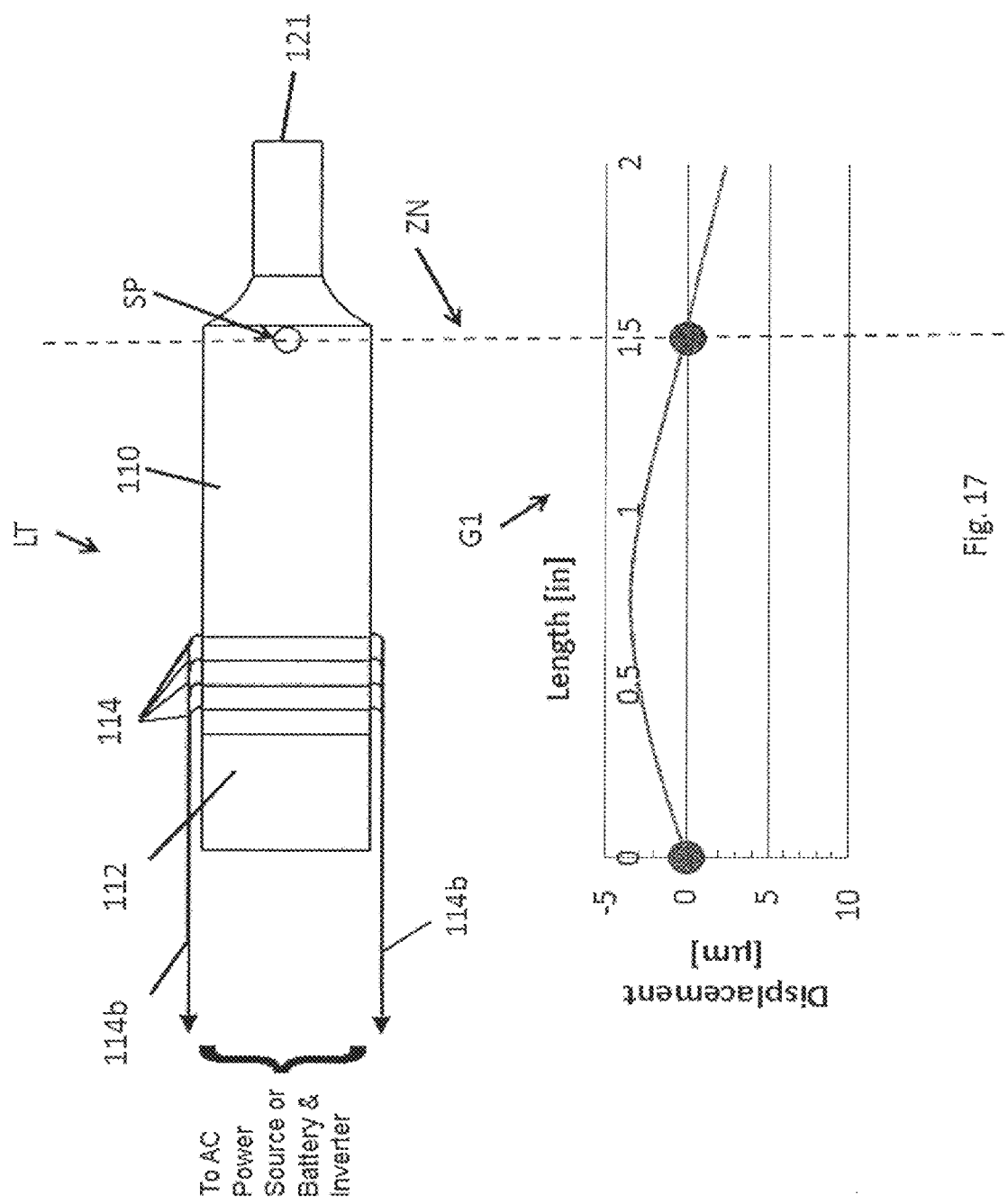
FIG. 17 shows the correlation between zero node points of a standing wave and the location of a side port on a Langevin actuator without the actuator handle shown.

Referring to FIG. 8, a supported introducer, generally indicated as 201, is similar to the penetrating introducer 200 of FIG. 7 additionally comprising support wings 111, existing for example as a flat portion onto which a user can grasp, and extending radially from an outer surface forming a mechanical zero node of the horn 110, as described later with regard to FIG. 17. A side port SP (not shown) could be 90 degrees clockwise or counterclockwise from the support wings that may be a location for providing access for aspirated sample retrieval, catheter insertion etc.

In an alternate embodiment of the present invention, the penetrating introducer 201 of FIG. 8 exists as a catheterization introducer, generally indicated as 202, as shown in FIG. 9. In this embodiment, rather than a plunger being introduced from a proximal end of the device, a catheter 129 is introduced from the proximal end of the device and is received through bore 126 as shown in FIG. 4, and may be passed through hollow needle 130. Upon having been inserted into a patient, hollow needle 130 forms a subcutaneous tunnel through which catheter 129 is introduced into the body. Upon successful introduction, the actuator may be detached from hollow needle 130 by decoupling attachment fitting 128 from the horn 110.

A more preferred embodiment 202b is shown in FIG. 9a where a side port SP permits the introduction of the catheter 129 into the present invention, rather than through the proximal end, as shown in FIG. 9. This configuration enables pressure sensor to be mounted in the side port SP which once removed enables a catheter to be inserted or fluids removed near the distal face 121 of the device. This is likely the preferred embodiment when compared to FIG. 9 as the entire active device will not be at risk for contamination since the catheter or fluids do not traverse the entire actuator.

In the most preferred embodiment 202c is shown in FIG. 9b where the side port SP located on the penetrating member hub 525 permits a pressure sensor to be mounted in the side port SP which once removed provides entry of an instrument such as a catheter 129 to be inserted or fluids aspirated. This is likely the preferred embodiment when compared to FIG. 9 as the entire active device will not be at risk for contamination since the catheter or fluids do not traverse the actuator only the hollow needle 130.

Now referring to FIG. 10a, an inner stylet, generally indicated as 14, comprises an inner stylet handle 142 attached to a proximal end of an inner stylet shaft 144. At a distal end of the inner stylet shaft 144, opposite to the handle 142 is a sharpened inner stylet tip 146. To support the inner stylet shaft 144, an outer trocar tube, generally indicated as 15, shown in FIG. 10b comprises a trocar attachment fitting 148 attached at a proximal end of an outer trocar body 150, which is a tubular structure open at opposite ends. The trocar attachment fitting 148 is hollow such that outer trocar body 150 is disposed within it. Additionally, one of the openings formed at opposite ends of the trocar body 150 is a distal trocar opening 152, the outer walls of which form distal trocar tip 154. As shown in FIG. 10c, inner stylet shaft 144 may be slidably disposed within outer trocar body 150 with inner stylet tip 146 extending beyond distal trocar tip 154. Together, the inner stylet 14 of FIG. 10a and outer trocar tube 15 of FIG. 10b form a structure similar to a trocar needle (e.g., a JAMSHIDI® biopsy tool).

Figure 11:
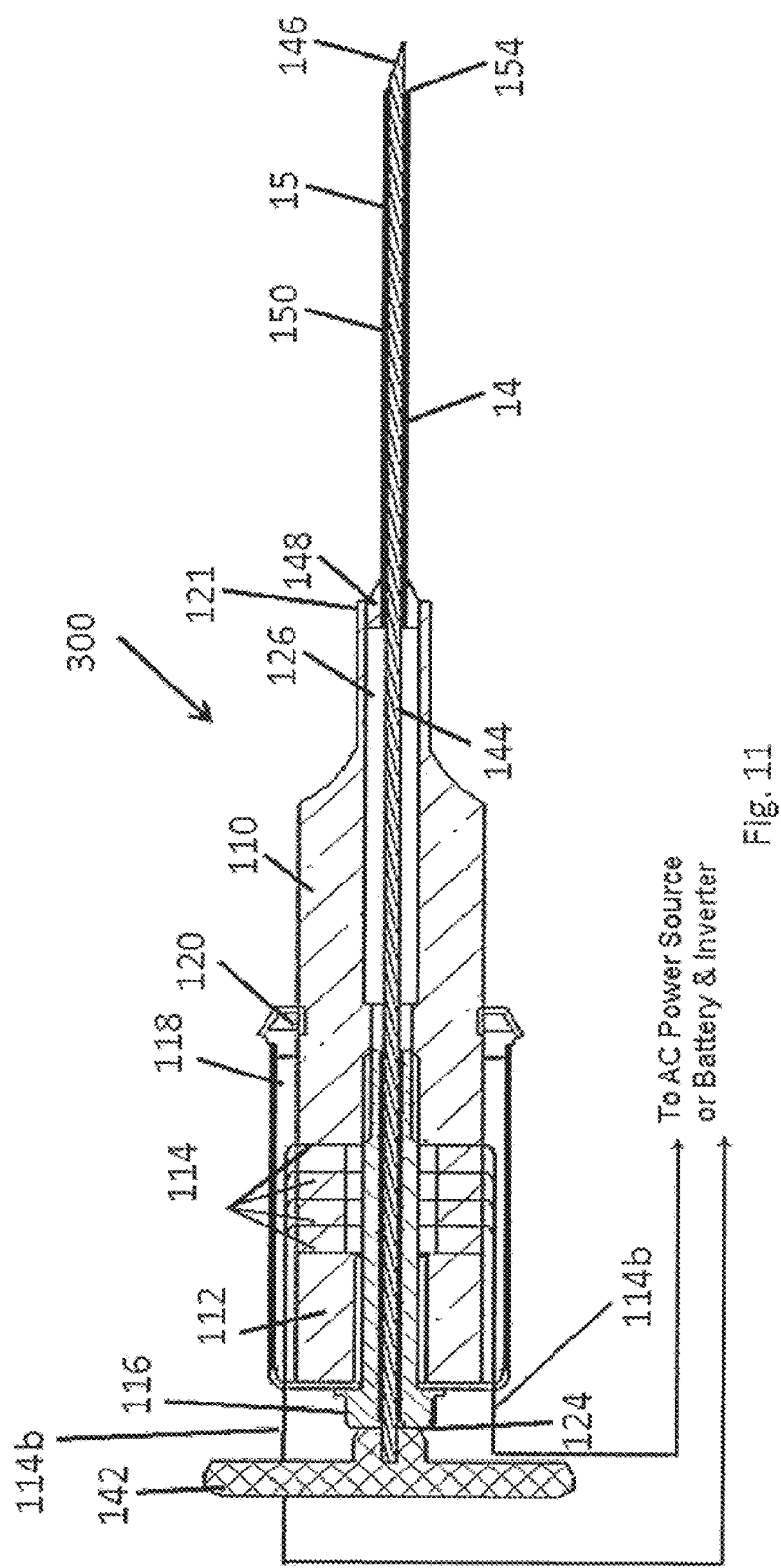
FIG. 11 is a cross section of a third embodiment of the present invention.

Referring now to FIG. 11, inner stylet 14 is slidably disposed within bore 126 of Langevin actuator 100 of FIG. 4 and outer trocar tube 15 of FIG. 10b, with outer trocar tube 15 attached to horn 110 to form a bone biopsy device, generally designated as 300. Inner stylet 14 extends in a manner such that handle 142 contacts bolt 116 when fully seated, with inner stylet shaft extending from handle 142 through proximal opening 124, through bore 126 and hollow portion of outer trocar body 150 finally terminating as inner stylet tip 146 at a location beyond distal trocar tip 154. In this embodiment, when the at least one of piezoelectric elements 114 of Langevin actuator 100 of FIG. 4 is electrically actuated via electrical conductors 114b at a predetermined frequency, motion in the form of compression and expansion of the rings is transferred to an anti-node location at the distal face 121 of horn 110. The motion is then transferred as actuation of outer trocar tube 15 of FIG. 10b.

Figure 12:
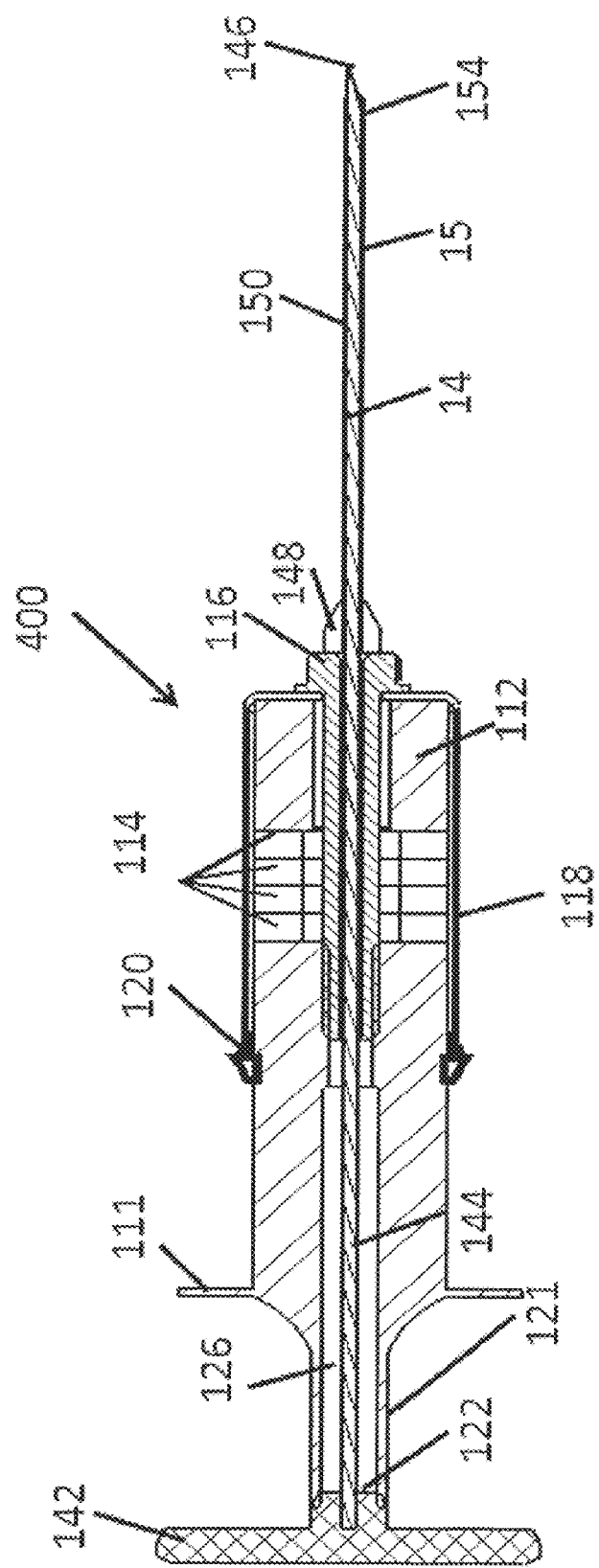
FIG. 12 is a cross section of a fourth embodiment of the present invention.

In an alternate embodiment, an advanced bone biopsy device, generally indicated as 400, shown in FIG. 12, comprises all of the elements of bone biopsy device 300 of FIG. 11, except that upon electrical activation of Langevin actuator 100 of FIG. 4 at a predetermined frequency, the motion is transferred as actuation of inner stylet 14. To perform this function, the positioning of the inner stylet shaft 14 of FIG. 10a and outer trocar tube 15 of FIG. 10b are inverted with respect to the configuration of FIG. 11. For example, in the advanced bone biopsy device 400, outer trocar tube 15 is attached to bolt 116. Additionally, inner stylet 14 extends in a manner such that handle 142 contacts distal face 121 of horn 110 when fully seated, with inner stylet shaft 144 extending from handle 142 through distal opening 122, through bore 126 and hollow portion of outer trocar body 150, finally terminating as inner stylet tip 146 at a location beyond distal trocar tip 154.

Figure 13A:
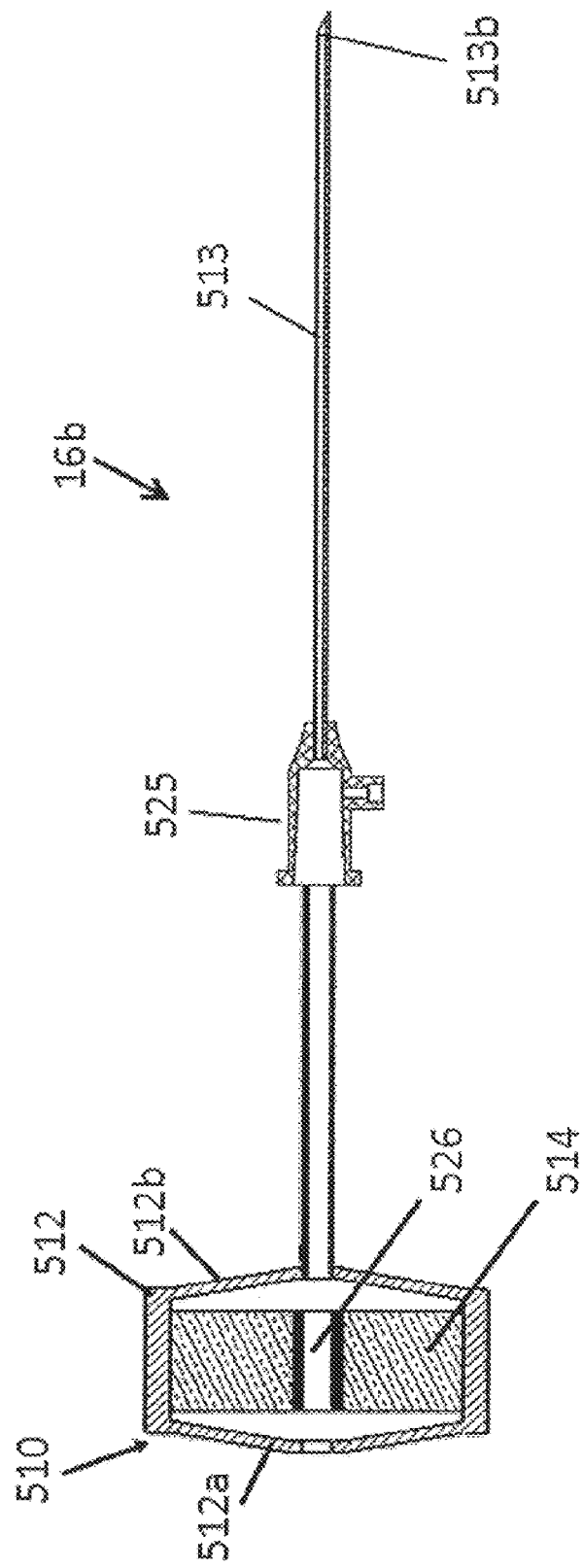
FIG. 13a is cross section of an alternate APA design of a penetrating member with side port for use the present invention.

While the previous embodiments have been described with respect to a Langevin actuator 100 as the actuating mechanism, the invention is not so limited. For example, as shown in FIG. 13, a hollow tubular structure having a sharpened distal tip 513b of the penetrating member 513 is attached at its proximal end 513a to an Amplified piezoelectric actuator (APA) 510 forming an APA needle, generally designated as 16. The amplified piezoelectric actuator (APA) 510 comprises a frame 512, normally formed of a metal such as brass or stainless steel, and a piezoelectric material 514 compressed within frame 512. An APA bore 526 may extend from a distal face through piezoelectric material 514 and through a proximal face 512a of frame 512. Hollow penetrating member 513, for example a hypodermic needle, is attached to the distal face 512b of frame 512, such that the hollow portion is concentrically aligned with the APA bore 526. As shown in FIG. 14, APA needle 16 may be disposed within a handle 518 forming an APA syringe, generally designated as 500. Important to this embodiment is that a proximal face 512a of frame 512 of amplified piezoelectric actuator (APA) 510 must be fixed as shown at 516 attachment point to an inner portion of handle 518 such that the APA bore 526, hollow penetrating member 513, a handle proximal opening 524 and handle distal opening 521 form a continuous channel through which fluids may pass into a patient. FIGS. 13a and 14a show alternate embodiments 16b and 500b, respectively, with a detachable penetrating member hub 525 enabling the single use penetrating member with re-usable active motion handle where the penetrating member hub 525 is described previously.

In operation, the piezoelectric material 514 expands during the AC voltage cycle, which causes the frame's proximal and distal faces 512a, 512b formed opposite of one another to move inward toward each other. Conversely, when piezoelectric material 514 compresses during the opposite AC cycle, an outward displacement of the frame's proximal and distal faces 512a, 512b away from one another occurs. However, in the present embodiment, the proximal face 512a of the frame is fixedly attached to body's 518 attachment point 516 so that any movement in the piezoelectric material stack will result in only a relative motion of distal face 512b and, thereby, a motion of the penetrating member 513.

Two examples of applicable amplified piezoelectric actuators (APAs) are the non-hinged type, and the grooved or hinged type. Details of the mechanics, operation and design of an example hinged or grooved APA are described in U.S. Pat. No. 6,465,936 (Knowles et al.), which is hereby incorporated by reference in its entirety. An example of a non-hinged APA is the Cedrat APA50XS, sold by Cedrat Technologies, and described in the Cedrat Piezo Products Catalogue "Piezo Actuators & Electronics" (Copyright© Cedrat Technologies June 2005).

Preferably, the APAs of the present invention are operated at frequencies in the range of 100 Hz to 20 kHz, more preferably 100 Hz to 1 kHz.

Alternatively, the actuator of the present invention may be a Cymbal actuator. For example, in FIG. 15, a Cymbal syringe, generally indicated as 600, including a Cymbal actuator 610 which comprises two endcaps 612 with the distal endcap 612b and proximal endcap 612a with at least a piezoelectric element 514 formed between the endcaps. The Cymbal syringe is centered on the Cymbal bore 626. The endcaps 612 enhance the mechanical response to an electrical input, or conversely, the electrical output generated by a mechanical load. Details of the flextensional Cymbal actuator technology is described by Meyer Jr., R. J., et al., "Displacement amplification of electroactive materials using the Cymbal flextensional transducer", Sensors and Actuators A 87 (2001), 157-162. By way of example, a Class V flextensional Cymbal actuator has a thickness of less than about 2 mm, weighs less than about 3 grams and resonates between about 1 and 100 kHz depending on geometry. With the low profile of the Cymbal design, high frequency radial motions of the piezoelectric material are transformed into low frequency (about 20-50 kHz) displacement motions through the cap-covered cavity. An example of a Cymbal actuator is described in U.S. Pat. No. 5,729,077 (Newnham et al.) and is hereby incorporated by reference. While the endcaps shown in the figures are round, they are not intended to be limited to only one shape or design. For example, a rectangular Cymbal endcap design is disclosed in Smith N.B., et al., "Rectangular Cymbal arrays for improved ultrasonic transdermal insulin delivery", J. Acoust. Soc. Am. Vol. 122, issue 4, October 2007. Cymbal actuators take advantage of the combined expansion in the piezoelectric charge coefficient $d_{33}$ (induced strain in direction 3 per unit field applied in direction 3) and contraction in the $d_{31}$ (induced strain in direction 1 per unit field applied in direction 3) of a piezoelectric material, along with the flextensional displacement of the endcaps 612, which is illustrated in FIG. 15. The design of the endcaps 612 allows both the longitudinal and transverse responses to contribute to the strain in the desired direction, creating an effective piezoelectric charge constant ($d_{eff}$) according to the formula, $d_{eff}=d_{33}+(-A*d_{31})$. Since $d_{31}$ is negative, and the amplification factor (A) can be as high as 100 as the endcaps 612 bend, the increase in displacement generated by the Cymbal compared to the piezoelectric material alone is significant. The endcaps 612 can be made of a variety of materials, such as brass, steel, titanium or KOVAR™, a nickel-cobalt ferrous alloy compatible with the thermal expansion of borosilicate glass which allows direct mechanical connections over a range of temperatures, optimized for performance and application conditions. The endcaps 612 also provide additional mechanical stability, ensuring long lifetimes for the Cymbal actuators.

The Cymbal actuator 610 drives the penetrating member 513. When activated by an AC current, the Cymbal actuator 610 vibrates sinusoidally with respect to the current's frequency. Because endcap 612a is fixed to an inner sidewall of body 518, when Cymbal actuator 610 is activated, endcap 612b moves with respect to the body in a direction parallel to the hypothetical long axis of the medical device. Further, the displacement of penetrating member 513 is amplified relative to the displacement originating at piezoelectric material 514 when it compresses and expands during activation due in part to the amplification caused by the design of endcaps 612. For example, the piezoelectric material 514 alone may only displace by about 1-2 microns, but attached to the endcaps 612, the Cymbal actuator 610 as a whole may generate up to about 1 kN (225 lb-f) of force and about 80 to 100 microns of displacement. This motion is further transferred through the penetrating member 513 as an amplified longitudinal displacement of 100-300 microns. For cases requiring higher displacement, a plurality of Cymbal actuators 610 can be stacked endcap-to-endcap to increase the total longitudinal displacement of the penetrating member 513. FIG. 16 shows an alternate embodiment 600b with a detachable penetrating member hub 525 enabling the single use penetrating member with reusable active motion handle.

In alternate embodiments of the present invention, an additional port opening is formed in communication with a channel formed within the body of the actuator, for example a Langevin actuator. In particular, FIGS. 17-19 are directed to these alternate embodiments and it should be noted that for clarity reasons, the handle 118 of the Langevin actuator is not shown in these figures.

Because the port opening is provided so as to attach a means for providing visual, audible or tactile feedback response (e.g., using any well-known detection mechanisms such as but not limited to electrical, magnetic, pressure, capacitive, inductive, etc. means) to indicate the successful penetration of the specific tissue such as the epidural space, it must be formed at a location which will be least detrimental to such means. In other words, because the actuator vibrates at high frequencies, each point along the actuator experiences a different displacement defined by a standing wave. In FIG. 17, a displacement graph G1 represents a standing wave having longitudinal displacements at points along the length of a Langevin actuator operated at 38 kHz. As can be seen in a displacement graph G1, two nodes having near zero displacement exist at particular locations in the standing wave. The two node ("zero node" ZN) locations on the Langevin actuator LT are therefore defined at a particular lengths along the Langevin actuator. In the specific design shown in FIG. 17 the nodes on the standing wave correspond to zero node, or locations having minimum displacements on the Langevin actuator LT. The locations of the zero nodes on the Langevin actuator LT are then located at a proximal face (not shown) of the rear mass opposite to the distal face 121. Line ZN defines the physical location of the other zero node at which a side port SP should be located, preferably centered, when formed in a Langevin actuator LT relative to second zero node of the standing wave in displacement graph G1. In the case shown in FIG. 17, the side port SP is formed at the horn 110 of the Langevin actuator LT, however a port opening is not necessarily so limited. A port opening can be placed anywhere along an actuator but a zero node location is preferred.

Figure 17A:
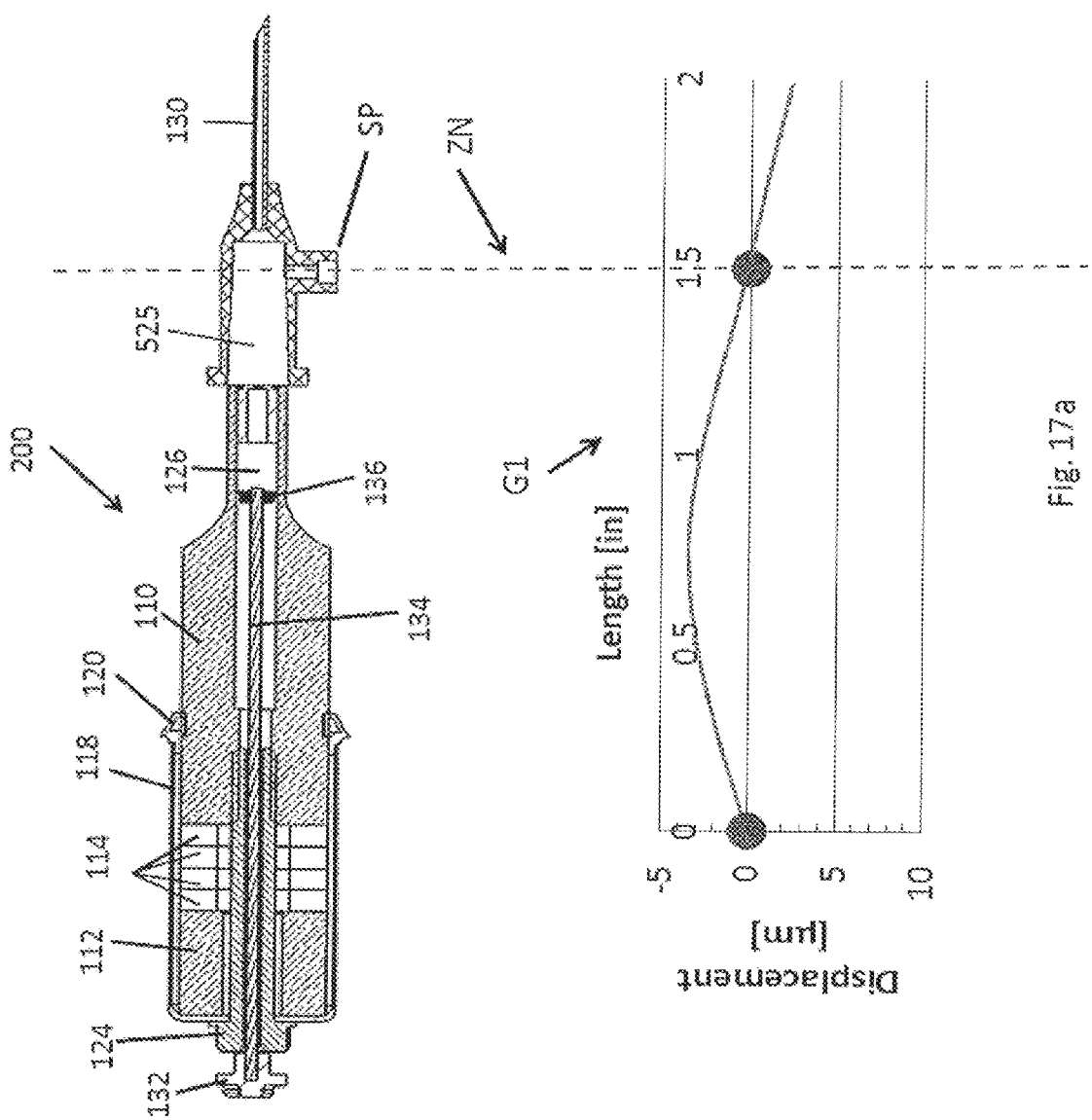
FIG. 17a shows the correlation between zero node points of a standing wave and the location of a side port on the penetrating member connected to the Langevin actuator.

In a more preferred embodiment, FIG. 17a describes the side port SP location on the zero node ZN of the penetrating member hub 525. In this embodiment, the design length includes both the needle length and actuator length to achieve the zero node ZN on the hollow needle 130 which includes length of penetrating member hub 525. A side port SP can be placed anywhere along hollow needle 130 but a zero node location on the penetrating member hub 525 is preferred.

Figure 18A:
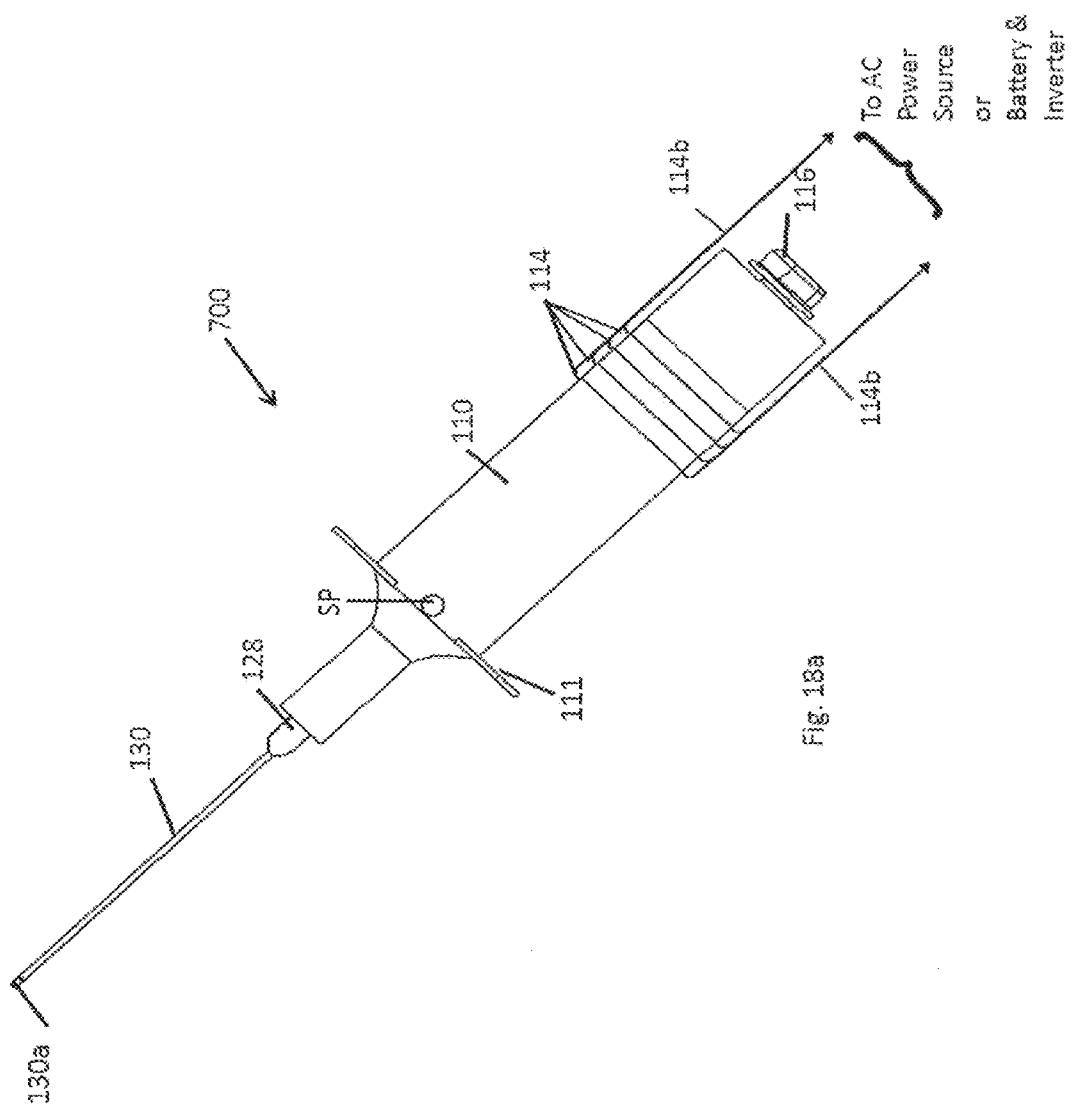
FIG. 18a is a functional diagram of a seventh embodiment of the present invention depicting a side port at a zero node location on a Langevin actuator without the handle shown.
Figure 19:
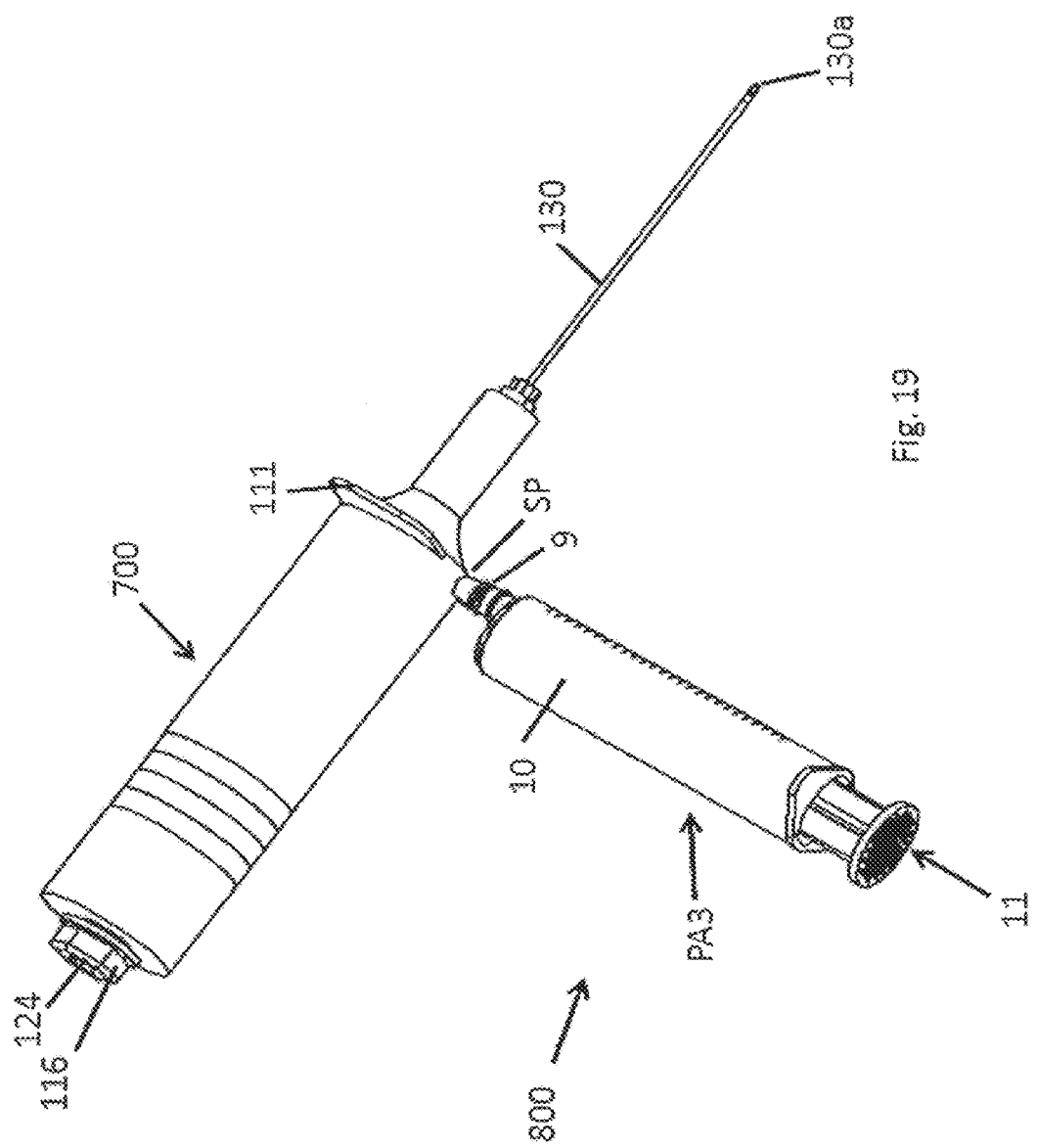
FIG. 19 is a drawing of a ninth embodiment of the present invention comprising a conventional syringe of FIG. 2a attached at the side port location of the actuator shown in FIG. 18a and without the actuator handle shown.

In FIG. 18a, a general side port configuration 700 of the present invention is shown with a side port SP as the port opening centered at a zero node location along the horn 110. Support wings 111 are also formed at a zero node to assist the clinician is holding and stabilizing the device.

Figure 18B:
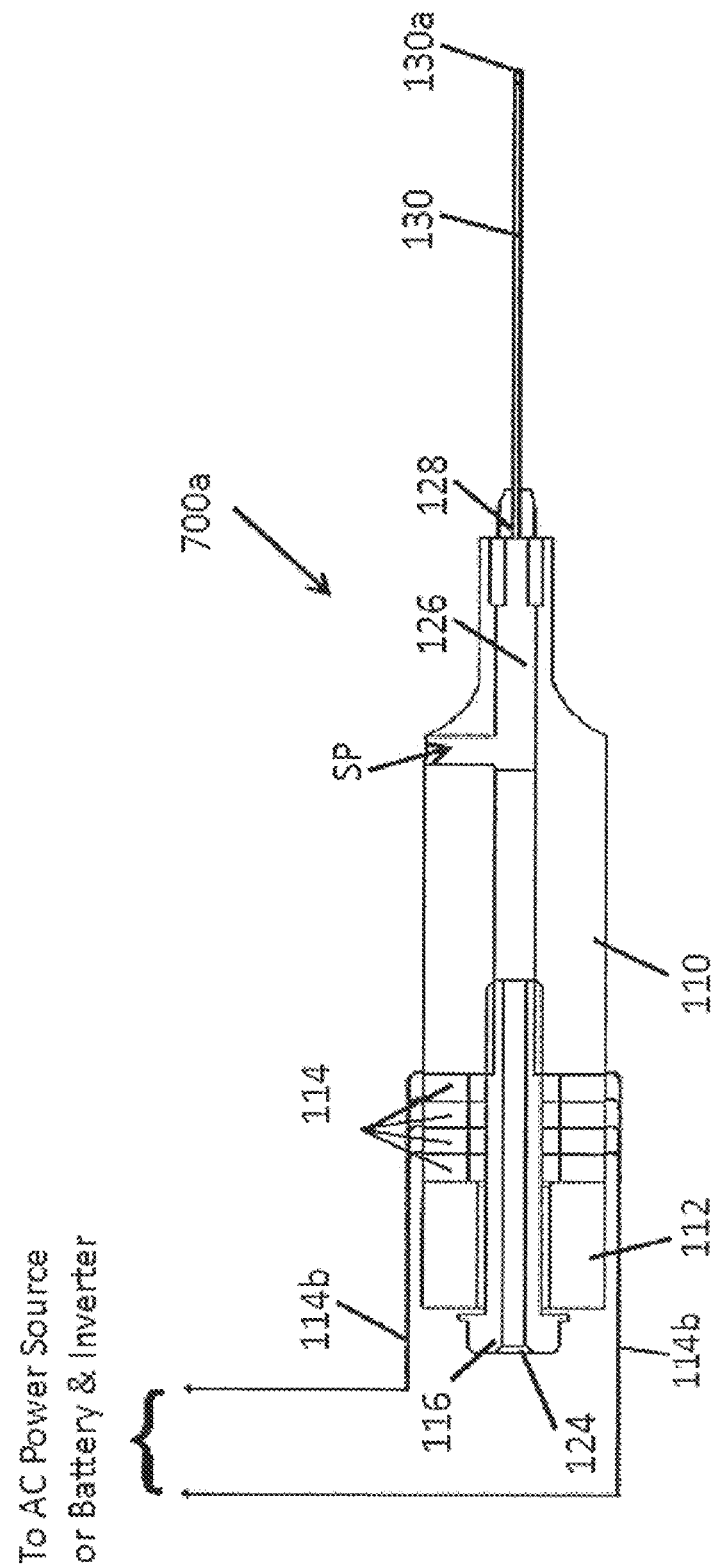
FIG. 18b is a functional diagram of a seventh embodiment of the present invention comprising the side port of FIG. 18a in communication with a central channel extending the length of a Langevin actuator and without the handle shown.

In a seventh embodiment of the present invention shown in FIG. 18b, a first side port configuration 700a has a channel for passing liquid, air or other materials comprises a continuous path from the proximal opening 124 through bore 126 passing through a distal opening (not shown) and extending through hollow needle 130 ending at a distal end 130a of the hollow needle which is open. In this seventh embodiment, the channel is in communication with the side port SP at a location along bore 126. Preferably, the side port SP is located at such a location along the actuator forming the first side port configuration 700a that acts as a zero node upon activating the device to vibrate.

Alternatively, as shown in an eighth embodiment of the invention in FIG. 18c, a second side port configuration 700b has a channel for passing liquid, air or other materials comprises a continuous path located on the hollow needle 130 penetrating member hub 525. In this eighth embodiment, the channel is in communication with the side port SP at a location along penetrating member hub 525. Preferably, the side port SP is located at such a location along the entire length (actuator and penetrating member) forming the second side port configuration 700b that acts as a zero node upon activating the device to vibrate. In a secondary side port SP located on the actuator an indicator such as a light emitting diode 1026 can be attached and connected to the electronics to indicate a visual loss of resistance.

Figure 18D:
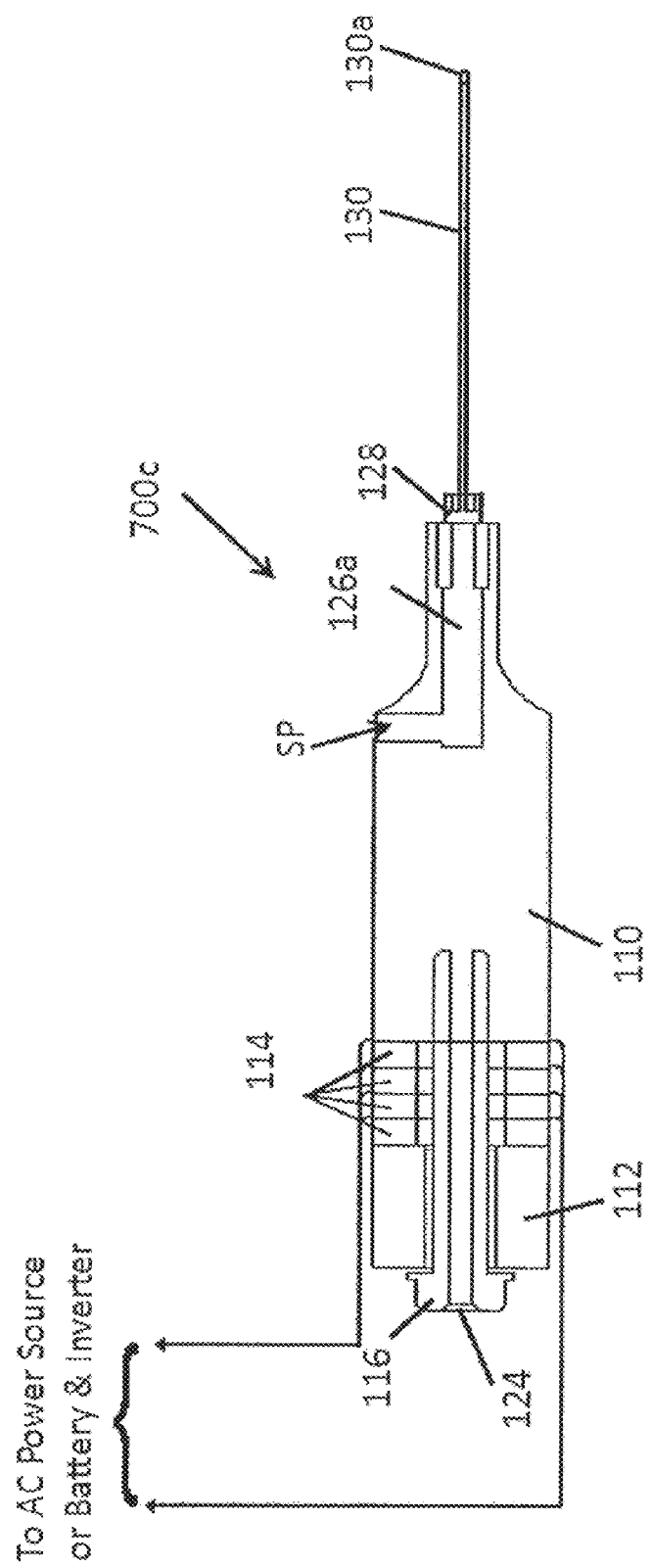

Alternatively, as shown in an eighth embodiment of the invention in FIG. 18d, a second side port SP configuration 700c has a small bore 126a for passing liquid, air or other materials located at zero node ZN to and from the hollow needle 130.

In a ninth embodiment of the present invention shown in FIG. 19, a feedback capable reduction of force tool 800 is provided. By way of example only, tool 800 comprises a means for providing tactile feedback response via a conventional loss of resistance syringe PA3 having a biasing element 11 with a plunger or balloon (e.g., elastomer device) or any other device that creates pressure then detects or measures pressure change. This device is coupled at a port location, preferably a side port SP located, via, by way of example only, a Luer Taper, male/female connector, screw-type connector, and preferably centered, at a zero node location. The tool 800 also includes an indicator in communication with the actuator 700 such as, but not limited to, an audible indicator, tactile indicator, or visual (e.g., deflation, optical, etc.).

In a most preferred embodiment of the present invention shown in FIG. 19a, a feedback capable reduction of force tool 800 is located on the hollow needle 130 at a zero node ZN on the penetrating member hub 525.

Figure 19B:
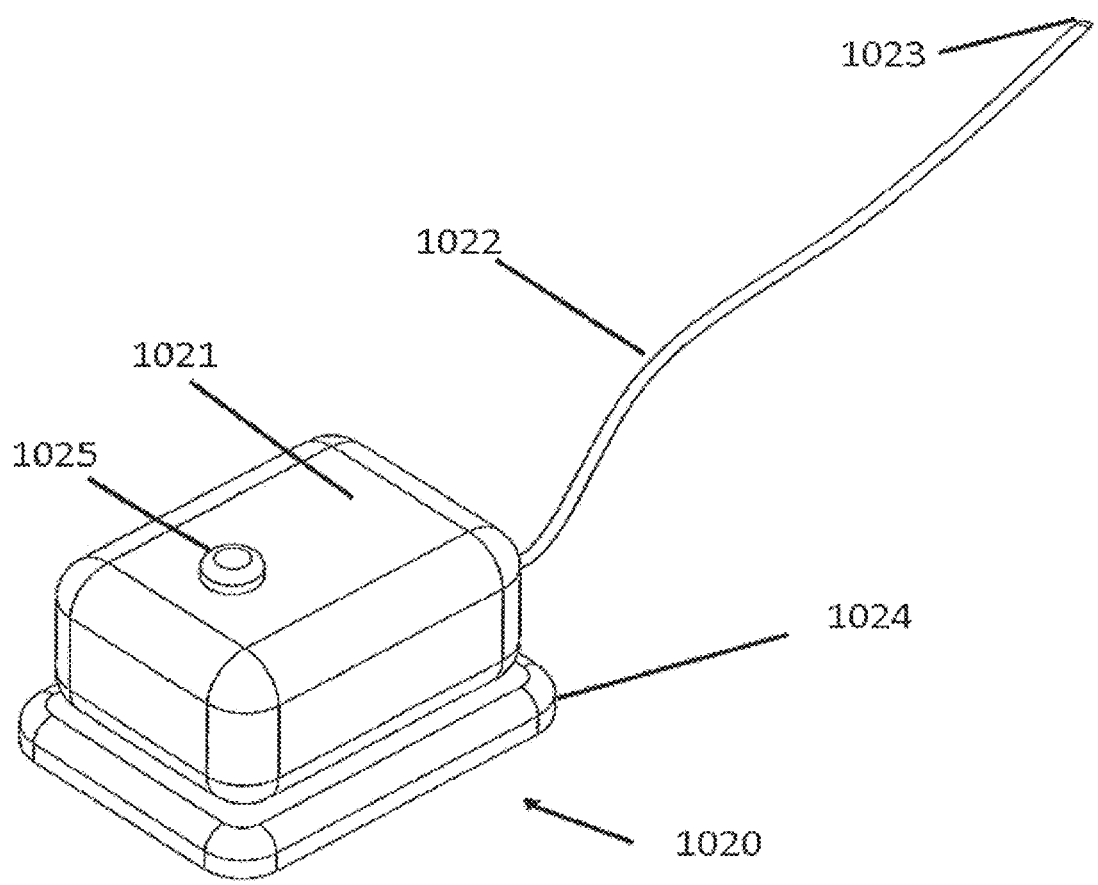
FIG. 19b is a drawing of a pressure sensing pump system for connection to a penetrating member.

Another embodiment described in FIG. 19b, a possible pressure sensor feedback system 1020 containing a small pumping mechanism equipped with a pressure or flow sensor to meter the amount of fluid being moved, a reservoir 1021 mounted on a base 1024. The pump fills with saline and connect via flexible tubing 1022 via an attachment fitting 1023 to the side port SP of the penetrating member. When loss of resistance (LOR) is detected, the electronic control system will close a switch and an indicator such as a light emitting diode (LED) (not shown) located on the side port SP of the actuator will turn-on indicating loss of resistance. The electronics control system at this point will turn the actuator off so that forward motion ceases. In additional embodiment, besides the visual signal, an audible signal a 'beep' could be incorporated into the pump system.

By way of example only, the following is an exemplary method of using the present invention, whereby a clinician uses the present invention for an epidural procedure. When performing an epidural procedure, the clinician first fills syringe PA3 with a fluid, such as a saline solution or air. The clinician then inserts the front portion 9 of the syringe into the side port SP of the actuator 700b. Upon electrically activating the actuator, the clinician holds actuator 700b with a first hand while pressing the distal end 130a of the hollow needle against a patient's back. The clinician continues to provide forward momentum, while also providing a biasing force against biasing element 11, advancing hollow needle 130. With continued forward momentum, the hollow needle punctures the supraspinous ligament, the instraspinous ligament, and the ligamentum flavum (see FIG. 7, for example). Upon puncturing the ligamentum flavum, the distal end 130a of the needle enters the epidural space at which point there is a pressure drop from the biasing element 11 to the opening at the distal end 130a. The pressure drop allows for the solution to be ejected from the opening at the distal end 130a, and the continued biasing of the biasing element 11 combined with the loss of volume of saline results in a loss of resistance (LOR) against the clinician's thumb and a visibly identifiable motion of the biasing element 11. When the biasing element moves due to this lack of resistance, the clinician quickly identifies that the epidural space has been successfully reached and quickly stops forward momentum of the actuator. Additionally, because the activation of the actuator results in a vibration of the needle 130, the clinician does not need to provide such a high penetration force and can quickly react to stop himself/herself before advancing the needle beyond the epidural space.

It should be further noted that it is within the broadest scope of the present invention to include syringes or other mechanisms which provide automatic biasing, such that the clinician does not have to apply a biasing force against the biasing element 11 prior to entry into, for example, the epidural space. In particular, the automatic biasing force (implemented, for example, via a spring, an elastomer, or any other well-known biasing mechanism such as, but not limited to, those described in U.S. Patent Publication No. 2007/0142766 (Sundar, et al.)) maintains an equal resistance as the needle is moved through the supraspinous ligament, the instraspinous ligament, and the ligamentum flavum. Upon entry into the epidural space, the biasing force is no longer resisted and this can be manifested in a variety of ways to the clinician, but not limited to, movement of the biasing element, or any other visual, audible or tactile indication using any well-known detection mechanisms such as but not limited to electrical, magnetic, pressure, capacitive, inductive, etc. means. For example, a pressure signal indicative of a loss of solution resistance automatically cuts off power to the driver actuator (e.g., piezoelectric elements, voice coil, solenoid, etc.).

While feedback means have been coupled to the side port SP, the invention is not so limited to feedback means. Any device may be coupled to a port location of the actuator, or ideally at the side port SP location even those devices simply being a means for providing or removing liquid, gas or other material such as a conventional syringe.

While the above-described embodiments of the present invention are made with respect to a handheld medical tool having a vibrating penetrating member and utilizing a Langevin actuator, Cymbal actuator, or APA for actuation, as mentioned earlier, the present invention is not limited to these actuator assemblies. Generally, any type of motor comprising an actuator assembly, further comprising a mass coupled to a piezoelectric material, or a voice coil motor, or solenoid, or any other translational motion device, would also fall within the spirit and scope of the invention. Furthermore, where the actuator assembly comprises a mass coupled to a piezoelectric material, the actuator assembly having a geometry which, upon actuation, amplifies the motion in a direction beyond the maximum strain of the piezoelectric material, would also fall within the spirit and scope of the present invention.

FIG. 20a depicts an alternative embodiment 900 of the present invention using a voice coil for the driving actuator rather than piezoelectric elements. Voice coil actuator (also referred to as a "voice coil motor") creates low frequency reciprocating motion. The voice coil has a bandwidth of approximately 10-60 Hz and a displacement of up to 10 mm that is dependent upon applied AC voltage. In particular, when an alternating electric current is applied through the conducting coil 902, the result is a Lorentz Force in a direction defined by a function of the cross-product between the direction of current through the conductive coil 902 and magnetic field vectors of the magnetic member 904. The force results in a reciprocating motion of the magnetic member 904 relative to the coil support tube 906 which is held in place by the body 910. With the magnetic member 904 fixed to a driving tube 912, the driving tube 912 communicates this motion to an extension member 914 which in turn communicates motion to the penetrating member 20.

A first attachment point 916a fixes the distal end of the coil support tube 906 to the body 910. A second attachment point 916b fixes the proximal end of the coil support tube 906 to the body 910. The conducting coil may be made of different configurations including but not limited to several layers formed by a single wire, several layers formed of different wires either round or other geometric shapes. In a first embodiment of the conducting coil shown in FIG. 20a, a first layer of conductive wire is formed by wrapping the wire in a turn-like and spiral fashion and in a radial direction around the coil-support tube with each complete revolution forming a turn next to the previous one and down a first longitudinal direction of the coil support tube. After a predetermined number of turns, an additional layer is formed over the first layer by overlapping a first turn of a second layer of the wire over the last turn of the first layer and, while continuing to wrap the wire in the same radial direction as the first layer, forming a second spiral of wiring with at least the same number of turns as the first layer, each turn formed next to the previous one and in a longitudinal direction opposite to that of the direction in which the first layer was formed. In this embodiment, additional layers may be added by overlapping a first turn of each additional layer of the wire over the last turn of a previous layer and, while continuing to wrap the wire in the same radial direction as the previous layer, forming an additional spiral of wiring with at least the same number of turns as the previous layer, each turn formed next to the previous one and in a longitudinal direction opposite to that of the direction in which the previous layer is formed.

Figure 20B:
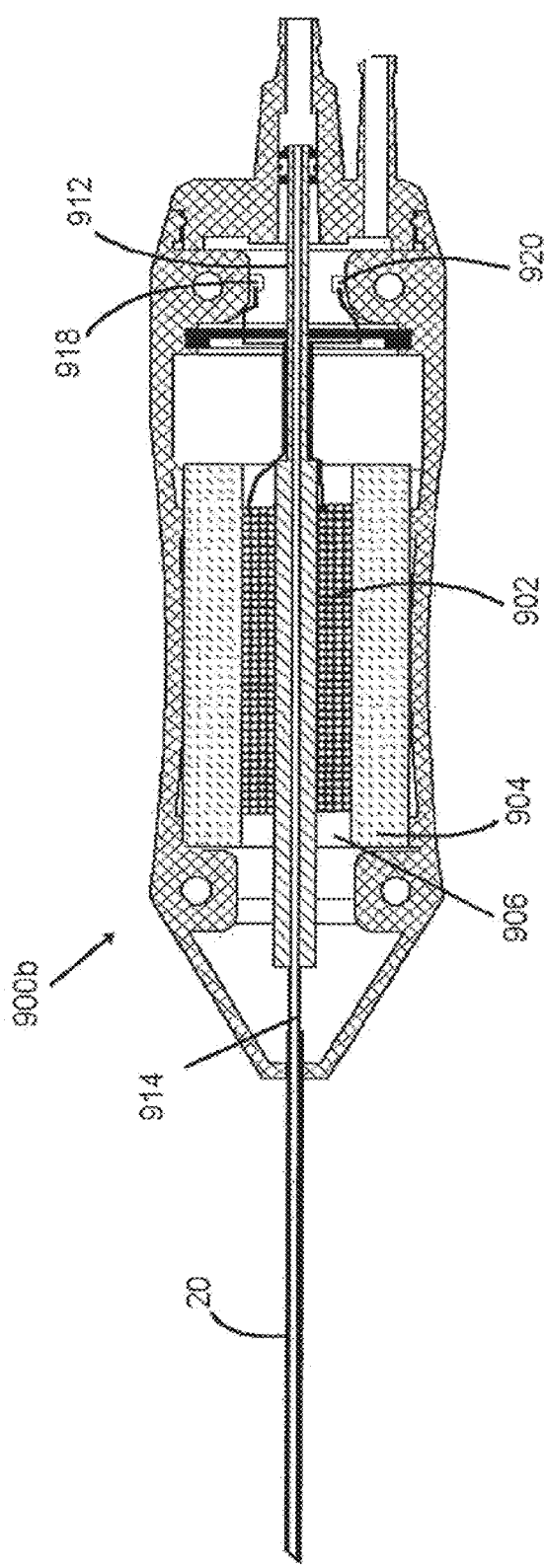

An alternative voice coil embodiment 900b is shown in FIG. 20b. In particular, in this alternative, the locations of the magnetic member 904 and conductive coil 902 are switched. In other words, the conductive coil is wrapped around and attached to the driving tube 912 and the magnetic member 904 is located along an outside radius of the coil support tube 906.

An electrical signal is applied at the conductive attachment sites 918 and 920 and causes the formation of the Lorentz force to form in an alternating direction that moves the conductive coil 902 and extension member 914 reciprocally along the longitudinal axis of the device. The conductive coils are physically in contact with the driving tube in this embodiment.

Figure 20C:
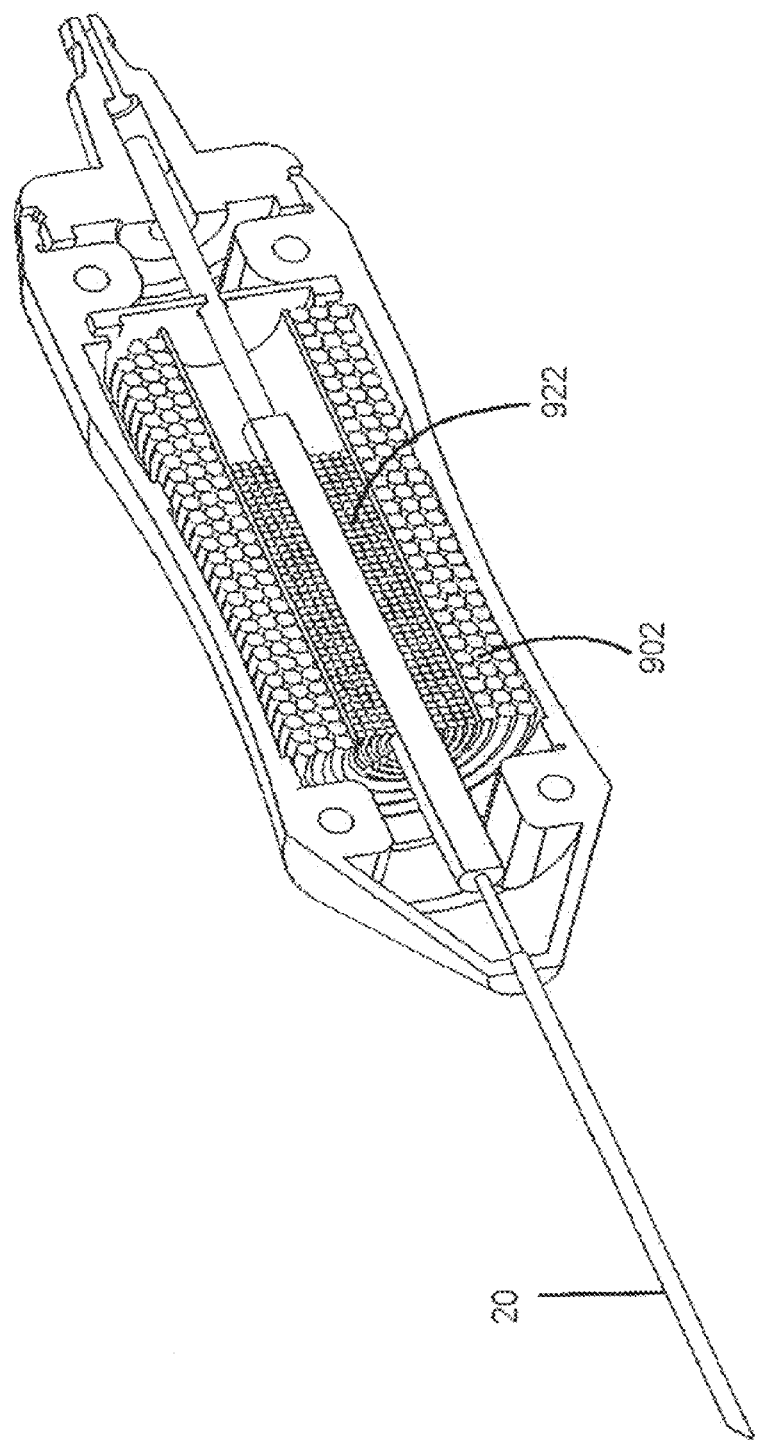
FIG. 20c is an isometric cross-sectional view of the tenth embodiment of the present invention using two coils.

FIG. 20c depicts another embodiment of the present invention using a voice coil type actuating mechanism and is of a different configuration than that used in FIGS. 20a and 20b. For example, in this alternative embodiment, a voice-coil actuating mechanism is substituted with a dual-coil actuating mechanism and as a result of this substitution, the magnetic member 904 of the voice-coil is replaced with second conductive coil 922. In other words, the second conductive coil 922 is wrapped around and attached to the driving tube 912 and the first conductive coil 902 is located, as in the first preferred embodiment, along an outside radius of the coil support tube 906. In a first embodiment of the configuration of FIG. 20c, the inner coil 922 is conducting direct current DC and the outer coil is conducting alternating current AC. In an alternative embodiment, the inner coil is conducting alternating current AC and the outer coil is conducting direct current DC. In an additional embodiment, both the inner coil and the outer coil are conducting alternating current AC.

Figure 20D:
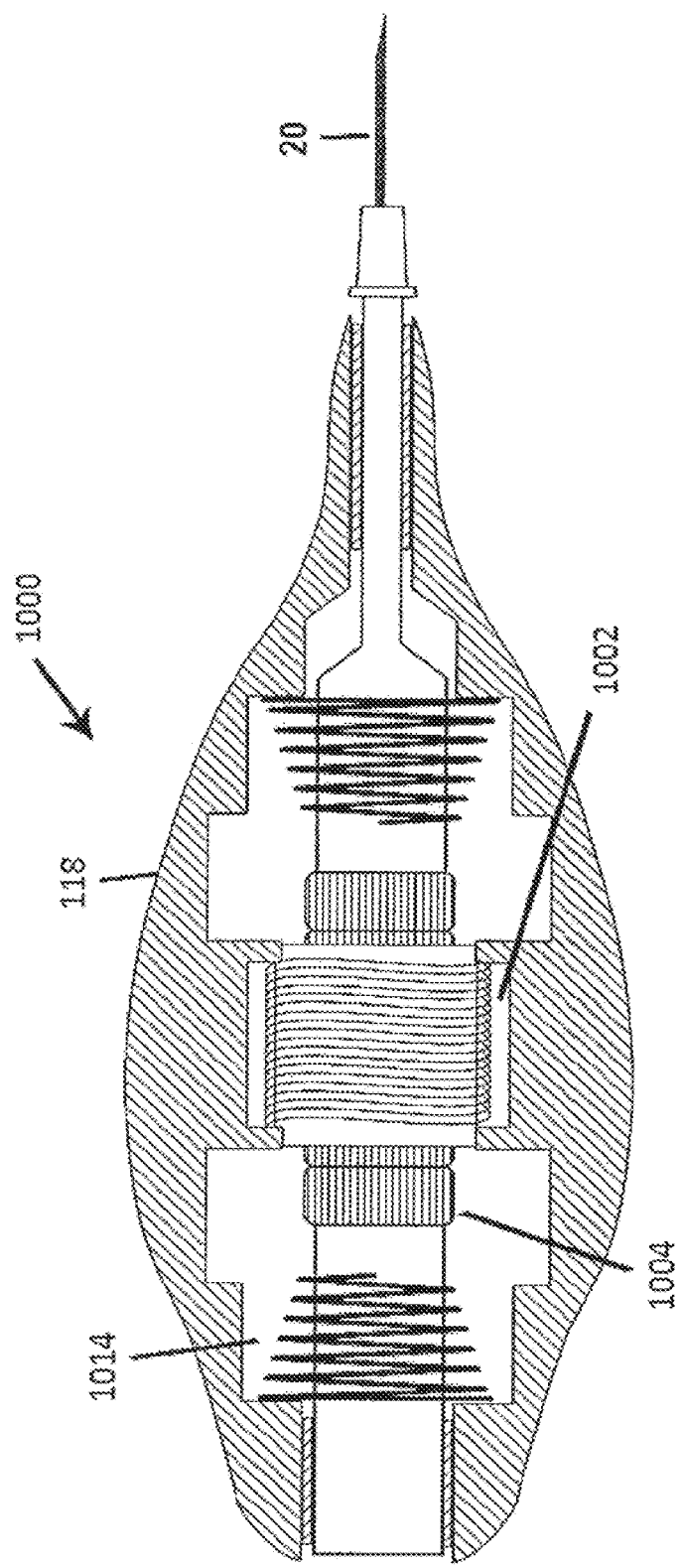
FIG. 20d is a side cross-sectional view of the tenth embodiment of the present invention using a solenoid with springs.

In all of the voice coil actuator configurations described, springs may be used to limit and control certain dynamic aspects of the penetrating member 20. FIG. 20d depicts another variation of the voice coil actuator mechanism of the tenth embodiment using springs, Medical Tool using solenoid actuator 1000. As with the other voice coil embodiments using coils, the basic principle of actuation is caused by a time varying magnetic field created inside a solenoid coil 1002 which acts on a set of very strong permanent magnets. The magnets 1004 and the entire penetrating member 20 assembly oscillate back and forth through the solenoid coil 1002. The springs 1014 (such as those shown in FIG. 20d) absorb and release energy at each cycle, amplifying the vibration seen at the penetrating member 20. The resonant properties of the device can be optimized by magnet selection, number of coil turns in the solenoid, mass of the shaft, and the stiffness of the springs.

From the above description, it may be appreciated that the present invention provides significant benefits over conventional medical devices. The configuration of the actuating means described above, such as embodiments comprising a Langevin actuator, Cymbal actuator, or an APA, accommodates the use of piezoelectric actuating members in a medical instrument by enabling the displacement of the penetrating sharps member or needle to such frequencies that cause a reduction of force needed for penetrating through tissue during procedures such as bone biopsy, epidural catheterization or vascular entry. Electrical signal control facilitated by an electrically coupled feedback system could provide the capability of high oscillation rate actuation, control over penetration depth, electrical cut off (faster response than human) and low traction force for these procedures. FIG. 21 depicts, by way of example only, an electrical cut off configuration. A pressure transducer PT monitors the pressure from the penetrating member 20 or of a fluid in communication with the tissue through the present invention. While the penetrating member 20 is penetrating tissue, the pressure detected by the pressure transducer PT is high and the switch S is normally closed. As soon as there is a drop in pressure (indicating passage through the final layer of tissue), the pressure transducer PT signal opens the switch S, thereby cutting off power to the medical tool. In addition, or a visual, audible or tactile indicator immediately activates warning the operator of sufficient passage by the penetrating member 20 and power cut off. It is within the broadest scope of the present invention to encompass a variety of power cut off configurations, including solid state switching and/or digital controls.

Another electrical power cut off implementation detects a forward motion of the biasing element 11 discussed previously. In particular, once the penetrating member 20 passes through the last tissue layer, pressure on the biasing element 11 is relieved and the incremental movement of the biasing element 11 into the body 10 is detected by a sensor which instantly opens the switch S and thereby cuts off electrical power to the present invention.

Additionally, the feedback control of the electronics enables the device to be vibrated in such a way that the force is also reduced as the penetrating member is retracted from the living being as would be necessary in bone biopsy after the tissue is extracted.

Additional Embodiments

Additional embodiments of the present invention are illustrated in FIGS. 22-31.

Feedback Means Using Electromechanical Properties

As discussed above, a medical device for penetrating living being tissue can include a driving actuator for converting electrical energy into reciprocating motion when energized. The driving actuator can include a distal end and a first channel extending to the distal end, and a penetrating member can be coupled to the distal end of the driving actuator. The medical device can include a feedback subsystem that detects any change of electromechanical properties related to the operation of the penetrating member. For example, the feedback subsystem can be utilized for: (i) indicating to an apparatus operator a different type of tissue has been contacted by said penetrating member; and/or (ii) automatically controlling force being applied to said penetrating member.

Figure 22:
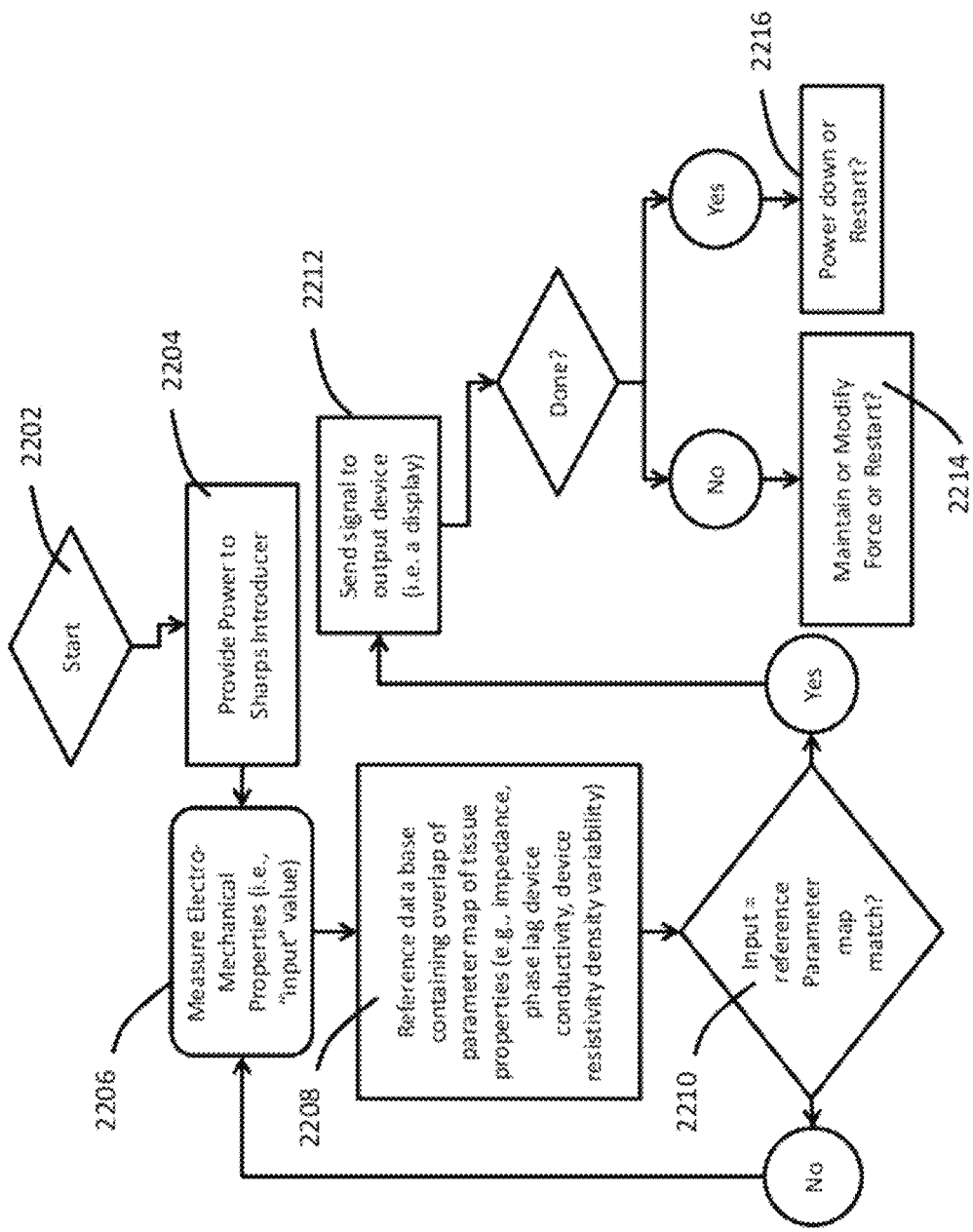
FIG. 22 is a flow diagram of how the feedback subsystem of the present invention operates.

FIG. 22 provides a general method of implementing the feedback subsystem of the present invention. Using a predetermined association of electromechanical properties regarding various tissues (e.g., fat, muscle, cartilage, bone, etc.), as described with regard to FIG. 23, the feedback subsystem includes a sensor for detecting system/device changes as the sharps member (e.g., needle) penetrates tissue and wherein the sensor generates a signal characteristic of the electromechanical property being monitored. The sensor (e.g., impedance analyzer, such as the Hewlett Packard, HP 4192A) feeds this signal to a microcontroller that references a look-up table to determine the material that the sharps/penetrating member 20 is currently passing through. The microcontroller can drive a display or other indicators or alerts for informing the operator of the present invention, for example the use of Langevin actuator 100, just what the sharps/penetrating member 20 is currently cutting. One alternative is for the microcontroller to deenergize the penetrating introducer 200, if necessary.

Figure 23:
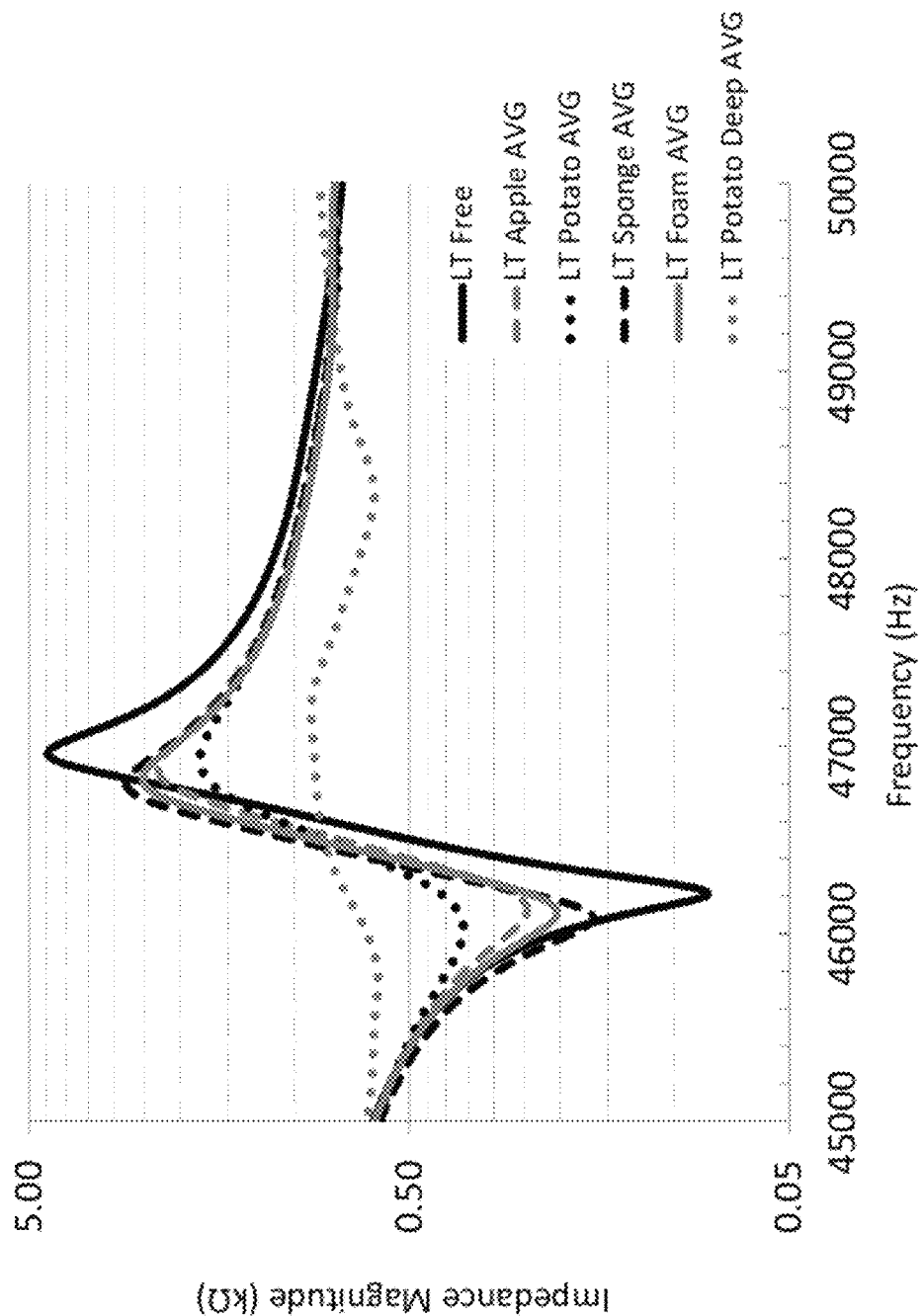
FIG. 23 is a graph of test data (e.g., device impedance data) of the vibrating reference member versus the material being tested.

FIG. 23 shows data which demonstrates an exemplary methodology for determining characteristic electromechanical properties (e.g., system/device impedance, system/device phase lag, system/device conductivity, density variability, etc.) to be used for generating a "look-up" table or other association of tissue with the changing electromechanical property as part of the feedback subsystem. By way of example only, a 1.5 inch long, hollow, 3 faceted Trocar needle (vibrating reference member) is mounted on a bolted Langevin transducer. The resonance frequency of the system in air is ~47 kHz. The tip is inserted 5 mm into different test media with a variety of densities. FIG. 23 is a plot of the amplitude of the impedance (by way of example only) curve as a function of frequency. The peak is the anti-resonant frequency. The dip downward to the left is the resonant frequency. The upper curve is the needle/transducer assembly in air. The lower curves show a reduction in amplitude, and slight shift in anti-resonant frequency, as the needle is inserted into media of increasing stiffness (e.g., sponge, dense foam, apple, potato). The lowest curve shows the result when the needle was inserted ~1 inch into the potato. These shifts in amplitude and frequency (and other potential measurements such as phase lag, resistance and density) provide various electromechanical (EM) properties that can be used for distinguishing between different tissues, and also the depth of insertion.

Figure 24:
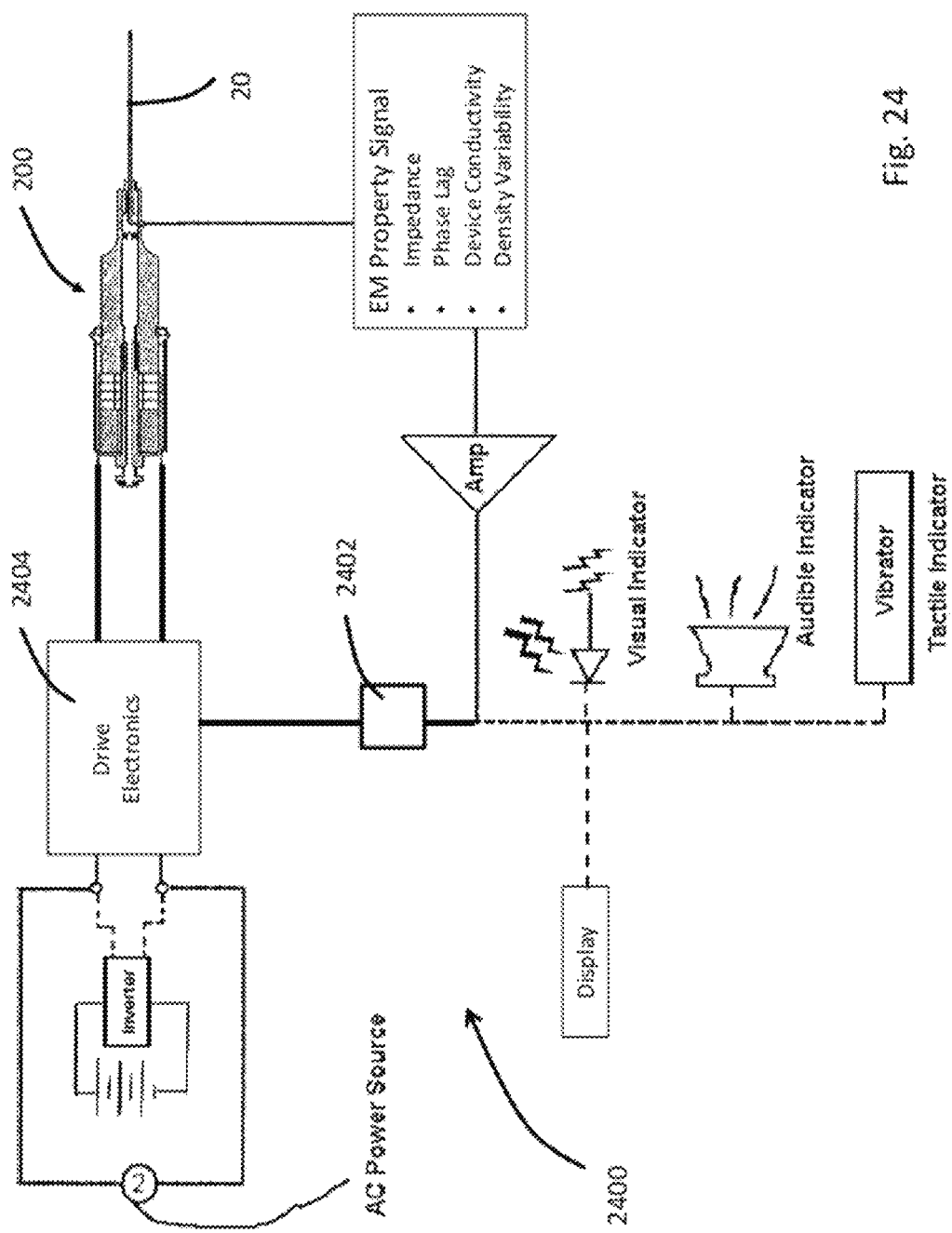
FIG. 24 is an exemplary schematic of a feedback subsystem for use in the various embodiments of the present invention.

FIG. 24 provides an exemplary block diagram of a feedback subsystem 2400 for use in the present invention. The microcontroller 2402 may comprise a look-up table in an internal memory generated in accordance with that described with regard to FIG. 23. Depending on which EM property is being monitored (e.g., device impedance, device conductivity, device phase lag, density variability, etc.) a corresponding sensor feeds back the corresponding EM property signal to the microcontroller 2402 which uses the process of FIG. 22 to drive indicators or the display to alert the device operator as to the tissue that the penetrating/sharps member 20 is currently passing through. The microcontroller 2402 also controls the device energization via drive electronics 2404. It should be noted that embodiments, such as penetrating introducer 200 may be powered from an external AC power source or batteries. In either case, power to the penetrating introducer 200 can be immediately controlled or even interrupted when particular tissue penetration is detected.

As discussed above, it is within the broadest scope of the present invention to encompass a variety of feedback configurations, including solid state switching and/or digital controls. Additionally, the present invention comprises sensors for providing feedback, either visually, audibly, or by tactile response, using a variety of detection mechanisms (such as, but not limited to, electrical, magnetic, pressure, capacitive, inductive, etc. means) to indicate successful penetration of various tissues, or of voids within the body so that the clinician is aware of the tissue being passed through by the sharps member. Additionally, the feedback control of the electronics enables a device, such as penetrating introducer 200 to be vibrated in such a way that the force is also reduced as the sharps member is retracted from the living being. Even pressure transducers can be coupled on or adjacent the sharps member where pressure of the distal tip of the sharps member against the tissue being passed through is transferred from the distal tip through the device body for EM property detection.

Thus, an additional embodiment of a medical device, such as penetrating introducer 200 in FIG. 4, for penetrating living being tissue can include a driving actuator, such as Langevin actuator 100. The driving actuator can convert electrical energy into reciprocating motion when energized. The driving actuator can include a distal end such as distal face 121 and a first channel, such as bore 126 extending to the distal end. The device can further include a penetrating member 20 that is coupled to the distal end of the driving actuator 100.

Additionally, the device 200 of FIG. 4 can include a feedback subsystem 2400 as shown in FIG. 24. The feedback subsystem 2400 can detect any change of electromechanical properties related to the operation of the penetrating member. By detecting any change in electromechanical properties as discussed above, the subsystem can indicate to an apparatus operator that a different type of tissue has been contacted by said penetrating member 20 via forces that work against the actuators ability to reciprocate, and cause changes in electromechanical properties. Alternatively, by detecting any change in electromechanical properties, as discussed above, the subsystem 2400 can automatically control a force being applied to said penetrating member. For example, the force required for penetrating tissue using said penetrating member can be varied by automatically controlling a frequency at which the device actuates.

In an embodiment, the subsystem 2400 can monitor at least one electromechanical property such as phase lag in a control signal of said apparatus (for example phase lag between a voltage and current signal magnitude), a conductivity change detected by the device (for example, conductivity of surrounding tissue adjacent to a sharps member of the device), a voltage change in a control signal of said apparatus (for example, a voltage change detected by a force sensor upon penetration of a sharps member of the device into a cavity such as the epidural space).

As discussed above, devices described herein can include one or more of several types of actuators. In an embodiment, the device can include at least one piezoelectric element such as piezoelectric element 114. The piezoelectric elements can convert electrical energy into oscillatory motion when they are energized.

A device, such as device 200 of FIG. 4, for use with subsystem 2400 can include a second channel, such as that extending from an opening similar to sideport SP of FIG. 9b, having a first end in communication with said first channel 126 of FIG. 9a and a second end positioned at an exterior surface of the actuator. This second channel is similar to the channel extending from opening 2502 in FIG. 26c. The first channel 126 of the device 200 can extend through the device's penetrating member 130. A third channel 124 can extend through at least one piezoelectric element. The first and third channels can be aligned. The device's anchor/rear mass 112 can have a fourth channel 124 that extends therethrough along a longitudinal axis of the anchor. The fourth channel 124 can be aligned with the first 126 and third channels to form a continuous channel through the actuator. The first channel 126 can extend through a portion of the penetrating member.

As discussed above, the penetrating member of the embodiments described herein can be one of a hypodermic needle, catheterization needle, Tuohy needle, bone biopsy trocar, spinal needle, nerve block needle, trocar access ports and interventional radiology needle. As discussed above, the actuator of the embodiments described herein can be a Langevin actuator, such as Langevin actuator 100. As discussed above, an exterior surface of the actuator can comprise a side port, such as sideport SP of FIG. 18a for providing fluid communication with, or passage of a catheter within a penetrating member such as penetrating member 130.

Figure 25A:
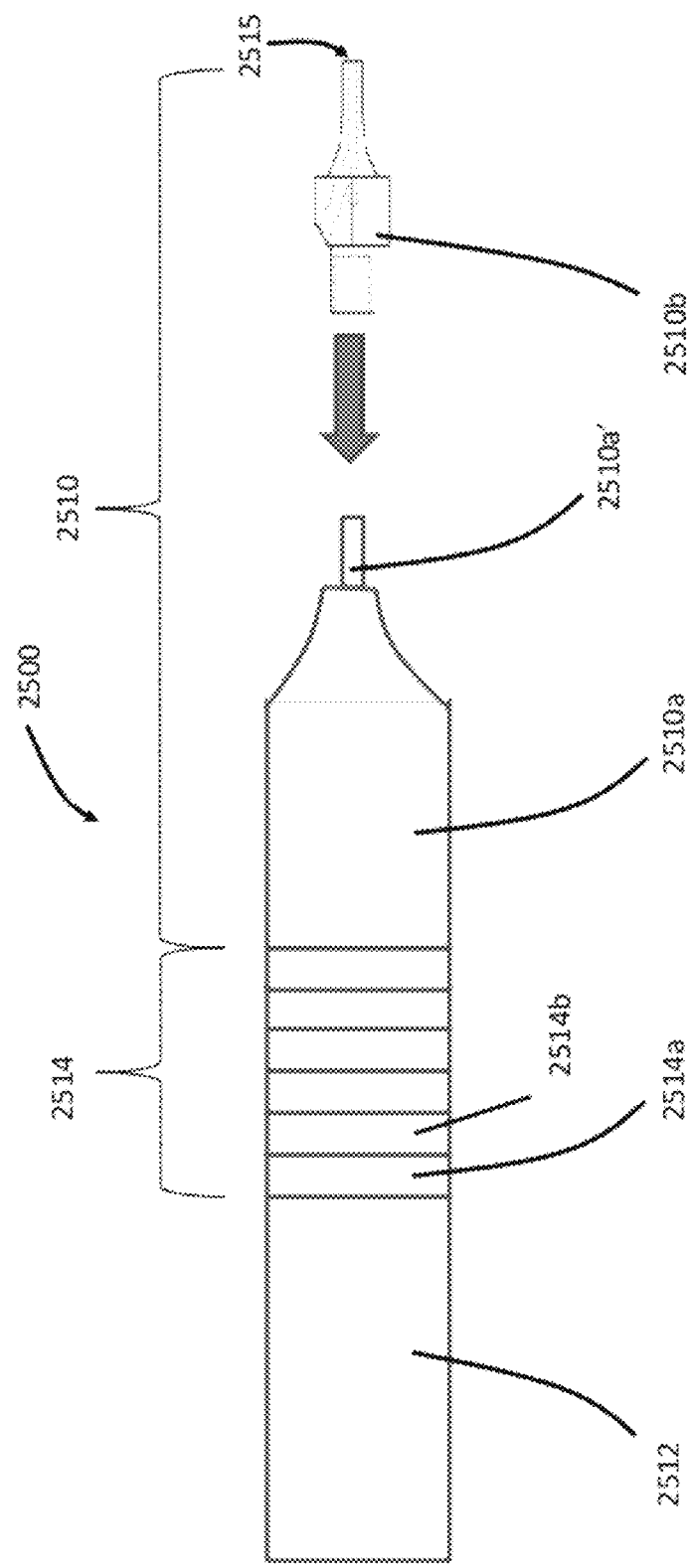
FIGS. 25a-b shows a side view of a device of an additional embodiment of the present invention.
Figure 25B:
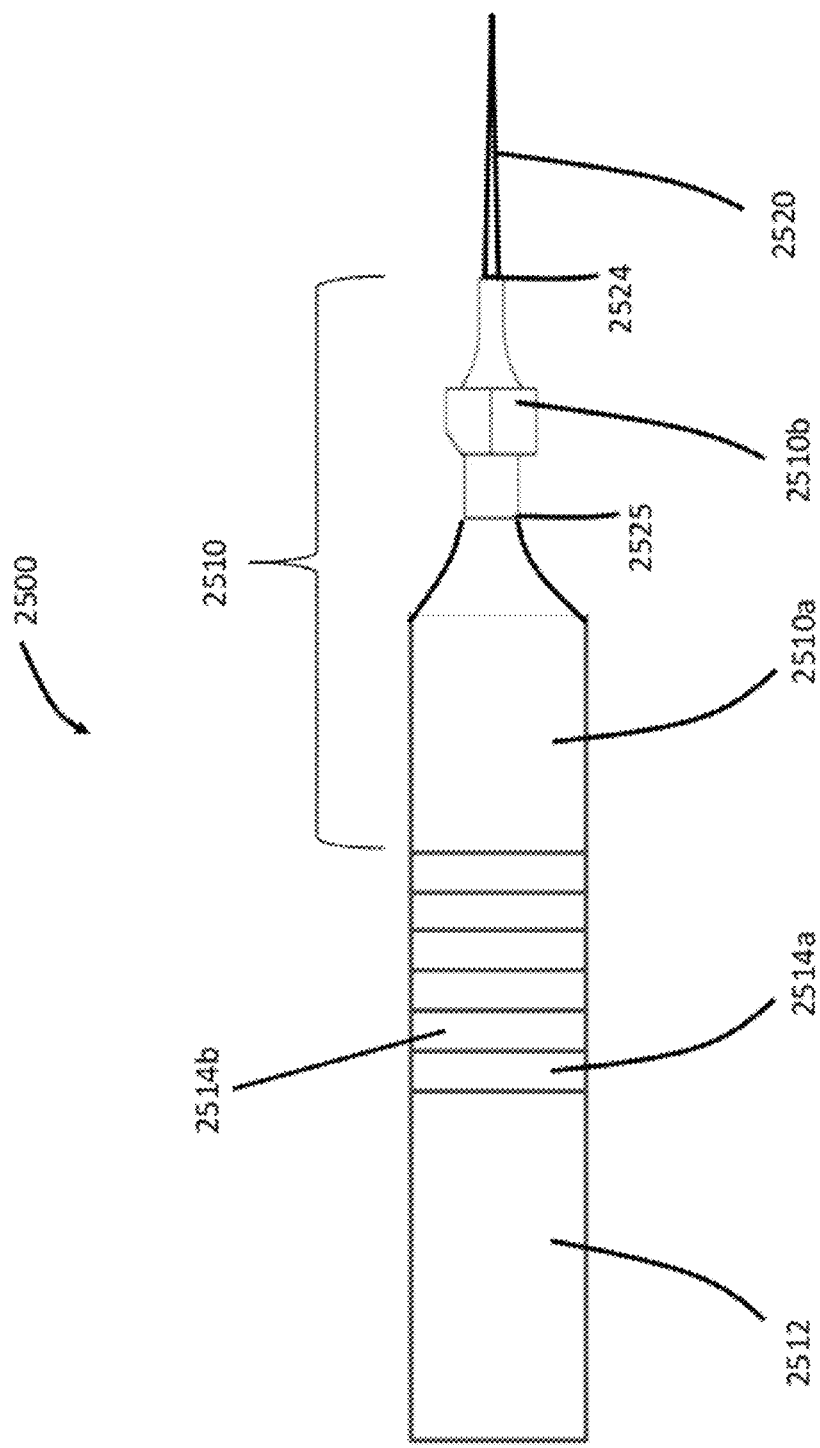
Figure 25C:
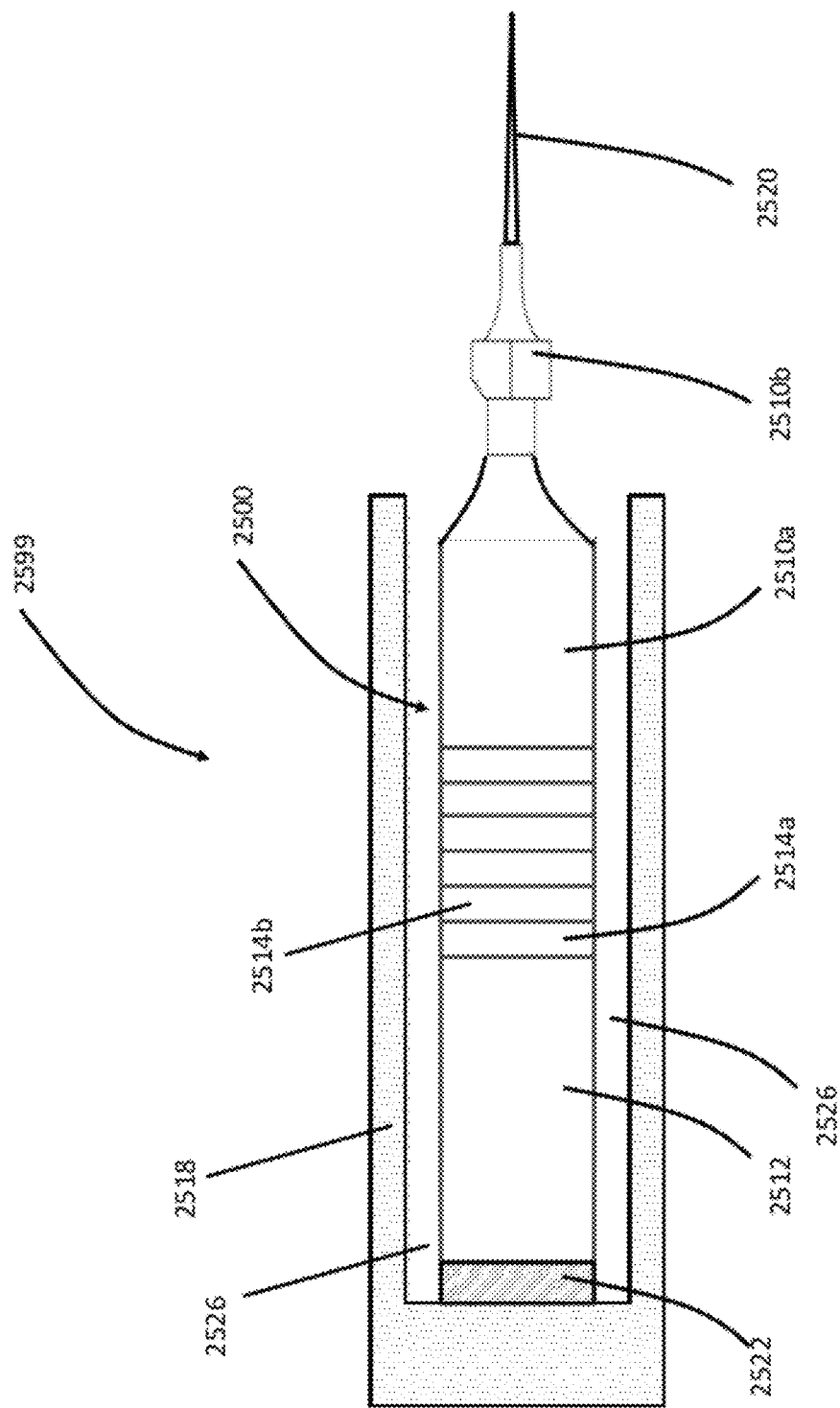
FIG. 25c shows a side view of a device of an additional embodiment of the invention.

In an embodiment, a device such as device 2599 for use with subsystem 2400 can further include a force sensor 2522 in mechanical communication with an actuator 2500, as shown in FIG. 25c and described in more detail below. The force sensor 2522 can also be in electronic communication with the feedback subsystem for activating said feedback subsystem. In one embodiment, a separator mass (not shown) can be formed between the force sensor and the actuator. In one embodiment, the force sensor is a piezoelectric ring adjacent to a proximal end of the actuator's rear mass and formed between the rear mass and an outer handle in which the actuator is completely or partially disposed.

As discussed above, for example with respect to FIGS. 20a-20c, the driving actuator usable with feedback subsystem 2400 can include a voice coil 902/906/904. The voice coil can be coupled to the penetrating member 20. The voice coil can convert electrical energy into oscillatory motion when it is energized. The driving actuator can be a pneumatic or a fluidic actuator (not shown). Accordingly the feedback subsystem 2400 can be in electrical communication with a voice coil, pneumatic or fluidic actuator.

As discussed above, a method for reducing the force needed to penetrate living being tissue is provided, and is generally illustrated as a flow chart in FIG. 22. While the operator can manually control the force of the medical device against tissue, the force can be controlled, and/or reduced, based on the tissue being encountered during the insertion of a sharps member that is reciprocated. The method can include the step of establishing characteristic electromechanical property changes of a vibrating reference member having a sharps member that passes through various tissues that correlates said changes with particular tissues. The characteristic electromechanical property changes can be established by correlating changes within a single electromechanical property, such as tracking impedance magnitude vs. time, or between several electromechanical properties such as comparing each of impedance magnitude and penetration force vs. time. Such changes can be gathered, stored and analyzed, such as in the graphs shown in FIG. 23 and FIGS. 29-31.

Particular changes and/or comparison of changes can be correlated to a particular event and established as a predetermined characteristic of electromechanical property or properties. For example, empirically gathered data can be stored as a predetermined value or predetermined values in a database and that is accessible by a feedback system (such as that described in embodiments herein). As the subsystem gather signals and uses or stores the gathered signal as data representative of electromechanical properties of a reciprocating device in operation, the gathered electromechanical property or properties (or changes within or between the properties), can be compared to the characteristic or predetermined values stored on the database. In other words, the real-time electromechanical properties can be correlated to an event which is known, based on empirical results, to a particular event. For example, the subsystem can gather data, compare the data to values on a database representative of a known event, such as penetration through particular tissue, for example penetration into the epidural space, and the subsystem can respond based on whether the real-time collected data matches the predetermined data within a predetermined error value.

Continuing with a description of the method described in FIG. 22, in some embodiments, it includes a "start" step 2202 of reciprocating the sharps member against the living being tissue using a reciprocating actuator that converts electrical energy to reciprocating motion. The sharps member can be reciprocated by providing power to an actuator, such as Langevin actuator 100, coupled to the sharps/penetrating member/introducer 20, such as described in steps 2202-2204. The method can include the step of detecting a change in the characteristic electromechanical property as described above. The step of detecting a change in the characteristic electromechanical property can be performed by the feedback subsystem 2400, based on controlling software that includes a predetermined threshold change to which the measured electromechanical properties measured in step 2206 are compared. Thus, the method can include the step 2208 of referencing a database that contains predetermined values corresponding to electromechanical properties or change thereof that are representative a particular event, particular tissue, or particular property of a material that the device's penetrating member is in contact with.

The subsystem can be programmed to perform step 2210 of comparing the detected electromechanical property (or properties), or change in electromechanical property (or properties) against said the predetermined correlation. In step 2210, for example, the subsystem can determine whether the measured input value or values gathered in step 2206 matches a reference parameter. Such a comparison can be based on known statistical algorithms for comparing gathered data with stored corresponding data and can be performed by a microprocessor controlled by the software.

Depending on the results of the comparison, the method can perform a repeat of step 2206 or continue to step 2212. If, for example, the feedback subsystem determines that a measured electromechanical property, or change thereof, does not match a corresponding characteristic of the property stored in the database, the subsystem can proceed by repeating step 2206 and again measure an updated electromechanical property. Otherwise, the method can include the step 2212 of sending a signal to an output device, for example, to indicate to an operator of an embodiment described herein the type of tissue that is being currently encountered by, for example, the sharps member, based on the change in the characteristic electromechanical property. In one embodiment, the step of indicating to an operator comprises displaying or informing the operator of an identity of the tissue being currently encountered by said sharps member.

The method can include the step of automatically controlling or modifying the force being applied to said sharps member. In one embodiment, the step of automatically controlling the force being applied includes de-energizing the sharps member as shown in step 2216. In one embodiment, the step of automatically controlling the force being applied includes maintaining or changing a frequency at which sharps member is reciprocated as in step 2214.

As discussed above, the method described in the flowchart of FIG. 22 can be used for the detecting of the passage of the penetrating member through living being tissue. However, the feedback subsystem can include visual or tactile response indicators. For example, in an embodiment, the step of detecting the passage of the penetrating member through the living being tissue can include the movement of a plunger within a fluid-containing syringe that is in fluid communication with a channel within said penetrating member, such as via the sideport SP in communication with first channel 126. In other words, the syringe can be in electrical communication with the feedback subsystem and can provide the subsystem with electronic signals corresponding to movement of the plunger or a pressure loss within the syringe to complement the other data, such as electromechanical characteristics, that can be used for sensing a corresponding event.

Additionally, a sensor, such as a pressure transducer, blood flow detector, thermocouple can be used to sense fluid pressure within the sharps/penetrating member of the device, and can be in electronic communication with the feedback subsystem to complement the other gathered data, such as electromechanical characteristics. For example, in one embodiment, the step of detecting the passage of the penetrating member includes the use of at least one sensor that monitors at least one of a characteristic electromechanical property. The at least one sensor can be in communication with a channel of said penetrating member. The at least one sensor can provide an output that controls the feedback subsystem which can control the operation of a controller or switch that provides electrical energy to said reciprocating actuator. In one embodiment, the reciprocating actuator caused to reciprocate in the disclosed method can be a Langevin actuator that includes a horn section formed of a first portion detachably connected to a second portion as described below.

Transducer, Needle, Feedback and Control Design for Reduced Penetration Force

In some embodiments, the actuators described herein can be operated at various frequencies, including ultrasonic frequencies as discussed above. For example, the actuators can be operated to actuate at a frequency, or various frequencies in the range of 19-50 kHz, 20-25 kHz, 21-30 kHz, 21-24 kHz, 24-30 kHz, 28-35 kHz, and 40-50 kHz. The medical device can also be provided with driving voltages of 100-500 $V_{pp}$, 100-200 $V_{pp}$, 250-450 $V_p$ As shown in FIGS. 25*a-c*, in an embodiment, the invention includes a device, such as a medical device for penetrating through living being tissue. The device can include an actuator 2500, such as a Langevin transducer. The actuator 2500 can include a displaceable member 2510, such as a horn capable of focusing resonating energy provided by a piezoelectric stack portion 2514. The displaceable member can be formed of a first portion 2510*a* detachably connected to a second portion 2510*b*, a rear mass 2512, and the piezoelectric stack 2514 which is formed between the displaceable member 2510 and the rear mass 2512. The device can also include a sharps member 2520 which is coupled to a distal end 2515 of the second portion 2510*b*. The device can also include an electrical power feedback subsystem (not shown in FIGS. 25*a-c*), such as the feedback subsystem 2400 described above, for automatically controlling the power to the actuator based on a sensed condition. One reason that the displaceable member 2510 includes a first portion detachably secured to the second portion is so that a large portion of the actuator can be reused and the second section 2510*b* can be disposed of or sterilized for repeated use. Particularly, the second section 2510*b* can be acoustically matched to function, in conjunction with portion 2510*a*, substantially as a single piece horn. Were the device to include a single piece horn instead of a multi-section horn, it might not be possible for the actuator to be reusable as it could come into contact with bodily fluid and would completely require sterilization (which could potentially damage the piezoelectric stack).

The second portion 2510*b* can function to accept the sharps member 2520, such as a needle, so that can be secured permanently. The sharps member 2520 can be secured to the second portion 2510*b* prior to the second portion being releasably secured to the first portion 2510*a*. Alternatively, the sharps member 2520 can be secured to the second portion 2510*b* after the second portion has been releasably secured to the first portion 2510*a*. The second portion 2510*b* can be configured to accept a sharps member 2520 directly at the second portion's distal end. The second portion 2510*b* can be configured to accept a hub (such as the hub of a disposable needle), and become detachably connected to the hub. In other words, a hub can be detachably connected to the second portion 2510*b* such that the hub is disposed between the second portion 2510*b* and a sharps member.

Piezoelectric elements 2514*a*, 2514*b* can comprise annular piezoelectric elements. When attached to one another using methods known in the art, the piezoelectric elements form a channel through which a shaft portion (not visible) of the horn/displaceable member 2510 extending proximally from the first portion 2510*a* is passed when assembling the actuator. The shaft portion mates with rear mass 2512 via male threads on an end portion of the shaft that match with female threads in the rear mass 2512. The piezoelectric stack 2514 is configured to be pre-stressed due to being compressed by the first portion 2510*a* and rear mass 2512 upon threading the shaft portion into the corresponding threaded portion of the rear mass.

Because lower acoustic impedance transfers energy more efficiently, the actuator 2500, for example a Langevin transducer, must include acoustically matched components for rear mass 2512, piezoelectric stack 2514, first portion 2510*a* and second portion 2510*b*. For example, horn 2510 and rear/back mass 2512 are configured such that when second portion 2510*b* of the horn is attached to first portion 2510*a*, heating at, for example, the proximal interface 2525 is kept to a minimum. Energy lost to heating can be caused by the use of a conventional needle hub that has not been configured to ultrasonically actuate when attached to first portion 2510*a*. Such an energy loss can serve to reduce displacement at the tip of sharps member 2520. Additionally, second portion 2510*b* can be configured to be of certain dimensions. For example, second portion 2510*b* can have a length of about 0.760" and a width of 0.313", however such dimensions do not limit the configuration. Additionally, second portion 2510*b* should include a channel through which fluids such as medications or bodily fluids, or solids such as a catheter tube can be passed.

Figure 30:
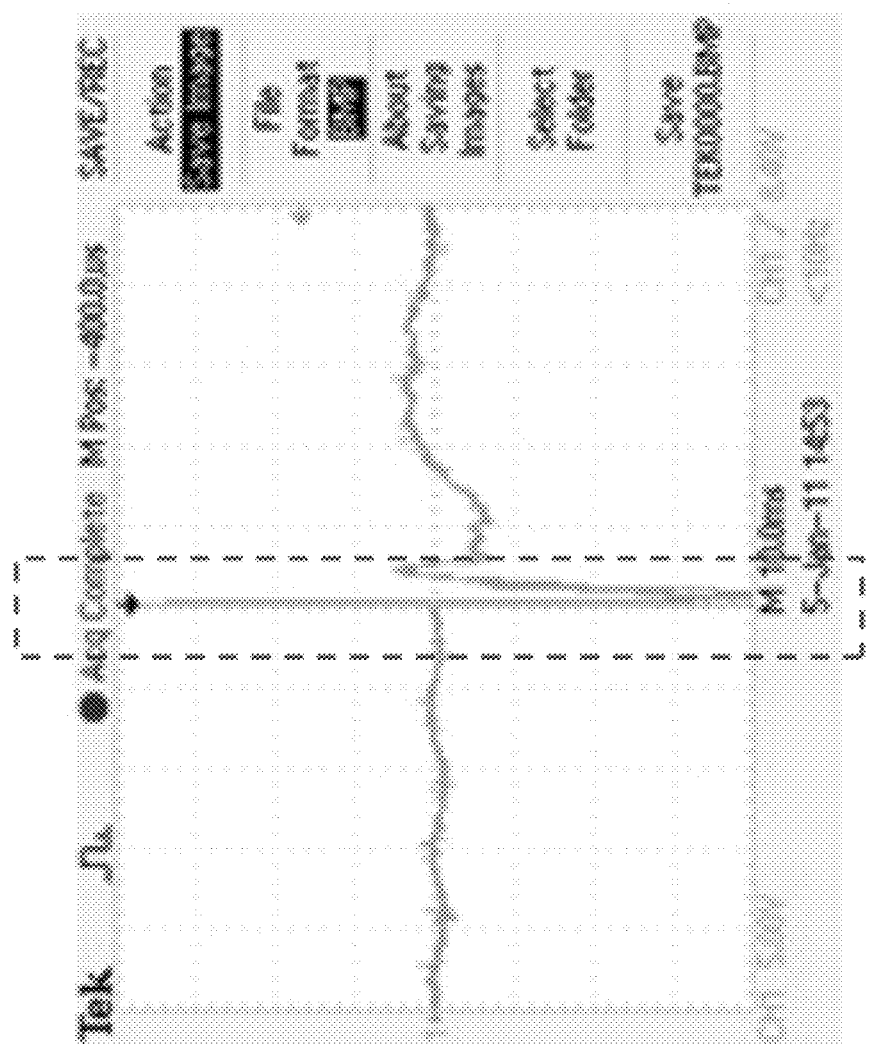
FIG. 30 is a graph of test data (e.g., impulse voltage response) of a reference device as a sharps member thereof penetrates into the epidural space.

In one embodiment, the density of the horn can be less than the density of the rear mass. In one embodiment, the first portion 2510*a* of the horn and the rear mass can be the same material and the second portion 2510*b* of the horn can be a different material that the second portion 2510*b* of the horn. For example, rear mass 2512 and first portion 2510*a* can be made of titanium while the second portion 2510*b* of the horn can be made of stainless steel (such as 304 stainless steel) or aluminum (such as 7075 T6 aluminum). Second portion 2510*b* can also be polymer, but must be capable of accepting ultrasonic energy without failing. Second portion 2510*b* should be configured to be releasably attached to 2510*a*, but should not be capable of loosening simply by activating the device. The components of actuator 2500 can be acoustically matched such that, for example, upon reciprocating at frequencies between 19 kHz-25 kHz, temperature does not rise above 60° C. at a metal-metal interface. As shown in FIG. 25*c*, the medical device can include a force sensor 2522 disposed at a proximal end of the driving actuator. The force sensor 2522 can include a piezoelectric ring. The force sensor can be a compact force sensor integrated into a handpiece 2518 in which the actuator is completely or partially disposed. The force sensor can include a non-activated (i.e., non-actuating or sensing) piezoelectric stack comprised of a plurality of piezoelectric rings. A separator mass, such as a steel separator mass, or in the case of the Langevin transducer, the rear-mass, can be formed between piezostack 2514 and sensing stack 2518. As the device is brought into contact with an opposing force, such as tissue, the opposing force can be measured by the force sensor as shown in FIG. 30.

The actuator can be disposed in a volume defined by the handpiece 2518. A gap 2526, which is a portion of the volume defined by the handpiece, can separates the handpiece and the actuator from one another, either partially or completely, can be filled with a vibration damping material such as silicone. The vibration damping material can be used to secure the actuator and to minimize the transfer of vibration caused by activation of the actuator on the user gripping the handpiece 2518.

As discussed above, the device can include a feedback subsystem. The feedback subsystem can be capable of detecting electromechanical properties. For example, feedback subsystem can include a phase angle detector for detecting passage of a distal end of the sharps member 2520 into, for example the epidural space of a living being or for detecting changes in device operation conditions as the device is exposed to various media. Detection can be based on a measured phase lag, or change in the measured phase, of a control signal of the medical device.

Figure 28:
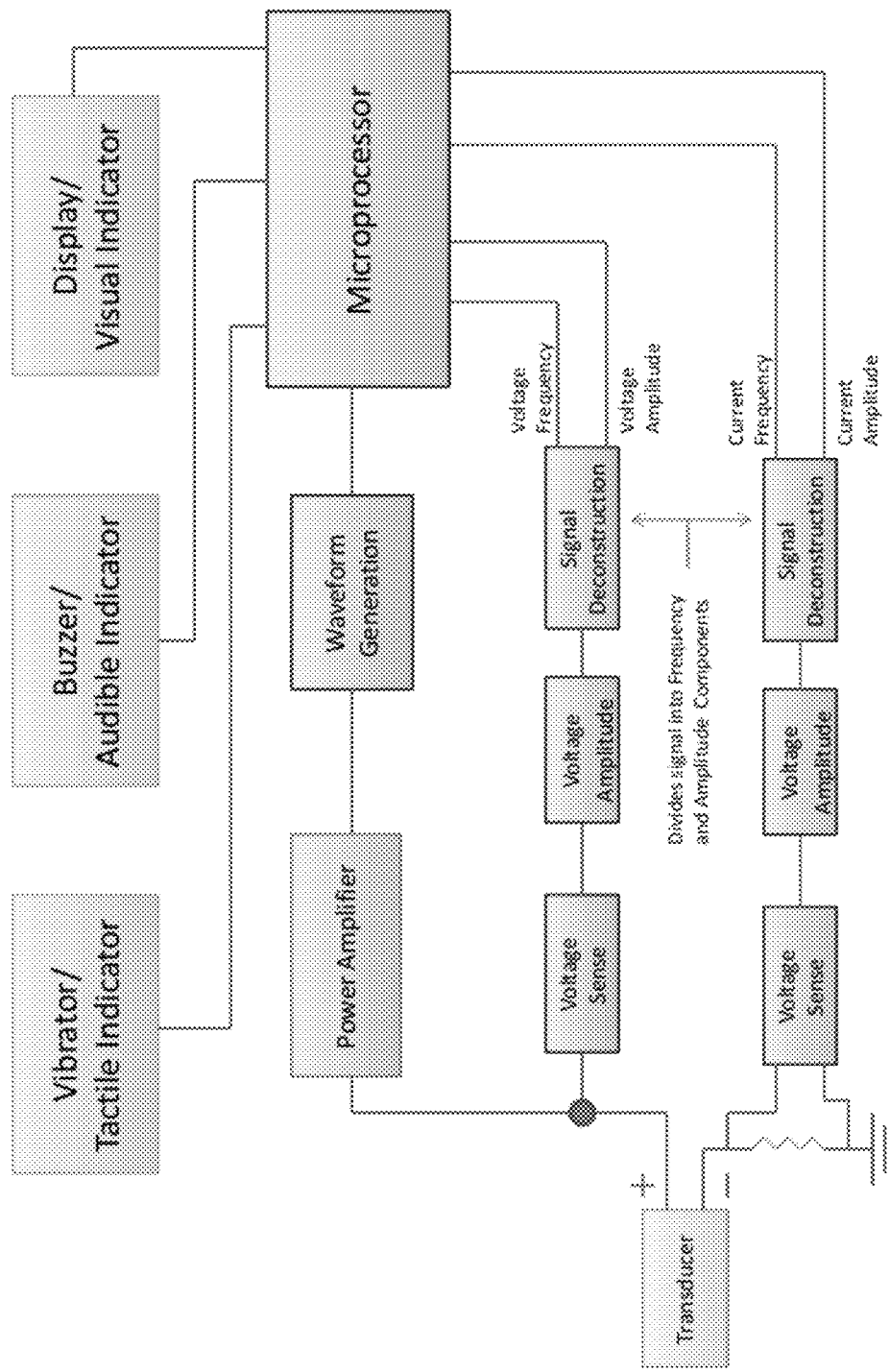
FIG. 28 is an exemplary schematic of a feedback subsystem for use in the various embodiments of the present invention.
Figure 29:
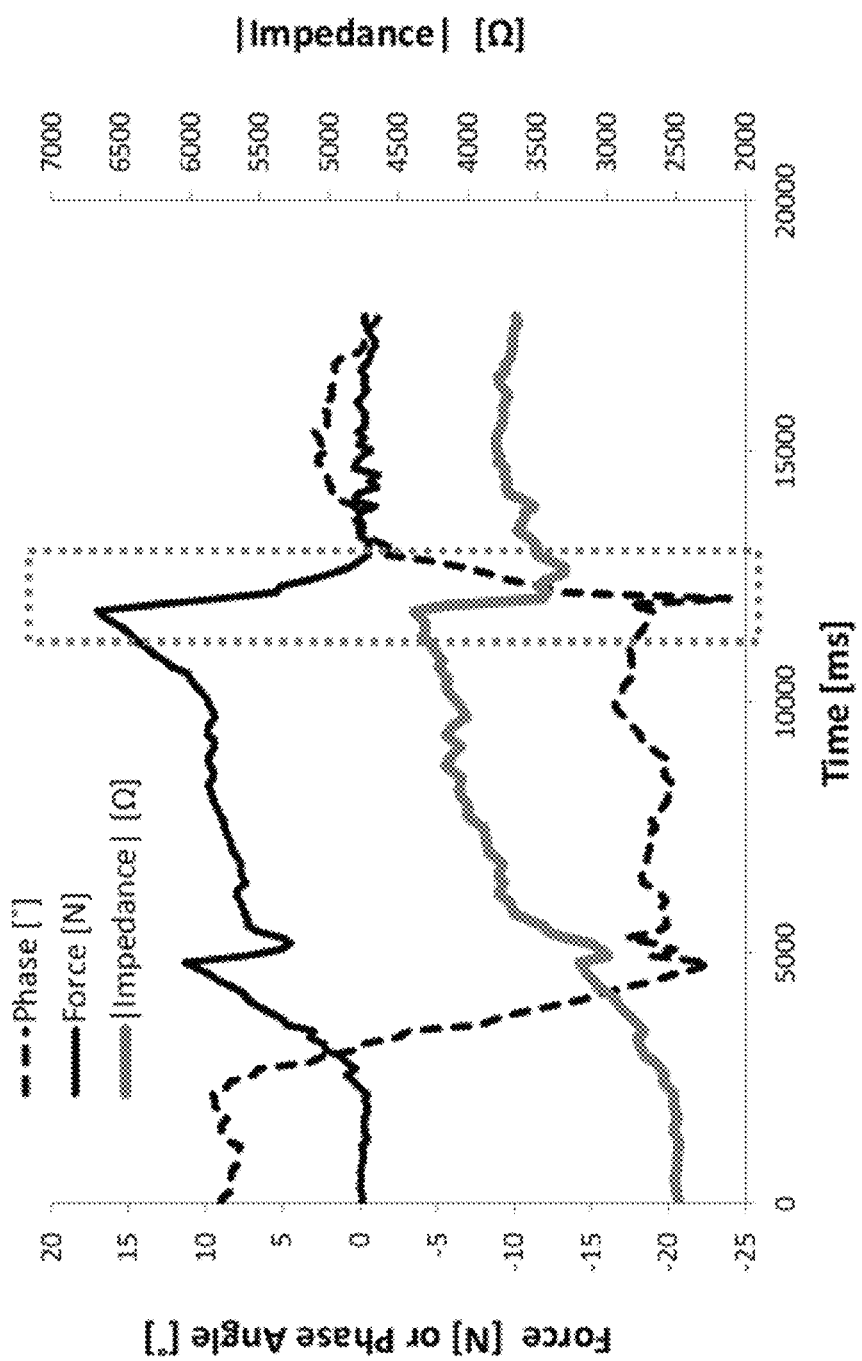
FIG. 29 is a graph of test data (e.g., Resonance Frequency, Impedance Magnitude, Phase Angle, Penetration Force) of a reference device versus time (msec)

In an embodiment, the feedback subsystem can include a voltage detector for detecting passage of the distal end of said penetrating member into the epidural space based on a voltage of a control signal of said medical device. In one example, the feedback subsystem can correlate abrupt changes in phase angle (as shown in FIG. 29) and abrupt changes in voltage generation from the force sensor (as shown in FIG. 30) to stored values that correspond to an event, such as a known event, such as penetration into the epidural space or the filling of the sharps member with cerebral spinal fluid upon penetration into the subarachnoid space. The feedback subsystem 2400, upon comparing the measured values with the stored values, can automatically adjust the power delivery to the actuator. One example of the feedback subsystem 2400 is shown in FIG. 28 which provides different detail than the subsystem shown in FIG. 24.

As shown in FIGS. 26*a-c*, the second portion 2510*b* includes a channel 2504 disposed therein. The channel 2504 can be formed in communication with at least two openings 2501, 2502 formed on an outer surface of the second portion 2510*b*. Opening 2502 can be formed by machining a flat surface by removing material from a corner of an outer grippable portion 2509, which has a polygonal cross section, and then drilling into the flat surface. The second portion 2510*b* can include a third opening 2503 that is not in communication with the at least two openings. In other words, opening 2503 can be formed so as to accept a distal end of the first portion 2510*b*. The channel 2504 comprises a first section that, at opening 2501, accepts a proximal end of the sharps member 2520. The channel 2504 can include a second section that, at opening 2502 can accept material capable of being introduced to an inner volume of the sharps member (e.g., fluids, medicines, catheters, or the distal end of a syringe). The second portion 2510*b* can be configured, with or without the sharps member attached, as a disposable or single-use item. In other embodiments, the sharps member can be configured to be detachably secured to the second portion 2510*b*, such that the sharps member can be disposed of after use, and the second portion can be reused, for example, after undergoing sterilizing in an autoclave.

The channel that communicates with the two openings can include a bend such that a first section of the channel in communication with opening 2501 and second section of the channel in communication with opening 2502 are separated by an angle α. Angle α should not be so great so as to prevent the insertion of a catheter through the second opening, can traversal of the catheter through the channel, and the catheter's exit through the first opening 2501. For example, the bend angle α can be greater than about 0° to about 90° from an axis that runs through the center of the first opening as shown by the vertical dashed line in FIG. 26*c*. Preferably, the bend angle α can be about 45° to about 55°.

In order to, among other things, prevent bodily fluids, medications or other materials from coming into contact with the first portion 2510*a* during use of the device 2599, the first portion 2510*b* is configured such that third opening 2503 is not in fluidic communication with the channel 2504, first opening 2501 and second opening 2502. In other words, a volume 2508 defined by sidewall 2506 that extend distally from the third opening 2503 does not extend so far as to extend to any portion of channel 2504. However, to ensure that the second portion 2510*b* can be securely attached onto the first portion 2510*b* (although the two portions may still be released from one another), the volume 2508 should extend distally from opening 2503 at a length equal to or greater than a length of the distal tip 2510*a*' of the first portion, which can be threaded to couple with matching threads on sidewall 2506.

In one exemplary method of using the device 2599, a medical procedure as cerebral spinal fluid collection is performed by a user/clinician on a patient. Prior to powering the device, the user attaches the second portion 2510*b* (with sharps member already attached thereto) to the first portion 2510*a*. If a sharps member is not already attached to the second portion 2510*b*, the user also attaches a sharps member at the distal first opening 2501 of second portion 2510*b*. While for this example, the sharps member would preferably be a spinal access needle, in other procedures the sharps member can be, for example, an epidural needle such as a Tuohy needle, catheterization needle, venous access needle, bone biopsy needle, or other sharp object for use in penetrating tissue and other bodily materials.

The user provides power to the device by energizing it. Upon energizing the device, for example, by turning a power switch to an "on" position, a controller's microprocessor having been preprogrammed, initiates a power-on algorithm that includes delivering a voltage to the piezoelectric stack 2514. The delivery of a voltage causes the piezoelectric stack to expand which causes other portions of the actuator to expand, such as at a distal tip of the second portion 2510*b*.

Voltage can be provided to the actuator at various predetermined signaling patterns, such as a continuous sinusoidal pattern at a particular frequency or varying frequencies. In some embodiments, the voltage can be delivered to the actuator in a pulsed mode in which the voltage is delivered in groups of continuous sinusoidal patterns, each group consisting of at least one frequency and each group being delivered at least one a predetermined frequency.

Upon powering up, the microprocessor can initiate an algorithm for determining a reference resonant frequency, for example, before the device penetrates tissue. To determine the reference resonant frequency, the microprocessor can perform a frequency sweep as shown in FIG. 32*a*, from which the impedance magnitude (voltage amplitude to current amplitude ratio) and phase (i.e., phase angle of impedance is simply the relative phase between the voltage and current signals) can be determined For example, a frequency sweep can begin at a frequency ($F_{t1}$) in which a voltage is applied and a corresponding current is measured by, for example, an impedance analyzer connected to the controller. The frequency can be subsequently increased by a certain increment, with each of impedance magnitude and phase being measured at additional frequencies, such as at frequencies Ft2, Ft3 as shown in FIG. 32*a*, through to a maximum frequency in a predetermined range of frequencies. The impedance analyzer can identify the impedance at a given frequency, and a microprocessor connected to the impedance analyzer can store the measured values relative to the output current and output frequency. As shown in FIG. 32*b*, the resonant frequency (F0) of the device is selected as the frequency at which the corresponding impedance measured at each frequency in the sweep range is a minimum. In addition to, or alternatively, the resonant frequency can be selected as the frequency corresponding to a predetermined phase angle (e.g. 0) that corresponds to the typical minimum impedance of the device 2599. The frequency corresponding to the minimum impedance magnitude occurs (or corresponding to the measured phase angle that matches a predetermined target phase angle) is determined to be a standard reference frequency at which the device will be initially driven to ensure maximum displacement. Accordingly, the controller provides power to the device at the reference frequency.

As the sharps member is brought into contact with and penetrates tissue, the impedance spectrum of the device will change. FIG. 32*c* illustrates a hypothetic shift in the impedance spectrum of the device as it encounters resistance, such as tissue. FIG. 32*c* shows that if the device is continued to be driven at the initial reference resonance frequency, the impedance magnitude would increase while the impedance phase would decrease or more negative. Conversely, as shown in FIG. 32*d*, if the characteristic impedance spectrum were to shift in the opposite direction, both the impedance magnitude and phase would increase in the positive direction, provided the shift were not too great.

In order to adjust the driving frequency to match the new resonant frequency (identified as F1 FIG. 32*d*), the controller can increase the driving frequency until the impedance analyzer measures that the phase has returned to the target phase (eg. 0) and/or until the impedance minima is again detected during a secondary sweep of the frequency through a specified range that at least overlaps with the initial range, is the same as the initial range, or a smaller subset of frequencies within the initial range.

Figure 27:
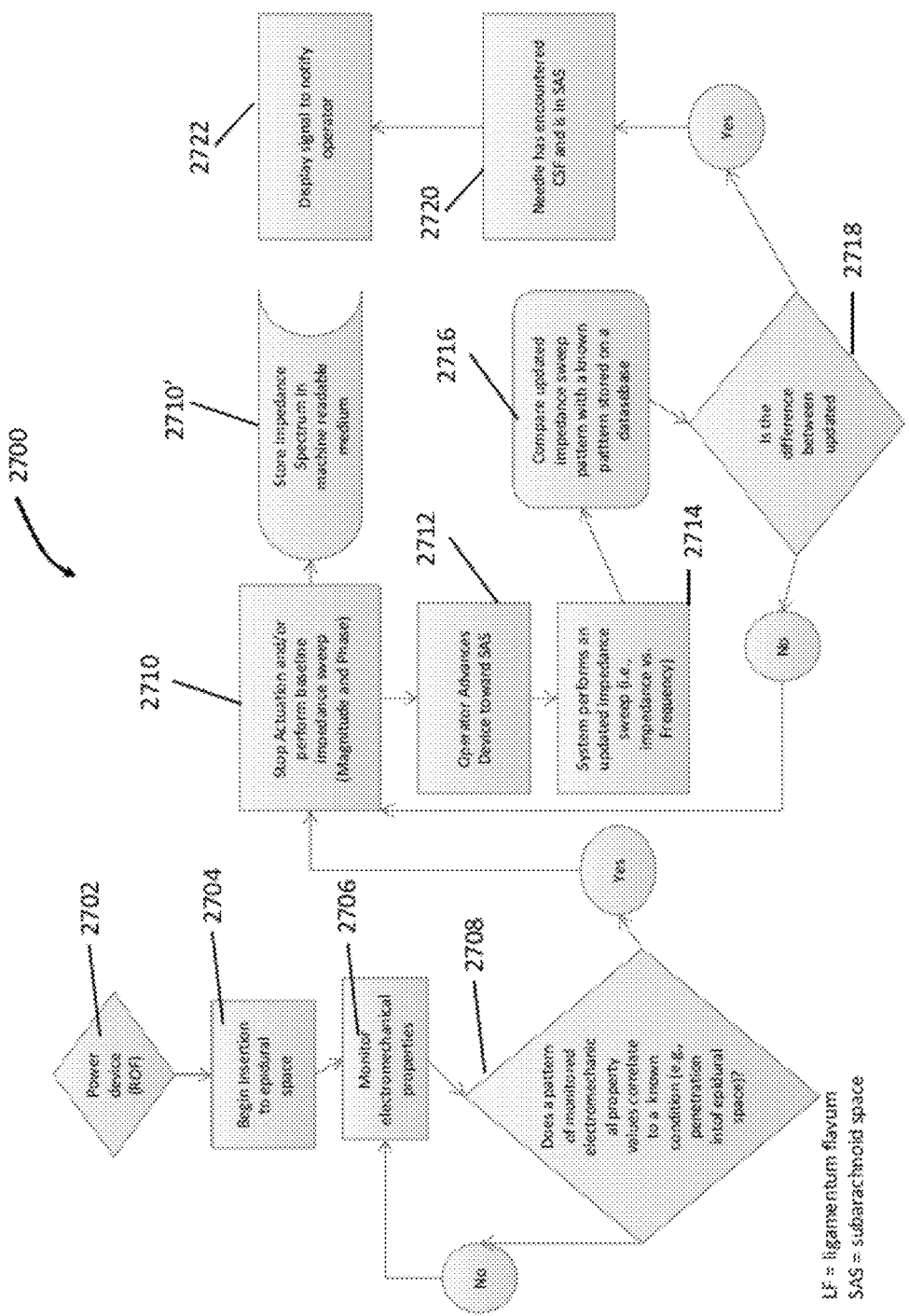
FIG. 27 is a flow diagram of how an alternate feedback subsystem of the present invention operates.

Thus, as shown in FIG. 27, a method for penetrating a living being is described. As discussed above, a medical device such as device 2599 is powered and a controller in communication therewith performs an initial frequency sweep. Initially, the device is powered/energized at step 2702 to actuate/vibrate the device's sharps member 2520 at a reference resonance frequency that provides for a reduction of force initially required to penetrate through a medium. The resonance frequency can, for example, be selected from the range of 20-21 kHz or 30-32 kHz. However, the resonance of the device can shift with changes in temperature and mechanical loading. For example, this shift can be up to about 3 kHz, which if the operating frequency is not adjusted, it will operate in a non-efficient operating mode. Accordingly, as the device is moved toward the epidural space, as in step 2704, by the clinician, or an external source of motion, the sharps member 2520 is eventually brought into contact with the patient's tissue. As described above, the driving resonance frequency will be adjusted so as to maintain resonance.

Accordingly, as the device initially penetrates into a living being, such as insertion in a direction toward, for example, the epidural space as shown in step 2704, and the resonance value shifts a feedback subsystem performs a monitoring algorithm that measures electromechanical properties and adjusts the resonance frequency according to a predetermined algorithm. In other words, the device monitors vibrational response as the needle penetrates through tissue.

The vibrational response can be monitored, for example via a feedback system that automatically tracks electromechanical properties of the device, such as impedance, as shown in step 2706. This can be done, for example, by programming the microprocessor of FIG. 28 to perform a series of impedance or resonance frequency measurement sweeps (e.g., impedance value v. frequency; resonance frequency v. time; phase angle vs. frequency; phase angle shift vs. time), storing and/or displaying corresponding measured values, and/or comparing those measured values to known values, and/or comparing the measured values to a known relationship between values. In an embodiment, the processor can be programmed to identify characteristics of values related to electromechanical properties of the device as it vibrates through tissues/materials/fluids/gases of a being (e.g., living being).

For example, the task of tracking a resonance frequency can be accomplished by first causing the controller to electronically perform a sweep across a range of frequencies. The range of frequencies can be set by the operator, or can be preset. For example, the controller can be programmed or set by the user to perform a sweep across a range of frequencies such as 19.5 kHz to 21.5 kHz. The frequency at which the device produced the maximum response (i.e., largest displacement of the sharps member's distal end which will typically occur at a minimum measured/calculated impedance magnitude), the controller can be set to operate the device's actuators at the corresponding resonance frequency. While a tracking cycle, such as that described above, is necessary to maintain efficiency (i.e., so that the driving signal from the controller to the actuator can change as fast as the resonance shift changes), it would take too long for the device's electronics to constantly perform frequency sweeps. Thus, in addition to or alternatively, a continuous tracking method can be employed as described below. For example, the feedback subsystem can be programmed to monitor the magnitude and phase of the voltage and current signals, which can then be used to calculate a resonance frequency. Upon calculating an updated resonance frequency for each cycle of monitoring the magnitude and phase of the voltage and current signals using the continuous tracking method, or at given time intervals (such as running a new calculation and adjusting the driving frequency at a rate of 5-10 Hz; i.e., the resonance frequency can be updated 5 to 10 times every second), the controller can use the updated frequency to compensate for a shift in resonance.

In an embodiment, the measurements can provide values that are the result of physical interactions of the sharps member with materials (e.g., as a hollow sharps member is filled with and/or surrounded by tissues/materials/fluids/gases). The processor can determine the resulting device impedance or resonance frequency signal curves as discussed above and can determine the location of corresponding maximums and minimums, and/or can calculate slopes. These calculations can be further utilized to determine characteristics of the tissue, the location of the needle within a being, or to automatically adjust the power required for the needle to maintain a particular driving pattern, for example, a resonance frequency. As the user continues to move the powered device toward a desired location within a living being, the microprocessor can monitor transient changes in impedance to maintain resonance and/or store the measured electromechanical properties as patterns or graphical representations, and compare the pattern of monitored/measured electromechanical properties to a pattern corresponding to a known condition which can be stored in a database accessible by the processor in the feedback system, as shown in step 2708.

In other words, via impedance sweeps (wherein signals are generated by the device's electronics and stored in a connected memory, and/or generated and displayed to the user on a connected display, wherein the signals are translated into corresponding numerical values representative of impedance and/or frequency; or another value that identifies the tissue being penetrated through) performed by the device's electronics, the device's connected controller (such as a microprocessor) can be programmed to automatically track the real-time impedance magnitude at a given resonant frequency (or particular driving frequency) of the device as the needle advances toward, or is brought adjacent to, within, and through the ligamentum flavum. Via monitoring of selected electromechanical properties as a function of, for example, time, the device's microprocessor can also build a catalog of stored patterns corresponding to changes in the electromechanical properties and can compare these changes to stored changes representative of a known condition. In one example, the microprocessor has measured and stored values in a memory, the values corresponding to resonance frequency, impedance magnitude, phase angle and/or penetration force (such as provided by a force sensor in contact with the device and the feedback system). The electromechanical properties can be measured simultaneously, for example using LabBiew software (National Instruments, Austin, Tex.), a shimpo 20 lb capacity force gauge model FGV (Itasca, Ill.) and an HP4194A Impedance analyzer. The microprocessor can then retrieve the stored/measured values and compare how the values have changed relative to other values corresponding to a similar electromechanical property or to other electromechanical properties. The microprocessor can then compare the measured/stored values to a known pattern of values, such as the pattern shown in FIG. 29 indicative of a known condition, such as penetration through the ligamentum flavum and advancement of the sharps member into the epidural space. The microprocessor can then either determine that the measured values are similar to or different from the referenced pattern of values in the database, based on whether the comparison falls within a mathematically predetermined error value.

Additionally, during all steps when the device is powered, feedback subsystem continuously attempts to maintain the driving frequency at a resonant frequency as discussed above.

Thus, when one of the above mentioned sweeps is performed and signals are collected and stored in a machine readable medium, such as a computer memory, as the needle tip penetrates the ligemantum flavum, the device electronics can be configured to be manipulated by software stored in a computer to automatically powerdown the device upon generating and storing a value that compares statistically equivalent to a known value indicative of entry of the needle into the epidural space. Such a method of operation that relies on the electromechanical properties of the device is generally described in related U.S. Provisional Application Nos. 61/441,500 filed on Feb. 10, 2011 and, 61/441,677 filed on Feb. 11, 2011, both of which are incorporated by reference herein in their entireties.

Continuing in FIG. 27, upon the needle reaching the epidural space as it is advanced by the user, the device's actuators can be powered down (and/or some or all of the actuation of the needle can be terminated) as discussed above and shown in step 2710. The device, via its feedback subsystem and associated power controller, can then automatically perform a fresh baseline impedance sweep (e.g., impedance phase angle vs. Frequency) as described in step 2710. Alternatively, the clinician can manually cause the device's electronics to execute a baseline impedance sweep (e.g., clinician can depress an electronic switch programmed to initiate a baseline sweep). Upon generation and detection of electronic signals during the sweep(s), values of the electronic signals are assigned to corresponding impedance values (e.g., impedance phase angle) and the measured baseline impedance spectrum is stored in the device's memory.

Figure 31:
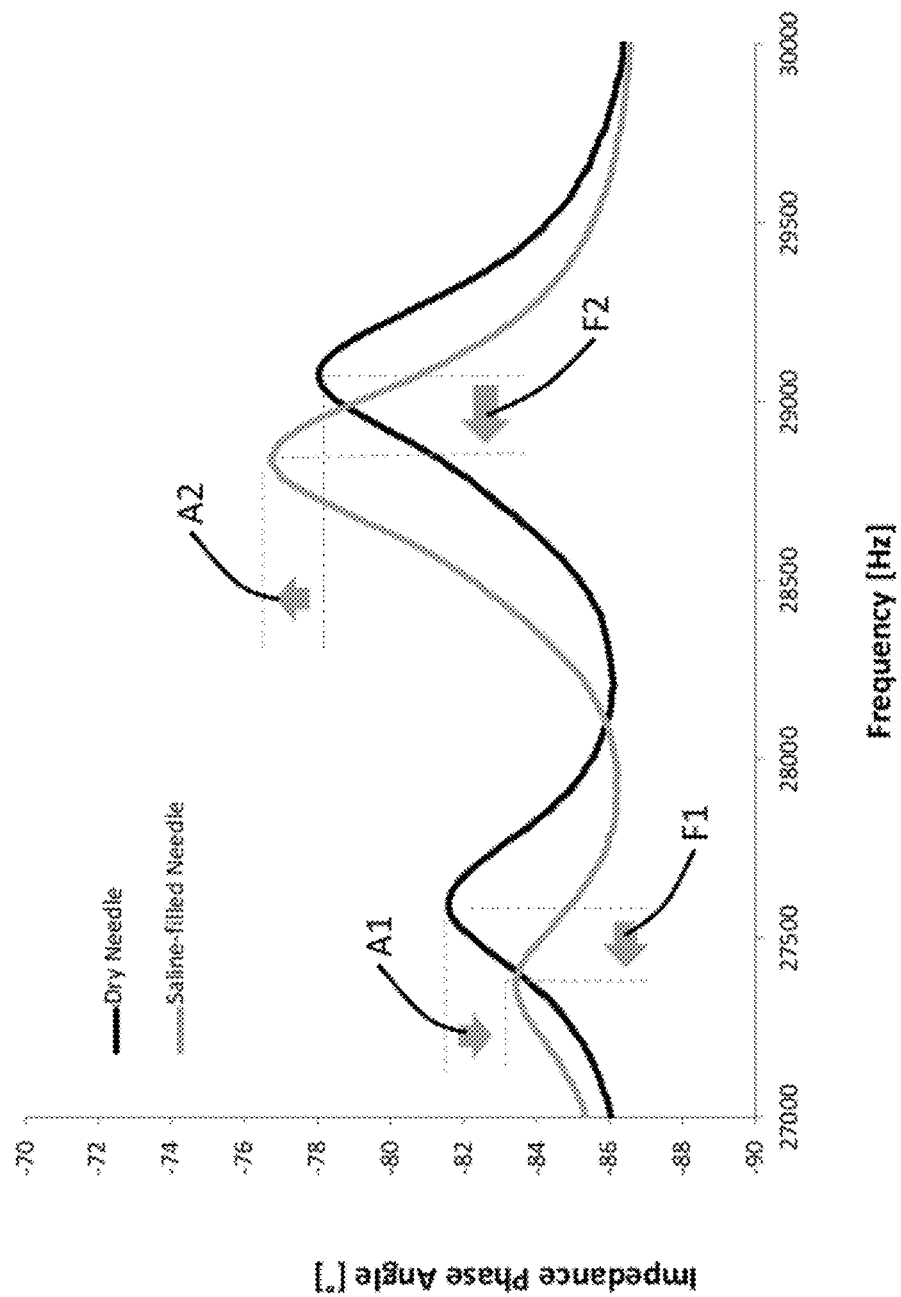
FIG. 31 is a graph of test data (e.g., impedance phase angle of a dry needle and impedance phase angle of a saline filled needle) of a reference device versus frequency (Hz)

FIG. 31 shows how impedance and phase measurements can exhibit a specific peak in the phase response. Such a peak can correspond to a known even, such as the presence of fluid in the a device's sharps member. Data in FIG. 31 was taken using a 25G atraumatic spinal needle with saline as the working fluid. A shift in phase of 100-400 Hz occurs when 2.5 cm of the needle (from the distal end) is filled with saline.

Continuing with the method in FIG. 27, as the clinician now advances the devices toward the subarachnoid space, as shown in step 2712. The baseline impedance sweep can be understood as the collection of data that corresponds to a baseline curve such as the "Dry Needle" curve shown in FIG. 31. The device then automatically performs additional sweeps, storing the additional changes in electromechanical properties, such as impedance phase angle, and compares those to a reference database that includes a pattern of impedance phase angles representative of a change in a physical condition of the device, such as when the sharps member penetrates the subarachnoid space and fills with cerebral spinal fluid. Such a known condition can be represented by the impedance phase angles shown in graph in FIG. 31 for a saline filled needle. In other words, as the device is advanced further into the living being, for example, in a direction from the epidural space toward the subarachnoid space, several sweeps can be performed to measure an impedance spectrum corresponding to the location of the device's needle as shown in step 2714. For each sweep, the measured impedance spectrum is compared to the baseline or original stored spectrum (or to a known value previously stored in memory) as shown in Step 2716. Steps 2712 and 2714 can be understood as the collection of data that corresponds to a measurement curve, such as the "Saline-filled Needle" curve shown in FIG. 31, which can occur when the needle in use is filled with cerebral spinal fluid (CSF) for comparison with the baseline.

In step 2718, the feedback system is utilized to measure whether there exists a difference between the measured impedance spectrum and the original/stored/baseline spectrum. If the difference is determined to be greater than a predetermined threshold value (such as A1, F1, A2 or F2 as shown in FIG. 31), the device can be configured to provide tactile, audible or visual indication (such as via a display as in step 2722) to the operator indicating its location (such as having encountered cerebral spinal fluid in the subarachnoid space) and/or programmed to automatically power down the actuation. In other words, once the needle has reached the epidural space, the device begins to monitor the impedance spectrum over a narrow frequency range (at low voltage, non-powered) to form a baseline. Each subsequent sweep of the spectrum will be compared against the initial baseline (e.g., the first sweep after entering epidural space). Once there has been a significant change in select features (e.g. a shift in impedance phase peaks) in the spectrum, corresponding to the change in electromechanical properties of the device as the needle fills with CSF, sensory indicator s(audio/visual/tactile) inform the clinician that needle has come into contact (i.e., filled partially or surrounded by) with CSF and has entered the subarachnoid space.

FIGS. 29-31 are graphical representations of data that can be gathered by a processor that receives signals from a sensor. The processor converts the received signal into a corresponding value representative of a particular electromechanical property. Through the use of software that controls the computing function of the processor, the processor can be programmed to recognize correlations within a single electromechanical property (such as a change in the property), or correlations between several electromechanical properties. For example, within the dashed box in FIG. 29, a vertical line represents a particular characteristic between various electromechanical properties and other measurable physical properties, such as an abrupt shift in resonance frequency, phase angle, impedance magnitude and/or penetration force that could be correlated to a predetermined value, or a set of values indicative of a known event. The dashed box in FIG. 30 shows an abrupt change in force, as measured by a force sensor (such as a low-voltage piezoelectric ring sensor). The abrupt change could be correlated to a known or predetermined change representative of, for example, successful penetration of the sharps member into the epidural space. The predetermined value, change, or known value can either included in a controlling software or stored in a database, such as an updatable database connected to the internet and to a central server to which updates can be sent by one user to be downloaded by another user. The subsystem can reference this value for updating particular parameters of the device 200 operation.

Referring to FIG. 33, a flow diagram illustrating steps of a method is illustrated. The method 3300 can be implemented as actions performed by a microprocessor, such as the microprocessor in FIG. 28 of a feedback subsystem, such as feedback subsystem 2400 of FIG. 24, for controlling the operation of a device, such as device 2599 of FIG. 25. The process begins with powering up (step 3302) of a control unit, in which the microprocessor is housed. The control unit provides power and electronically controls the functioning of an attached actuator of the device which can be energized to provide reciprocating motion to sharps/penetrating member for reducing the force required to penetrate into tissue, such as to perform a medical procedure. In step 3304 the actuator is interrogated in order to determine baseline properties that will be used to set the optimal driving parameters and verify the proper actuator is attached for the desired procedure. An interrogation can include verification that the actuator is functioning properly. An interrogation can include a sweep across a range frequencies, such as ultrasonic frequencies, in which a voltage signal is delivered to the actuator. It is possible that the controller can be designed to control a number of different actuators and/or perform a number of different medical procedures with various actuators.

For each medical procedure, there may be a specific set of driving parameters or instructions such as control of power level and/or voltage for a particular operation mode, what the duty cycle and/or pulse rate should be, what impedance phase to target in trying to maintain resonance, etc. For example, the procedural requirements for driving the actuator may be different for puncturing a vein than puncturing through the dura mater to the subarachnoid space as with placing a spinal needle for a cerebrospinal fluid (CSF) sampling procedure. The values for any driving parameter may be specific, or perhaps be bounded by upper and lower limits to ensure safe device function. Furthermore, some procedures may involve several intermediate steps, each of which may require different driving parameter settings. Procedure-specific device settings, including the possibility of a list of different device settings for individual procedural steps of a complete medical procedure, may be previously stored in a database and retrieved in step 3306. Based partially on the device interrogation of step 3304, as well as the needs of the specific medical procedure, the processor can selected optimum driving parameters in step 3308. Upon selecting optimum driving parameters, the processor can activate the actuator automatically (step 3310) or upon receiving manual input from the user. The term "activate" can include powering the actuator to achieve vibrational displacement capable of reducing penetration force (achieving an ROF effect), as well as lower power activation which employs the actuator as an active interrogator of the mechanical property changes that take place at the sharps/penetrating member-tissue interface. For instance, the electrical impedance spectrum of a piezo-electric device obtained by sending low-voltage sinusoidal signaling of varying frequencies to the active elements, such as piezoelectric actuator elements will change as the penetrating member is pushed into different media. For example, FIG. 23, shows examples of impedance spectrum upon penetrating through different media.

With device in activated state, the "Procedural Step Loop" is entered at step 3312. Within the "procedural step loop", the sharps/penetrating member that is attached to the actuator is steadily advanced through the living being tissue (step 3312), the actuator and/or integrated sensors (e.g. for measuring force, impedance magnitude, phase angle) are periodically monitored (step 3314) to measure and calculate changes in electromechanical properties, for example as the device and device components are influenced by tissue/fluids in and around the sharps/penetrating member (i.e., external forces acting on the device). In step 3318, the current electromechanical property values or time-varying trends in some or all of the electromechanical variables relating to the state of the actuator or the tissue/fluids in and around the sharps/penetrating member may be compared to a database of pre-defined property states or anticipated trends in those characteristics. If the pattern of current electromechanical properties or trends matches a pre-defined pattern or trend, for example within a statistical error, the current procedural step is complete (step 3320). If not, the driving parameters may be re-adjusted to maintain optimal performance and another iteration of the Procedural Step Loop commences. A user display may be updated (step 3322) each time through the loop to keep the user updated about progress through the current procedural step as well as indicate when the current step is completed. The user display may include haptic, audible, or visual feedback.

If the procedural step 3320 is completed, it must be determined whether the overall procedure, such as the medical procedure, is complete (step 3326). In other words, the subsystem must determine whether all intermediate procedural steps are complete or not. If so, the user can be notified (step 3322), and the system can enter a power down or standby state indefinitely (step 3330). The power down state may also be entered at any point in a procedure manually by the user, or when the monitored electromechanical properties indicate that a malfunction or unsafe state has been entered. Otherwise, if additional steps in the procedure are required to be performed, the controller transitions to the next procedural step (as described in step 3328). Before entering the Procedural Step Loop again, the driving parameters may be changed to accomplish the needs of the next procedural step according to the device settings database entry for that specific procedural step. The process continues until the desired medical procedure is completed.

A example demonstrating how the process would be implemented for a specific medical procedure is now described for that of a diagnostic cerebrospinal fluid (CSF) sampling procedure with respect to the method steps described above. A piezoelectric actuator is outfitted with a spinal needle incorporated into the distal horn. The system is powered up (3302) and the control unit performs a frequency sweep to obtain the impedance spectrum and identify the reference resonant frequency (3304), such as according to methods described in FIG. 32 and above. The processor can communicate with a database (as described in step 3306) to receive parameters for programming the device (3308) to operate with a set of initial driving parameters (e.g. voltage level, impedance phase angle to maintain in order to keep device operating at resonance, duty cycle, etc.) to accomplish the first procedural step: inserting the spinal needle through the ligamentum flavum with ROF effect. The device is activated (3310) and the clinician advances the spinal needle through tissues while monitoring the electromechanical properties (force sensor reading, abrupt impedance phase angle change, or impedance magnitude change; similar to that observed in FIG. 29) for evidence of pop-through as needle enters epidural space (Procedural Step Loop iterations). Meanwhile the operating frequency is regularly adjusted/updated (3324) to maintain optimal ROF effect (i.e. maintain actuator at resonance). Once evidence of ligamentum flavum pop-through is detected (3318, 3320), the next procedural step (detect CSF filling within needle) is initiated. For this step, the ROF effect may be less important so the driving voltage may be lowered (at step 3308, after querying the procedure-specific settings database) so displacements are less. This may be desired to minimize the chance for nerve damage. Even in a low-powered state, impedance spectrum changes may indicate CSF filling. Once CSF flow is detected, based primarily on specific changes in the impedance spectrum or by pattern match (implemented in steps 3316, 3318, and 3320), the procedure would be complete, and this would be indicated to the user (3322) and the actuator/system could be powered off (3330) while the clinician carries out the remaining steps to obtain and secure the CSF fluid sample for laboratory analysis.

Now that exemplary embodiments of the present invention have been shown and described in detail, various modifications and improvements thereon will become readily apparent to those skilled in the art. While the foregoing embodiments may have dealt with the penetration through skin, bone, veins and ligaments as exemplary biological tissues, the present invention can undoubtedly ensure similar effects with other tissues which are commonly penetrated within the body. For example there are multiplicities of other tools like central venous catheter introducers, laparoscopic instruments with associated sharps, cavity drainage catheter kits, and neonatal lancets, as well as procedures like insulin administration and percutaneous glucose testing, to name a few, where embodiments disclosed herein comprising sonically or ultrasonically driven sharps members may be used to precisely pierce or puncture tissues with minimal tinting. Accordingly, the spirit and scope of the present invention is to be construed broadly and limited only by the appended claims, and not by the foregoing specification.

Reference Labels

α Bend angle
A Static needle force curve
B Vibrating needle force curve
G1 Displacement Graph
LT Langevin actuator (also known as Langevin transducer)
PA1 Conventional biopsy needle
PA2 Conventional epidural needle
PA3 Conventional Syringe
PT Pressure transducer
S Switch
SP Side Port
ZN Zero node
Cannula
1' Cannula distal end
2 Stylet
3 Distal tip
4 Stylet tip angled face
5 Tuohy needle
6 Tuohy curved tip
7 Tip opening
9 Front portion
10 Tubular body
11 Biasing element
12 Plunger
14 Inner Stylet
15 Outer trocar tube
16 APA needle 16b Alternate embodiment
20 Penetrating member
100 Langevin actuator
110 Horn
111 Support wings
112 Rear mass
114 Piezoelectric elements
114b Electrical conductors
115 Sterilization sleeve
116 Bolt
117 Battery & inverter compartment
118 Handle
120 Seal
121 Distal face
122 Distal opening
123 Luer taper nose
124 Proximal opening
126 Bore
126a Short bore
128 Attachment fitting
129 Catheter
130 Hollow needle
130a Distal end of hollow needle
130b Proximal end of hollow needle
132 Plunger handle
134 Plunger shaft
134a Proximal end of plunger shaft
134b Distal end of plunger shaft
136 Plunger seal
142 Inner stylet handle
144 Inner stylet shaft
146 Inner stylet tip
148 Trocar attachment fitting
150 Outer trocar body
152 Distal trocar opening
154 Distal trocar tip
200 Penetrating introducer
202b More preferred embodiment
202c Most preferred embodiment
201 Supported introducer
202 Catheterization introducer
300 Bone biopsy device
400 Advanced bone biopsy device
500 APA syringe
500b Alternate embodiment
510 Amplified piezoelectric actuator (APA)
512 Frame
512a Proximal end of frame
512b Distal end of frame
513 Penetrating member
513a Proximal end of penetrating member
513b Distal tip of penetrating member
514 Piezoelectric material
516 APA attachment point
518 Handle
521 Handle distal opening
524 Handle proximal opening
525 Penetrating member hub
526 APA bore
600 Cymbal syringe
600b Alternate embodiment
610 Cymbal actuator
612 Endcap
612a Proximal endcap
612b Distal endcap
626 Cymbal bore
616 Cymbal attachment point
700 General side port configuration
700a First side port configuration
700b Second side port configuration
701 Feedback subsystem
702 Microcontroller
704 Drive Electronics
800 Feedback capable reduction of force tool
900 Medical tool using voice coil actuator
900b Alternate voice coil embodiment
902 Conducting coil
904 Magnetic member
906 Coil support tube
910 Body
912 Driving tube
914 Extension member
916a First attachment point
916b Second attachment point
918 First conductive attachment site
920 Second conductive attachment site
922 Second conductive coil
1000 Medical tool using solenoid actuator
1002 Solenoid coil
1004 Magnets
1014 Spring
1020 Pressure feedback system
1021 Reservoir with integrated pump
1022 Flexible tubing
1023 Attachment fitting
1024 Base
1025 On/off switch
1026 Light emitting diode
2100 Electrical Cutoff Configuration
2400 Feedback subsystem
2402 Microcontroller
2404 Drive electronics
2500 Actuator
2501 first opening
2502 second opening
2503 third opening
2504 channel
2506 sidewall
2507 flat surface
2508 volume
2510 Displaceable Member
2510a First Portion
2510a' Distal Tip
2510b Second Portion
2520 Sharps Member
2512 Rear Mass
2514 Piezostack
2515 Distal end
2514a piezoelectric element
2514b piezoelectric element
2518 Handpiece
2522 Force Sensor
2524 distal interface
2525 proximal interface
2526 gap
2599 Device

What is claimed is:
1. A medical device for penetrating living being tissue, said device comprising:
a penetrating member which is axially reciprocated relative to a body of said medical device, wherein axial reciprocation of the penetrating member reduces a force necessary to penetrate said living being tissue;

a driving actuator coupled to said penetrating member, wherein said driving actuator generates said axial reciprocation, wherein an interrogation that includes a frequency sweep is performed on the driving actuator prior to penetration of the living being tissue;

a feedback subsystem which includes a processor and a memory, wherein the memory stores predetermined electromechanical measurement data, the memory including at least one comparison function, the at least one comparison function including at least one measurement parameter, said at least one comparison function executable by said processor, said feedback subsystem detecting changes of electromechanical properties related to the operation of said penetrating member; and at least one sensor in electronic communication with said processor, said at least one sensor being mounted in communication with at least one of said penetrating member and said driving actuator, said at least one sensor generating electromechanical measurement data relative to the motion of said penetrating member;

said processor incorporating said sensor electromechanical measurement data and said predetermined electromechanical measurement data into said at least one comparison function, said at least one comparison function:
 (i) comparing said sensor electromechanical measurement data with said predetermined electromechanical measurement data in accordance with at least one measurement parameter;
 (ii) determining whether said sensor electromechanical measurement data matches at least a portion of said predetermined electromechanical measurement data as determined by said at least one measurement parameter;
 (iii) selectively modifying the action of said driving actuator, to achieve an optimal driving parameter of said driving actuator, through a combination of input from the sensor electrochemical measurement data and the predetermined electrochemical measurement data, said feedback subsystem detecting changes of electromechanical properties related to the reciprocation of said penetrating member, said processor continuously modifying the action of said driving actuator from suboptimal driving parameters while reciprocation occurs to more optimal driving parameters while reciprocation occurs, the suboptimal driving parameters driving the driving actuator at a frequency other than a resonance frequency and the more optimal driving parameters driving the driving actuator at the resonance frequency and
 (iv) indicating a status relating to said penetrating member to an operator;

wherein electromechanical property values of the driving actuator are measured during the axial reciprocation and compared with the predetermined electromechanical measurement data and are identified by the processor based upon the comparison to indicate that the penetrating member is working within the more optimal driving parameters or is failing to operate within the more optimal driving parameters.

2. The medical device of claim 1, wherein:
said predetermined electromechanical measurement data comprises at least one threshold phase angle change and said at least one measurement parameter comprises a plurality of impedance phase angles corresponding to at least one respective frequency associated with said axial reciprocation; and said comparison function further comprises:
 (i) calculating a difference between first and second impedance phase angles at a first frequency and comparing said difference to said predetermined electromechanical measurement data; and
 (ii) selectively modifying the action of said driving actuator by adjusting said first frequency by one of:
  a. a predetermined frequency value; and
  b. adjusting said first frequency to a second frequency associated with an impedance phase angle of about 0.

3. The medical device of claim 2, wherein said first frequency is a resonant frequency of the medical device.

4. The medical device of claim 2, wherein said at least one respective frequency is at least one selected from the range consisting of about 30 kHz to about 40 kHz.

5. The medical device of claim 2, wherein said at least one respective frequency is at least one selected from the range consisting of about 20 kHz to about 25 kHz.

6. The medical device of claim 1, wherein said at least one measurement parameter is selected from the group consisting of: impedance phase angle, impedance magnitude, voltage magnitude, current magnitude, and force.

7. The medical device of claim 1 wherein said at least one measurement parameter further comprises an impedance phase angle in a control signal of said driving actuator.

8. The medical device of claim 1 wherein said at least one measurement parameter further comprises a conductivity of said driving actuator.

9. The medical device of claim 1 wherein said electromechanical measurement parameter further comprises a voltage change in a control signal of said driving actuator.

10. The medical device of claim 1 wherein said at least one sensor further comprises a force sensor in mechanical communication with said driving actuator.

11. The medical device of claim 1, further comprising a separator mass mounted between said force sensor and said driving actuator.

12. The medical device of claim 1, wherein said at least one sensor further comprises an impedance analyzer.

13. The medical device of claim 1 wherein said driving actuator is a Langevin actuator.

14. The method of claim 1 wherein said driving actuator further comprises at least one piezoelectric element.

15. The medical device of claim 1 wherein said driving actuator further comprises a voice coil.

16. The medical device of claim 1 wherein said driving actuator is one of a pneumatic and fluidic actuator.

17. The medical device of claim 1 wherein said driving actuator further comprises:
 at least one piezoelectric element for converting electrical energy into oscillatory motion when energized;
 a first channel extending to a distal end of said driving actuator; and
 a second channel having a first end in communication with said first channel and a second end positioned at an exterior surface of said driving actuator.

18. The medical device of claim 17 wherein a third channel extends through said at least one piezoelectric element, said first and third channels being aligned, and wherein said driving actuator further comprises an anchor having a fourth channel extending therethrough along a longitudinal axis of said anchor, said fourth channel being aligned with said first and third channels to form a continuous channel through said driving actuator.

19. The medical device of claim 1 wherein said penetrating member is selected from the group consisting of: a hypodermic needle, a catheterization needle, a Tuohy needle, a bone biopsy trocar, a spinal needle, a nerve block needle, trocar access ports and a interventional radiology needle.

20. The medical device of claim 1, wherein an exterior surface of said driving actuator comprises a side port for providing one of: fluid communication with and passage of a catheter within said penetrating member.

* * * * *